United States Patent
Taneda et al.

(10) Patent No.: US 10,050,215 B2
(45) Date of Patent: Aug. 14, 2018

(54) LIGHT-EMITTING MATERIAL, ORGANIC LIGHT-EMITTING DEVICE, AND COMPOUND

(71) Applicant: KYULUX, INC., Fukuoka-shi, Fukuoka (JP)

(72) Inventors: Masatsugu Taneda, Fukuoka (JP); Katsuyuki Shizu, Fukuoka (JP); Hiroyuki Tanaka, Fukuoka (JP); Hiroki Noda, Fukuoka (JP); Hajime Nakanotani, Fukuoka (JP); Chihaya Adachi, Fukuoka (JP)

(73) Assignee: KYULUX, INC., Fukuoka (JP)

( * ) Notice: Subject to any disclaimer, the term of this patent is extended or adjusted under 35 U.S.C. 154(b) by 4 days.

(21) Appl. No.: 15/121,461

(22) PCT Filed: Feb. 25, 2015

(86) PCT No.: PCT/JP2015/055314
§ 371 (c)(1),
(2) Date: Aug. 25, 2016

(87) PCT Pub. No.: WO2015/129715
PCT Pub. Date: Sep. 3, 2015

(65) Prior Publication Data
US 2016/0372682 A1   Dec. 22, 2016

(30) Foreign Application Priority Data

Feb. 28, 2014   (JP) .................. 2014-037719

(51) Int. Cl.
| | |
|---|---|
| H01L 51/00 | (2006.01) |
| C07C 255/58 | (2006.01) |
| C07D 209/86 | (2006.01) |
| C09K 11/06 | (2006.01) |
| H01L 51/50 | (2006.01) |

(52) U.S. Cl.
CPC ........ *H01L 51/0072* (2013.01); *C07C 255/58* (2013.01); *C07D 209/86* (2013.01); *C09K 11/06* (2013.01); *H01L 51/0059* (2013.01); *C09K 2211/1007* (2013.01); *C09K 2211/1014* (2013.01); *C09K 2211/1029* (2013.01); *C09K 2211/1033* (2013.01); *C09K 2211/1037* (2013.01); *C09K 2211/1044* (2013.01); *H01L 51/5012* (2013.01)

(58) Field of Classification Search
CPC . H01L 51/00; H01L 51/0072; H01L 51/0059; C07C 255/58; C07D 209/86; C09K 11/06
See application file for complete search history.

(56) References Cited

U.S. PATENT DOCUMENTS

2009/0072727 A1   3/2009   Takeda
2014/0231715 A1   8/2014   Stoessel et al.

FOREIGN PATENT DOCUMENTS

| | | |
|---|---|---|
| CN | 103502388 | 1/2014 |
| CN | 105051014 | 11/2015 |
| CN | 105209434 | 12/2015 |
| EP | 2 039 737 | 3/2009 |
| JP | 2009094486 A | 4/2009 |
| JP | 2011176258 A | 9/2011 |
| WO | 2013/154064 A1 | 10/2013 |
| WO | 2013172255 | 11/2013 |
| WO | 2014/146752 | 9/2014 |
| WO | 2012143079 A1 | 10/2016 |

OTHER PUBLICATIONS

International Preliminary Report on Patentability for corresponding PCT International Application No. PCT/JP2015/055314, dated Sep. 15, 2016, with English translation.
International Search Report for corresponding PCT International Application No. PCT/JP2015/055314.
Mi et al., Impact of substitution on the reorganization energy of bis-triarylamine derivatives, Journal of Molecular Structure: Theochem, 940:1-5 (2010).
European search report dated Oct. 5, 2017 from corresponding European patent application No. 15755183.9.
Chinese office action dated Jun. 19, 2017 for Chinese application No. 201580010956.2, with English translation.
(Continued)

*Primary Examiner* — Nyeemah A Grazier
(74) *Attorney, Agent, or Firm* — Browdy and Neimark, PLLC

(57) ABSTRACT

A compound represented by the general formula (1) is useful as a light-emitting material. $R^1$, $R^3$, and $R^5$ each represent a cyano group, or $R^1$, $R^2$, $R^4$, and $R^5$ each represent a cyano group; and the others of $R^1$ to $R^6$ each represent a group represented by any one of the following general formula (4), etc.

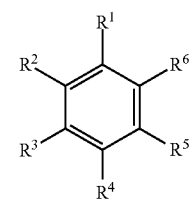

(1)

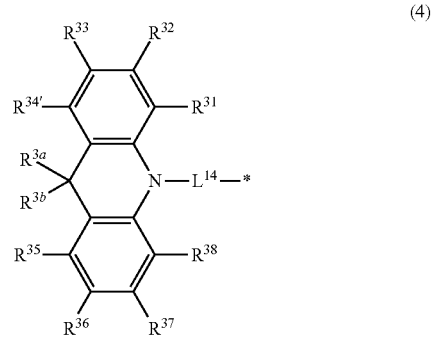

(4)

10 Claims, 8 Drawing Sheets

(56) References Cited

OTHER PUBLICATIONS

Uoyama, et al., Highly efficient organic light—emitting diodes from delayed fluorescence, Nature, Dec. 13, 2012 pp. 234-240, vol. 492.
Office Action for corresponding Taiwanese Patent Application No. 104106402, dated Feb. 13, 2018, with English translation.
Office Action for corresponding Chinese Patent Application No. 201580010956.2, dated Mar. 14, 2018, with English translation.

LIGHT-EMITTING MATERIAL, ORGANIC LIGHT-EMITTING DEVICE, AND COMPOUND

TECHNICAL FIELD

The present invention relates to a compound that is useful as a light-emitting material, and an organic light-emitting device using the same.

BACKGROUND ART

An organic light-emitting device, such as an organic electroluminescent device (organic EL device), has been actively studied for enhancing the light emission efficiency thereof. In particular, various studies for enhancing the light-emitting efficiency have been made by newly developing and combining an electron transporting material, a hole transporting material, a light-emitting material and the like constituting an organic electroluminescent device. For example, compounds having a substituted amino group, such as a carbazolyl group and a diphenylamino group, have been known as the material for the light-emitting layer, and among these, one having a cyano group has been known. For example PTL 1 describes that a compound having a carbazolyl group (Cz) and a cyano group represented by the following formula can be used as a host material of a light-emitting layer.

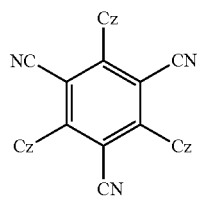

CITATION LIST

Patent Literature

PTL 1: JP-A-2009-94486

SUMMARY OF INVENTION

Technical Problem

PTL 1 has concretely demonstrated that various compounds are useful as a host material of a light-emitting layer, but does not verify for the other applications. A light-emitting material (dopant material) is different from a host material in demanded properties and functions, and therefore there is no evidence for the usefulness of the compound described in PTL 1 as a light-emitting material.

Under the circumstances, the present inventors started to investigate variously a group of compounds having a substituted amino group and a cyano group, and have made accumulated studies for finding a compound having excellent light emission characteristics from many analogous compounds. The inventors have made earnest investigations for providing a general formula of the compounds useful as a light-emitting material and generalizing the structure of an organic light-emitting device having a high light emission efficiency.

Solution to Problem

As a result of the earnest investigations performed, the inventors have found that among the compounds having a substituted amino group and a cyano group, compounds having a particular structure have excellent properties as a light-emitting material. The inventors also have found that the group of compounds includes compounds that are useful as a delayed fluorescent material, and have clarified that an organic light-emitting device having a high light emission efficiency can be provided inexpensively. Based on the knowledge, the inventors have provided the inventions as measures for solving the problems.

[1] A light-emitting material containing a compound represented by the following general formula (1):

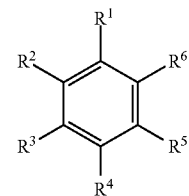

General Formula (1)

wherein in the general formula (1), $R^1$, $R^3$, and $R^5$ each represent cyano group, or $R^1$, $R^2$, $R^4$, and $R^5$ each represent a cyano group; and the others of $R^1$ to $R^6$ each independently represent a group represented by any one of the following general formulae (2) to (8)

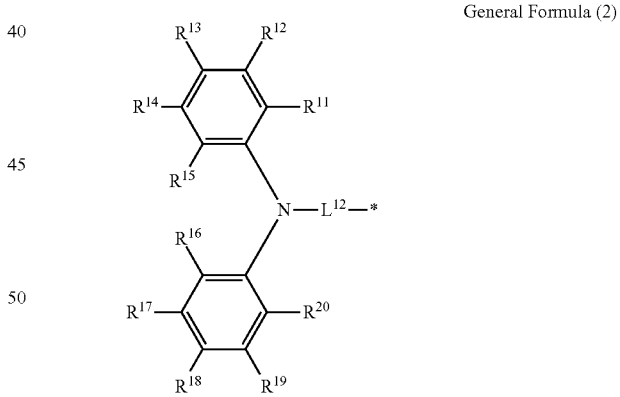

General Formula (2)

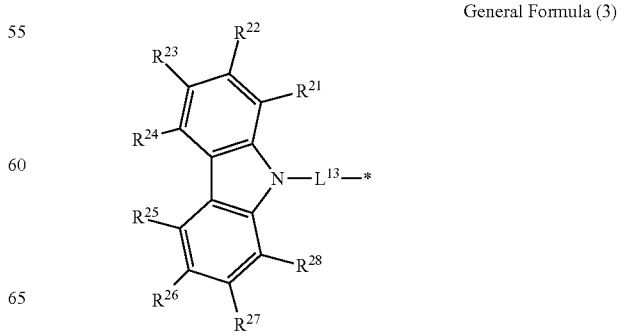

General Formula (3)

3
-continued

General Formula (4)

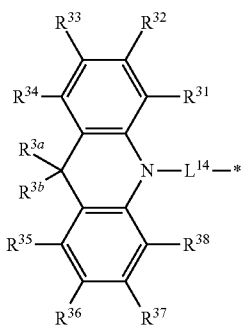

General Formula (5)

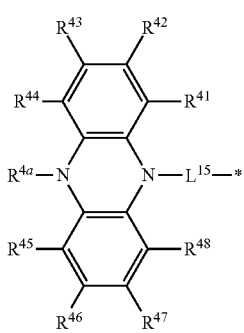

General Formula (6)

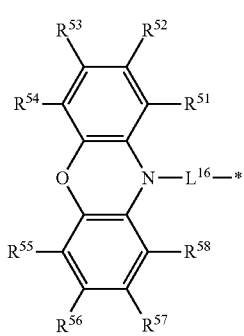

General Formula (7)

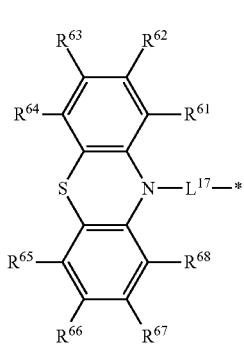

4
-continued

General Formula (8)

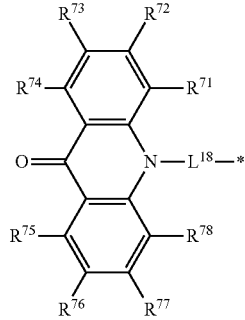

wherein in the general formulae (2) to (8), $L^{12}$ to $L^{18}$ each represent a single bond or a substituted or unsubstituted arylene group; * represents a position bonded to the benzene ring in the general formula (1); and $R^{11}$ to $R^{20}$, $R^{21}$ to $R^{28}$, $R^{31}$ to $R^{38}$, $R^{3a}$, $R^{3b}$, $R^{41}$ to $R^{48}$, $R^{4a}$, $R^{51}$ to $R^{58}$, $R^{61}$ to $R^{68}$, and $R^{71}$ to $R^{78}$ each independently represent a hydrogen atom or a substituent, provided that $R^{11}$ and $R^{12}$, $R^{12}$ and $R^{13}$, $R^{13}$ and $R^{14}$, $R^{14}$ and $R^{15}$, $R^{16}$ and $R^{17}$, $R^{17}$ and $R^{18}$, $R^{18}$ and $R^{19}$, $R^{19}$ and $R^{20}$, $R^{21}$ and $R^{22}$, $R^{22}$ and $R^{23}$, $R^{23}$ and $R^{24}$, $R^{24}$ and $R^{25}$, $R^{25}$ and $R^{26}$, $R^{26}$ and $R^{27}$, $R^{27}$ and $R^{28}$, $R^{31}$ and $R^{32}$, $R^{32}$ and $R^{33}$ and $R^{34}$, $R^{35}$ and $R^{36}$ $R^{36}$ and $R^{37}$, $R^{37}$ and $R^{38}$, $R^{3a}$ and $R^{3b}$, $R^{41}$ and $R^{42}$, $R^{42}$ and $R^{43}$, $R^{43}$ and $R^{44}$, $R^{45}$ and $R^{46}$, $R^{46}$ and $R^{47}$, $R^{47}$ and $R^{48}$, $R^{51}$ and $R^{52}$, $R^{52}$ and $R^{53}$, $R^{53}$ and $R^{54}$, $R^{55}$ and $R^{56}$, $R^{56}$ and $R^{57}$, $R^{57}$ and $R^{58}$, $R^{61}$ and $R^{62}$, $R^{62}$ and $R^{63}$, $R^{63}$ and $R^{64}$, $R^{65}$ and $R^{66}$, $R^{66}$ and $R^{67}$, $R^{67}$ and $R^{68}$, $R^{71}$ and $R^{72}$, $R^{72}$ and $R^{73}$, $R^{73}$ and $R^{74}$, $R^{75}$ and $R^{76}$, $R^{76}$ and $R^{77}$, and $R^{77}$ and $R^{78}$ each may be bonded to each other to form a cyclic structure.

[2] The light-emitting material according to the item [1], wherein in the general formula (1), $R^1$, $R^3$, and $R^5$ each represent a cyano group.

[3] The light-emitting material according to the item [1], wherein in the general formula (1), $R^1$, $R^2$, $R^4$, and $R^5$ each represent a cyano group.

[4] The light-emitting material according to any one of the items [1] to [3], wherein in the general formulae (2) to (8), $L^{12}$ to $L^{18}$ each represent a substituted or unsubstituted phenylene group.

[5] The light-emitting material according to any one of the items [1] to [4], wherein in the general formula (1), all the others of $R^1$ to $R^6$ each represent a group represented by the general formula (2).

[6] The light-emitting material according to any one of the items [1] to [4], wherein in the general formula (1), all the others of $R^1$ to $R^6$ each represent a group represented by the general formula (3).

[7] The light-emitting material according to any one of the items [1] to [6], wherein the molecule has a rotationally symmetric structure.

[8] A delayed fluorescence emitter containing a compound represented by the general formula (1).

[9] An organic light-emitting device containing the light-emitting material according to any one of the items [1] to [7].

[10] The organic light-emitting device according to the item [9], wherein the organic light-emitting device emits delayed fluorescent light.

[11] The organic light-emitting device according to the item [9] or [10], wherein the organic light-emitting device is an organic electroluminescent device.

[12] A compound represented by the following general formula (1'):

General Formula (1')

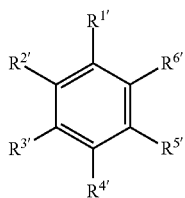

wherein in the general formula (1'), $R^{1\prime}$, $R^{3\prime}$, and $R^{5\prime}$ each represent a cyano group, or $R^{1\prime}$, $R^{2\prime}$, $R^{4\prime}$, and $R^{5\prime}$ each represent a cyano group; and the others of $R^{1\prime}$ to $R^{6\prime}$ each independently represent a group represented by any one of the following general formulae (2') to (8'):

General Formula (2')

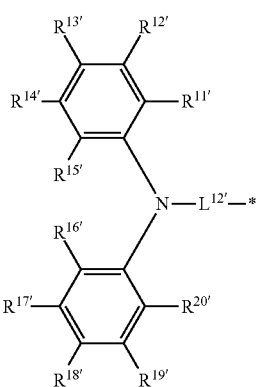

General Formula (3')

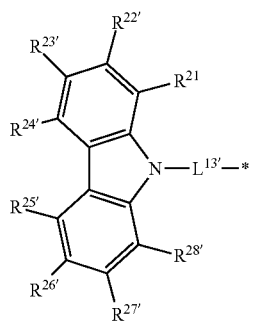

General Formula (4')

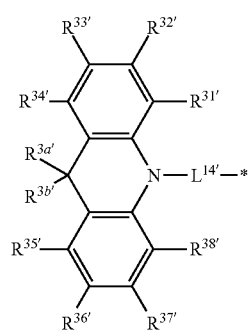

General Formula (5')

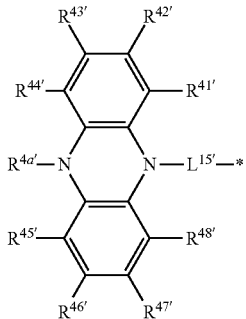

General Formula (6')

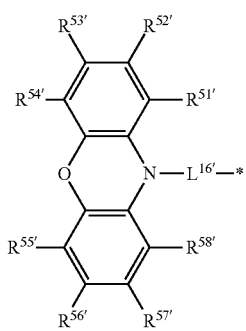

General Formula (7')

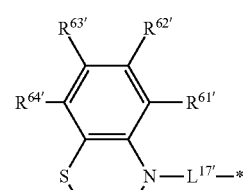

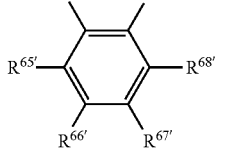

General Formula (8')

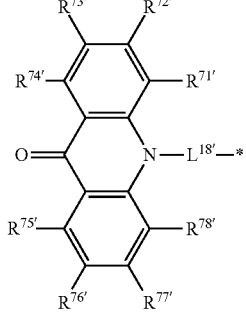

wherein in the general formulae (2') to (8'), $L^{12\prime}$ to $L^{18\prime}$ each represent a single bond or a substituted or unsubstituted arylene group; * represents a position bonded to the benzene ring in the general formula (1'); and $R^{11\prime}$ to $R^{20\prime}$, $R^{21\prime}$ to $R^{28\prime}$, $R^{31\prime}$ to $R^{38\prime}$, $R^{3a\prime}$, $R^{3b\prime}$, $R^{41\prime}$ to $R^{48\prime}$, $R^{4a\prime}$, $R^{51\prime}$ to $R^{58\prime}$, $R^{61\prime}$ to $R^{68\prime}$, and $R^{71\prime}$ to $R^{78\prime}$ each independently represent a hydrogen atom or a substituent, provided that $R^{11\prime}$ and $R^{12\prime}$, $R^{12\prime}$ and $R^{13\prime}$, $R^{13\prime}$ and $R^{14\prime}$, $R^{14\prime}$ and $R^{15\prime}$, $R^{16\prime}$ and $R^{17\prime}$, $R^{17\prime}$ and $R^{18\prime}$, $R^{18\prime}$ and $R^{19\prime}$, $R^{19\prime}$ and $R^{20\prime}$, $R^{21\prime}$ and $R^{22\prime}$, $R^{22\prime}$ and $R^{23\prime}$, $R^{23\prime}$ and $R^{24\prime}$, $R^{24\prime}$ and $R^{25\prime}$, $R^{25\prime}$ and $R^{26\prime}$, $R^{26\prime}$ and $R^{27\prime}$, $R^{27\prime}$, and $R^{28\prime}$, $R^{31\prime}$ and $R^{32\prime}$, $R^{32\prime}$ and $R^{33\prime}$, $R^{33\prime}$ and $R^{34\prime}$, $R^{35\prime}$ and $R^{36\prime}$, $R^{36\prime}$ and $R^{37\prime}$, $R^{37\prime}$ and $R^{38\prime}$, $R^{3a\prime}$ and $R^{3b'}$, $R^{41'}$ and $R^{42'}$, $R^{42'}$ and $R^{43'}$, $R^{43'}$ and $R^{44'}$, $R^{45'}$ and $R^{46'}$, $R^{46'}$ and $R^{47'}$, $R^{47'}$ and $R^{48'}$, $R^{51'}$ and $R^{52'}$, $R^{52'}$ and $R^{53'}$, $R^{53'}$ and $R^{54'}$, $R^{55'}$ and $R^{56'}$, $R^{56'}$ and $R^{57'}$, $R^{57'}$ and $R^{58'}$, $R^{61'}$ and $R^{62'}$, $R^{62'}$ and $R^{63'}$, $R^{63'}$ and $R^{64'}$, $R^{65'}$ and $R^{66'}$, $R^{66'}$ and $R^{67'}$, $R^{67'}$ and $R^{68'}$, $R^{71'}$ and $R^{72'}$, $R^{72'}$ and $R^{73'}$, $R^{73'}$ and $R^{74'}$, $R^{75'}$ and $R^{76'}$, $R^{76'}$ and $R^{77'}$, and $R^{77'}$ and $R^{78'}$ each may be bonded to each other to form a cyclic structure.

Advantageous Effects of Invention

The compound of the invention is useful as a light-emitting material. The compound of the invention includes one that emits delayed fluorescent light. The organic light-emitting device using the compound of the invention as a light-emitting material is capable of achieving a high light emission efficiency.

DESCRIPTION OF EMBODIMENTS

Figure 1:
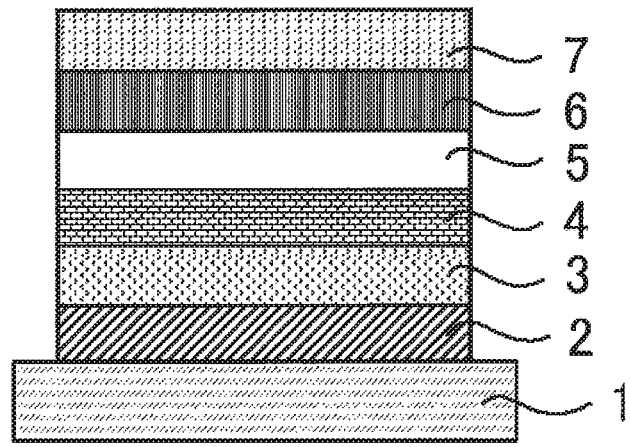
FIG. 1 shows a schematic cross sectional view showing an example of a layer structure of an organic electroluminescent device.

The contents of the invention will be described in detail below. The constitutional elements may be described below with reference to representative embodiments and specific examples of the invention, but the invention is not limited to the embodiments and the examples. In the description, a numerical range expressed with reference to an upper limit and/or a lower limit means a range that includes the upper limit and/or the lower limit. In the invention, the hydrogen atom that is present in the compound used in the invention is not particularly limited in iso tope species, and for example, all the hydrogen atoms in the molecule may be $^1H$, and all or a part of them may be $^2H$ (deuterium (D)).

Compound Represented by General Formula (1)

The light-emitting material of the invention, contains a compound represented by the following general formula (1).

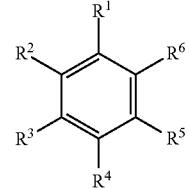

General Formula (1)

In the general formula (1), $R^1$, $R^3$, and $R^5$ each represent cyano group, or $R^1$, $R^2$, $R^4$, and $R^5$ each represent a cyano group; and the others of $R^1$ to $R^6$ each independently represent a group represented by any one of the following general formulae (2) to (8). Specifically, in the case where $R^1$, $R^3$, and $R^5$ each represent a cyano group, the other $R^2$, $R^4$, and $R^6$ each independently represent a group represented by any one of the following general formulae (2) to (8). In the case where $R^1$, $R^2$, $R^4$, and $R^5$ each represent a cyano group, the other $R^3$ and $R^6$ each independently represent a group represented by any one of the following general formulae (2) to (8).

The others of $R^1$ to $R^6$ each may represent any one of the general formulae (2) to (8) or may represent the different general formulae.

In the case where all the others of $R^1$ to $R^6$ each represent any one of the general formulae (2) to (8), all the others of $R^1$ to $R^6$ preferably are groups having the same structure. In the case where all the others of $R^1$ to $R^6$ are groups having the same structure, the compound represented by the general formula (1) has a rotationally symmetric structure, and the compound that has a structure, in which all the others of $R^1$ to $R^6$ have the same structures, is useful, for example, for using as a dopant.

The compound that has a structure, in which part or all of the others of $R^1$ to $R^6$ have the different structures, is also useful. The compound is useful, for example, in the case where a layer formed only of the compound (neat layer) is formed and used as a light-emitting layer.

General Formula (2)

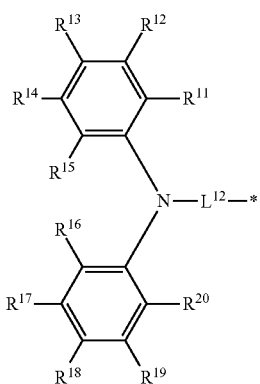

General Formula (3)

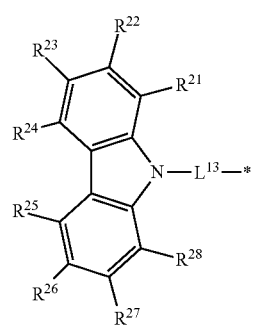

General Formula (4)

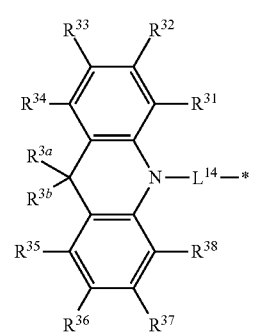

General Formula (5)

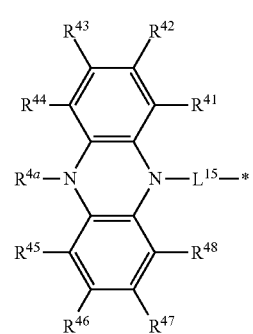

General Formula (6)

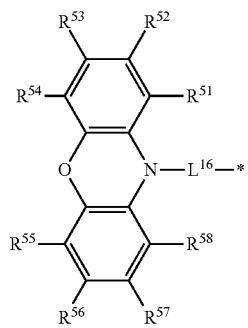

General Formula (7)

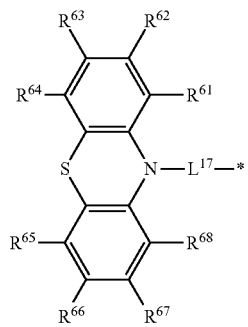

General Formula (8)

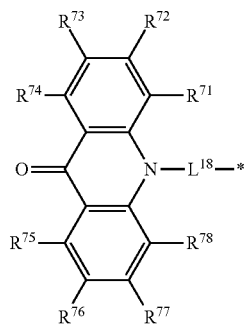

In the general formulae (2) to (8), $L^{12}$ to $L^{18}$ each represent a single bond or a substituted or unsubstituted arylene group, and * represents a position bonded to the benzene ring in the general formula (1). In the case where $L^{12}$ to $L^{18}$ each represent an arylene group, the arylene group is preferably an arylene group having from 6 to 18 carbon atoms. Examples of the arylene group having from 6 to 18 carbon atoms include a phenylene group, a biphenylene group, a fluorenylene group, and a triphenyienylene group, and the linking group is more preferably a phenylene group, and further preferably a 1,4-phenylene group. The description and the preferred ranges for the case where the arylene group has a substituent, reference may be made to the description and the preferred ranges of the substituent that the following $R^{11}$ to $R^{20}$ and the like may have. $L^{12}$ to $L^{18}$ each also preferably represent a single bond.

$R^{11}$ to $R^{20}$, $R^{21}$ to $R^{28}$, $R^{31}$ to $R^{38}$, $R^{3a}$, $R^{3b}$, $R^{41}$ to $R^{48}$, $R^{4a}$, $R^{51}$ to $R^{58}$, $R^{61}$ to $R^{68}$, and $R^{71}$ to $R^{78}$ each independently represent a hydrogen atom or a substituent. The number of the substituent is not particularly limited, and all $R^{11}$ to $R^{20}$, $R^{21}$ to $R^{28}$, $R^{31}$ to $R^{38}$, $R^{3a}$, $R^{3b}$, $R^{41}$ to $R^{48}$, $R^{4a}$, $R^{51}$ to $R^{58}$, $R^{61}$ to $R^{68}$, and $R^{71}$ to $R^{78}$ may be unsubstituted (i.e., hydrogen atoms). In each of the general formulae (2) to (8), in the case where two or more of $R^{11}$ to $R^{20}$, $R^{21}$ to $R^{28}$, $R^{31}$ to $R^{38}$, $R^{3a}$, $R^{3b}$, $R^{41}$ to $R^{48}$, $R^{4a}$, $R^{51}$ to $R^{58}$, $R^{61}$ to $R^{68}$, and $R^{71}$ to $R^{78}$ each represent a substituent, the plural substituents may be the same as or different from each other.

Examples of the substituent that may be represented by $R^{11}$ to $R^{20}$, $R^{21}$ to $R^{28}$, $R^{31}$ to $R^{38}$, $R^{3a}$, $R^{3b}$, $R^{41}$ to $R^{48}$, $R^{4a}$, $R^{51}$ to $R^{58}$, $R^{61}$ to $R^{68}$, and $R^{71}$ to $R^{78}$ include a hydroxyl group, a halogen atom, a cyano group, an alkyl group having from 1 to 20 carbon atoms, an alkoxy group having from 1 to 20 carbon atoms, an alkylthio group having from 1 to 20 carbon atoms, an alkyl-substituted amino group having from 1 to 20 carbon atoms, an acyl group having from 2 to 20 carbon atoms, an aryl group having from 6 to 40 carbon atoms, a heteroaryl group having from 3 to 40 carbon atoms, an alkenyl group having from 2 to 10 carbon atoms, an alkynyl group having from 2 to 10 carbon atoms, an alkoxycarbonyl group having from 2 to 10 carbon atoms, an alkylsulfonyl group having from 1 to 10 carbon atoms, a haloalkyl group having from 1 to 10 carbon atoms, an amide group, an alkylamide group having from 2 to 10 carbon atoms, a trialkylsilyl group having from 3 to 20 carbon atoms, a trialkylsilylalkyl group having from 4 to 20 carbon atoms, a trialkylsilylalkenyl group having from 5 to 20 carbon atoms, a trialkylsilylalkenyl group having from 5 to 20 carbon atoms, and a nitro group. In these specific examples, the substituent that is capable of being further substituted with a substituent may be substituted. More preferred examples of the substituent include a halogen atom, a cyano group, a substituted or unsubstituted alkyl group having from 1 to 20 carbon atoms, an alkoxy group having from 1 to 20 carbon atoms, a substituted or unsubstituted aryl group having from 6 to 40 carbon atoms, a substituted or unsubstituted heteroaryl group having from 3 to 40 carbon atoms, and a dialkyl-substituted amino group having from 1 to 20 carbon atoms. Further preferred examples of the substituent include a fluorine atom, a chlorine atom, a cyano group, a substituted or unsubstituted alkyl group having from 1 to 10 carbon atoms, a substituted or unsubstituted alkoxy group having from 1 to 10 carbon atoms, a substituted or unsubstituted aryl group having from 6 to 15 carbon atoms, and a substituted or unsubstituted heteroaryl group having from 3 to 12 carbon atoms.

$R^{11}$ and $R^{12}$, $R^{12}$ and $R^{13}$, $R^{13}$ and $R^{14}$, $R^{14}$ and $R^{15}$, $R^{16}$ and $R^{17}$, $R^{17}$ and $R^{18}$, $R^{18}$ and $R^{19}$, $R^{19}$ and $R^{20}$, $R^{21}$ and $R^{22}$, $R^{22}$ and $R^{23}$, $R^{23}$ and $R^{24}$, $R^{24}$ and $R^{25}$, $R^{25}$ and $R^{26}$, $R^{26}$ and $R^{27}$, $R^{27}$ and $R^{28}$, $R^{31}$ and $R^{32}$, $R^{32}$ and $R^{33}$, $R^{33}$ and $R^{34}$, $R^{35}$ and $R^{36}$, $R^{36}$ and $R^{37}$, $R^{37}$ and $R^{38}$, $R^{3a}$ and $R^{3b}$, $R^{41}$ and $R^{42}$, $R^{42}$ and $R^{43}$, $R^{43}$ and $R^{44}$, $R^{45}$ and $R^{46}$, $R^{46}$ and $R^{47}$, $R^{47}$ and $R^{48}$, $R^{51}$ and $R^{52}$, $R^{52}$ and $R^{53}$, $R^{53}$ and $R^{54}$, $R^{55}$ and $R^{56}$, $R^{56}$ and $R^{57}$, $R^{57}$ and $R^{58}$, $R^{61}$ and $R^{62}$, $R^{62}$ and $R^{63}$, $R^{63}$ and $R^{64}$, $R^{65}$ and $R^{66}$, $R^{66}$ and $R^{67}$, $R^{67}$ and $R^{68}$, $R^{71}$ and $R^{72}$, $R^{72}$ and $R^{73}$, $R^{73}$ and $R^{74}$, $R^{75}$ and $R^{76}$, $R^{76}$ and $R^{77}$, and $R^{77}$ and $R^{78}$ each may be bonded to each other to form a cyclic structure. The cyclic structure may be an aromatic ring or an aliphatic ring, and may be a structure containing a hetero atom, and the cyclic structure may be a condensed ring containing two or more rings. The hetero atom referred herein is preferably selected from the group consisting of a nitrogen atom, an oxygen atom, and a sulfur atom. Examples of the cyclic structure formed include a benzene ring, a naphthalene ring, a pyridine ring, a pyridazine ring, a pyrimidine ring, a pyrazine ring, a pyrrole ring, an imidazole ring, a pyrazole ring, a triazole ring, an imidazoline ring, an oxazole ring, an isoxazole ring, a thiazole ring, an isothiazole ring, a cyclohexadiene ring, a cyclohexene ring, a cyclopentene ring, a cycloheptatriene ring, a cycloheptadiene ring, and a cycloheptaene ring.

$R^{11}$ to $R^{20}$, $R^{21}$ to $R^{28}$, $R^{31}$ to $R^{38}$, $R^{3a}$, $R^{3b}$, $R^{41}$ to $R^{48}$, $R^{4a}$, $R^{51}$ to $R^{58}$, $R^{61}$ to $R^{68}$, and $R^{71}$ to $R^{78}$ each also preferably independently represent a group represented by any one of the general formulae (2) to (8). $R^{3a}$ and $R^{3b}$ each preferably represent a substituted or unsubstituted alkyl group, and more preferably a substituted or unsubstituted alkyl group having from 1 to 6 carbon atoms. In the case where a substituent is present in the general formulae (2) to (8), the substituent is preferably any of $R^{12}$ to $R^{19}$ for the general formula (2), any of $R^{22}$ to $R^{27}$ for the general formula (3), any of $R^{32}$ to $R^{37}$, $R^{3a}$, and $R^{3b}$, and more preferably at least any of $R^{3a}$, and $R^{3b}$, for the general formula (4), any of $R^{42}$ to $R^{47}$ for the general formula (5), any of $R^{52}$ to $R^{57}$ for the general formula (6), any of $R^{62}$ to $R^{67}$ for the general formula (7), and any of $R^{72}$ to $R^{77}$ for the general formula (8).

Preferred examples of the compound represented by the general formula (1) include a compound, in which $R^1$, $R^3$, and $R^5$ each represent a cyano group, or $R^1$, $R^2$, $R^4$, and $R^5$ each represent a cyano group; and all, the others of $R^1$ to $R^6$ each represent a group represented by the general formula (2) or (3).

Specific examples of the compound represented by the general formula (1) shown below. However, the compound represented by the general formula (1) capable of being used in the invention is not construed as being limited to the specific examples.

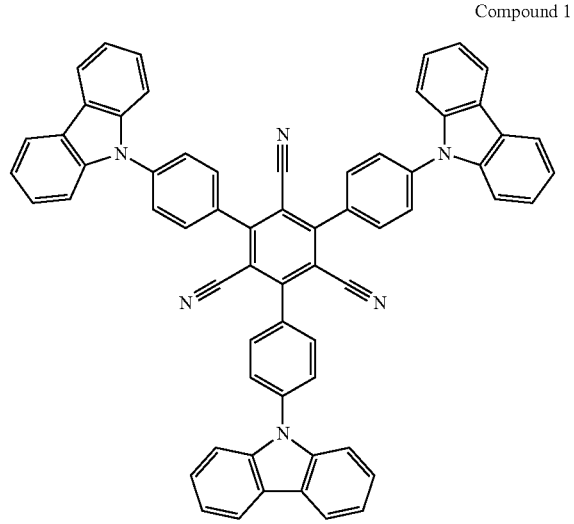

Compound 1

Compound 2

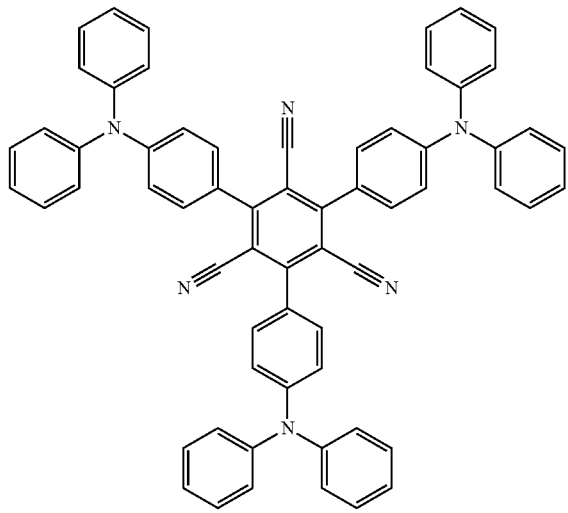

The molecular weight of the compound represented by the general formula (1) is preferably 1,500 or less, more preferably 1,200 or less, further preferably 1,000 or less, and still further preferably 800 or less, for example, in the case where an organic layer containing the compound represented by the general formula (1) is intended to be formed as a film by a vapor deposition method. The lower limit of the molecular weight is the molecular weight of the smallest compound represented by the general formula (1).

The compound represented by the general formula (1) may be formed into a film by a coating method irrespective of the molecular weight thereof. The compound that has a relatively large molecular weight may be formed into a film by a coating method.

As an application of the invention, it may be considered that a compound that contains plural structures each represented by the general formula (1) in the molecule is used as a light-emitting material.

For example, it may be considered that a polymerizable group is introduced in advance to the structure represented by the general formula (1), and a polymer obtained by polymerizing the polymerizable group is used as a light-emitting material. Specifically, it may be considered that a monomer that has a polymerizable functional group at any of $R^2$, $R^3$, $R^4$, and $R^6$ in the general formula (1) is prepared, and is homopolymerized or copolymerized with another monomer to prepare a polymer containing repeating units, and the polymer is used as a light-emitting material. In alternative, it may be considered that the compounds having a structure represented by the general formula (1) are reacted to form a dimer or a trimer, and the dimer or the trimer is used as a light-emitting material.

Examples of the polymer having the repeating unit containing the structure represented by the general formula (1) include a polymer containing a structure represented by the following general formula (9) or (10).

General Formula (9)

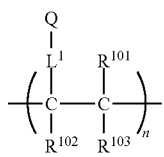

General Formula (10)

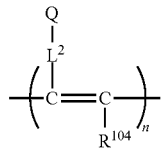

In the general formulae (9) and (10), Q represents a group containing the structure represented by the general formula (1), and $L^1$ and $L^2$ each represent a linking group. The linking group preferably has from 0 to 20 carbon atoms, more preferably from 1 to 15 carbon atoms, and further preferably from 2 to 10 carbon atoms. The linking group preferably has a structure represented by $-X^{11}-L^{11}$, wherein $X^{11}$ represents an oxygen atom or a sulfur atom, and preferably an oxygen atom, and $L^{11}$ represents a linking group, preferably a substituted or unsubstituted alkylene group or a substituted or unsubstituted arylene group, and more preferably a substituted or unsubstituted alkylene group having from 1 to 10 carbon atoms or a substituted or unsubstituted phenylene group.

In the general formulae (9) and (10), $R^{101}$, $R^{102}$, $R^{103}$ and $R^{104}$ each independently represent a substituent, preferably a substituted or unsubstituted alkyl group having from 1 to 6 carbon atoms, a substituted or unsubstituted alkoxy group having from 1 to 6 carbon atoms, or a halogen atom, more preferably an unsubstituted alkyl group having from 1 to 3 carbon atoms, an unsubstituted alkoxy group having from 1 to 3 carbon atoms, a fluorine atom or a chlorine atom, and further preferably an unsubstituted alkyl group having from 1 to 3 carbon atoms or an unsubstituted alkoxy group having from 1 to 3 carbon atoms.

The linking group represented by $L^1$ and $L^2$ may be bonded to any of $R^2$, $R^3$, $R^4$, and $R^6$ on the structure of the general formula (1), any of $R^{11}$ to $R^{20}$ of the structure of the general formula (2), any of $R^{21}$ to $R^{28}$ of the structure of the general formula (3), any of $R^{31}$ to $R^{38}$, $R^{3a}$, and $R^{3b}$ of the structure of the general formula (4), any of $R^{41}$ to $R^{48}$ and $R^{4a}$ of the structure of the general formula (5), any of $R^{51}$ to $R^{58}$ of the structure of the general formula (6), any of $R^{61}$ to $R^{68}$ of the structure of the general formula (7), and any of $R^{71}$ to $R^{78}$ of the structure of the general formula (8), constituting Q. Two or more of the linking groups may be boded to one group represented by Q to form a crosslinked structure or a network structure.

Specific examples of the structure of the repeating unit include structures represented by the following formulae (11) to (14).

Formula (11)

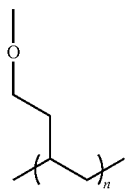

Formula (12)

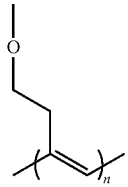

Formula (13)

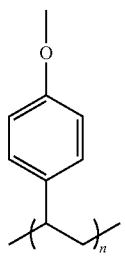

Formula (14)

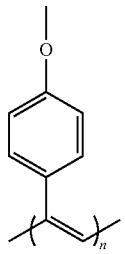

The polymer having the repeating unit containing the structure represented by any of the formulae (11) to (14) may be synthesized in such a manner that a hydroxyl group is introduced to any of $R^2$, $R^3$, $R^4$, and $R^6$ in the structure represented by the general formula (1), and the hydroxyl group as a linker is reacted with the following compound to introduce a polymerizable group there to, followed by polymerizing the polymerizable group.

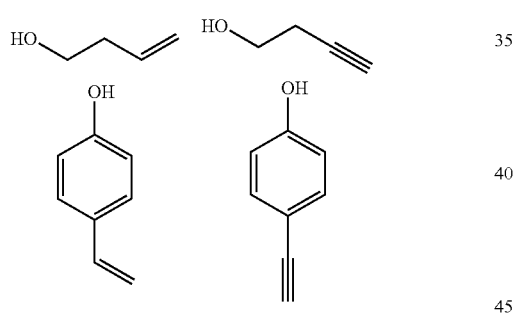

The polymer containing the structure represented by the general formula (1) in the molecule may be a polymer containing only a repeating unit having the structure represented by the general formula (1), or a polymer further containing a repeating unit having another structure. The repeating unit having the structure represented by the general formula (1) contained in the polymer may be only one kind or two or more kinds. Examples of the repeating unit that does not have the structure represented by the general formula (1) include a repeating unit derived from a monomer that is used for ordinary copolymerization. Examples of the repeating unit include a repeating unit derived from a monomer having an ethylenic unsaturated bond, such as ethylene and styrene.

Compound Represented by General Formula (1)

The compound represented by the general formula (1') is a novel compound.

General Formula (1')

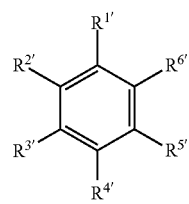

In the general formula (1'), $R^{1'}$, $R^{3'}$, and $R^{5'}$ each represent a cyano group, or $R^{1'}$, $R^{2'}$, $R^{4'}$, and $R^{5'}$ each represent a cyano group; and the others of $R^{1'}$ to $R^{6'}$ each independently represent a group represented by any one of the following general formulae (2') to (8').

General Formula (2')

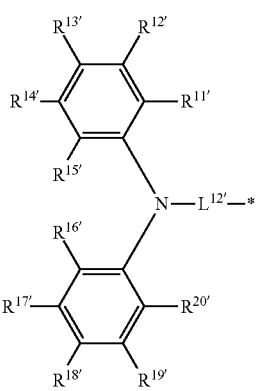

General Formula (3')

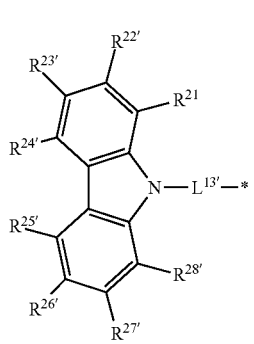

General Formula (4')

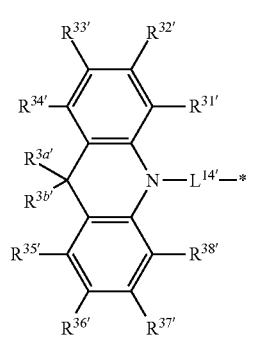

-continued

General Formula (5')

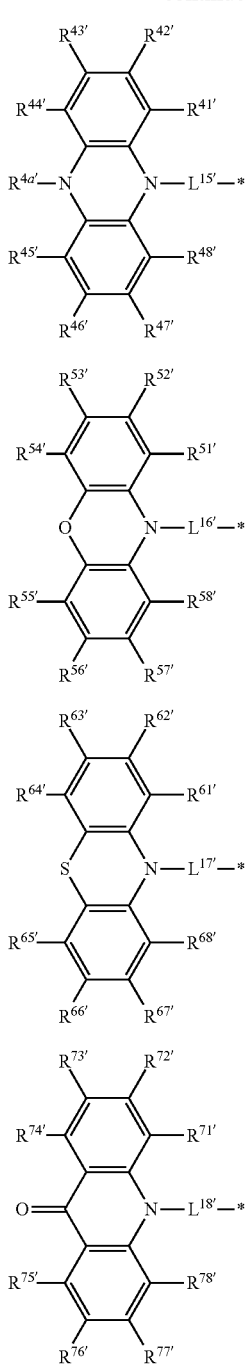

General Formula (6')

General Formula (7')

General Formula (8')

In the general formulae (2') to (8'), $L^{12\prime}$ to $L^{18\prime}$ each represent a single bond or a substituted or unsubstituted arylene group; * represents a position bonded to the benzene ring in the general formula (1'); and $R^{11\prime}$ to $R^{20\prime}$, $R^{21\prime}$ to $R^{28\prime}$, $R^{31\prime}$ to $R^{38\prime}$ $R^{3a\prime}$ $R^{3b\prime}$, $R^{41\prime}$ to $R^{48\prime}$, $R^{4a\prime}$, $R^{51\prime}$ to $R^{58\prime}$, $R^{61\prime}$ to $R^{68\prime}$, and $R^{71\prime}$ to $R^{78\prime}$ each independently represent a hydrogen atom or a substituent, provided that $R^{11\prime}$ and $R^{12\prime}$, $R^{12\prime}$ and $R^{13\prime}$, $R^{13\prime}$ and $R^{14\prime}$, $R^{14\prime}$ and $R^{15\prime}$, $R^{16\prime}$ and $R^{17\prime}$, $R^{17\prime}$ and $R^{18\prime}$, $R^{18\prime}$ and $R^{19\prime}$, $R^{19\prime}$ and $R^{20\prime}$, $R^{21\prime}$ and $R^{22\prime}$, $R^{22\prime}$ and $R^{23\prime}$, $R^{23\prime}$ and $R^{24\prime}$, $R^{24\prime}$ and $R^{25\prime}$, $R^{25\prime}$ and $R^{26\prime}$, $R^{26\prime}$ and $R^{27\prime}$, $R^{27\prime}$ and $R^{28\prime}$, $R^{31\prime}$ and $R^{32\prime}$, $R^{32\prime}$ and $R^{33\prime}$, $R^{33\prime}$ and $R^{34\prime}$, $R^{35\prime}$ and $R^{36\prime}$, $R^{36\prime}$ and $R^{37\prime}$, $R^{37\prime}$ and $R^{38\prime}$, $R^{3a\prime}$ and $R^{3b\prime}$, $R^{41\prime}$ and $R^{42\prime}$, $R^{42\prime}$ and $R^{43\prime}$, $R^{43\prime}$ and $R^{44\prime}$, $R^{45\prime}$, and $R^{46\prime}$, $R^{46\prime}$ and $R^{47\prime}$, $R^{47\prime}$ and $R^{48\prime}$, $R^{51\prime}$ and $R^{52\prime}$, $R^{52\prime}$ and $R^{53\prime}$, $R^{53\prime}$ and $R^{54\prime}$, $R^{55\prime}$ and $R^{56\prime}$, $R^{56\prime}$ and $R^{57\prime}$, $R^{57\prime}$ and $R^{58\prime}$, $R^{61\prime}$ and $R^{62\prime}$, $R^{62\prime}$ and $R^{63\prime}$, $R^{63\prime}$ and $R^{64\prime}$, $R^{65\prime}$ and $R^{66\prime}$, $R^{66\prime}$ and $R^{67\prime}$, $R^{67\prime}$ and $R^{68\prime}$, $R^{71\prime}$ and $R^{72\prime}$, $R^{72\prime}$ and $R^{73\prime}$, $R^{73\prime}$ and $R^{74\prime}$, $R^{75\prime}$ and $R^{76\prime}$, $R^{76\prime}$ and $R^{77\prime}$, and $R^{77\prime}$ and $R^{78\prime}$ each may be bonded to each other to form a cyclic structure.

For the descriptions and the preferred ranges of $R^{1\prime}$ to $R^{6\prime}$ in the general formula (1'), and $L^{12\prime}$ to $R^{18\prime}$, *, $R^{11\prime}$ to $R^{20\prime}$, $R^{21\prime}$ to $R^{28\prime}$, $R^{31\prime}$ to $R^{38\prime}$, $R^{3a\prime}$, $R^{3b\prime}$, $R^{41\prime}$ to $R^{48\prime}$, $R^{4a\prime}$, $R^{51\prime}$ to $R^{58\prime}$, $R^{61\prime}$ to $R^{68\prime}$, and $R^{71\prime}$ to $R^{78\prime}$ of the general formulae (2') to (8'), reference may be made to the descriptions of the compound represented by the general formula (1).

Synthesis Method of Compound Represented by General Formula (1')

The compound represented by the general formula (1') may be synthesized by combining the known reactions. For example, a compound represented by the general formula (1'), in which $R^{1\prime}$, $R^{3\prime}$, and $R^{5\prime}$ each represent a cyano group, $R^{2\prime}$, $R^{4\prime}$, and $R^{6\prime}$ each represent a group represented by the general formula (4'), and $L^{16\prime}$ represents a 1,4-phenylene group, can be synthesized reacting the following two compounds.

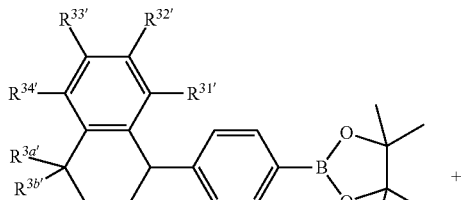

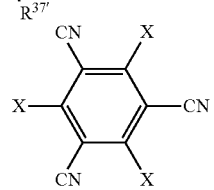

In the aforementioned reaction formula, for the descriptions of $R^{31\prime}$ to $R^{38\prime}$, $R^{3a\prime}$, and $R^{3b\prime}$, reference may be made to the corresponding descriptions in the general formula (1'). X represents a halogen atom, examples of which include a fluorine atom, a chlorine atom, a bromine atom, and an iodine atom, and a chlorine atom, a bromine atom, and an iodine atom are preferred, with a bromine atom being more preferred.

The reactions in the aforementioned scheme each are an application of the known reactions, and the known reaction conditions may be appropriately selected and used. For the details of the reactions, reference may be made to the synthesis examples described later. The compound represented by the general formula (1') may also be synthesized by combining the other known synthesis reactions.

Organic Light-Emitting Device

The compound represented by the general formula (1) of the invention is useful as a light-emitting material of an organic light-emitting device. Accordingly, the compound represented by the general formula (1) of the invention may be effectively used as a light-emitting material in a light-emitting layer of an organic light-emitting device. The compound represented by the general formula (1) includes a delayed fluorescent material emitting delayed fluorescent light (delayed fluorescence emitter). Thus, the invention provides an invention relating to a delayed fluorescence emitter having the structure represented by the general formula (1), an invention relating to the use of the compound represented by the general formula (1) as the delayed fluorescence emitter, and an invention relating to a method for emitting delayed fluorescent light with the compound represented by the general formula (1). An organic light-emitting device that uses the compound as a light-emitting material has features that the device emits delayed fluorescent light and has a high light emission efficiency. The principle of the features may be described as follows for an organic electroluminescent device as an example.

In an organic electroluminescent device, carriers are injected from an anode and a cathode to a light-emitting material to form an excited state for the light-emitting material, with which light is emitted. In the case of a carrier injection type organic electroluminescent device, in general, excitons that are excited to the excited singlet state are 25% of the total excitons generated, and the remaining 75% thereof are excited to the excited triplet state. Accordingly, the use of phosphorescence, which is light emission from the excited triplet state, provides a high energy utilization. However, the excited triplet state has a long lifetime and thus causes saturation of the excited state and deactivation of energy through mutual action with the excitons in the excited triplet state, and therefore the quantum yield of phosphorescence may generally be often not high. A delayed fluorescent material emits fluorescent light through the mechanism that the energy of excitons transits to the excited triplet state through intersystem crossing or the like, and then transits to the excited singlet state through reverse intersystem crossing due to triplet-triplet annihilation or absorption of thermal energy, thereby emitting fluorescent light. It is considered that among the materials, a thermal activation type delayed fluorescent material emitting light through absorption of thermal energy is particularly useful for an organic electroluminescent device. In the case where a delayed fluorescent material is use in an organic electroluminescent device, the excitons in the excited singlet state normally emit fluorescent light. On the other hand, the excitons in the excited triplet state emit fluorescent light through intersystem crossing to the excited singlet state by absorbing the heat generated by the device. At this time, the light emitted through reverse intersystem crossing from the excited triplet state to the excited singlet state has the same wavelength as fluorescent light since it is light emission from the excited singlet state, but has a longer lifetime (light emission lifetime) than the normal fluorescent light and phosphorescent light, and thus the light is observed as fluorescent light that is delayed from the normal fluorescent light and phosphorescent light. The light may be defined as delayed fluorescent light. The use of the thermal activation type exciton transition mechanism may raise the proportion of the compound in the excited singlet state, which is generally formed in a proportion only of 25%, to 25% or more through the absorption of the thermal energy after the carrier injection. A compound that emits strong fluorescent light and delayed fluorescent light at a low temperature of lower than 100° C. undergoes the intersystem crossing from the excited triplet state to the excited singlet state sufficiently with the heat of the device, thereby emitting delayed fluorescent light, and thus the use of the compound may drastically enhance the light emission efficiency.

The compound represented by the general formula (1) of the invention has a tendency that on forming into a film as a light-emitting layer, the compound shows good orientation with respect to the film forming surface. The excellent orientation of the compound with respect to the film forming surface provides an advantage that the propagation directions of light emitted by the compound are aligned to enhance the light extraction efficiency from the light-emitting layer.

The use of the compound represented by the general formula (1) of the invention as a light-emitting material of a light-emitting layer may provide an excellent organic light-emitting device, such as an organic photoluminescent device (organic PL device) and an organic electroluminescent device (organic EL device). At this time, the compound represented by the general formula (1) of the invention may have a function of assisting light emission of another light-emitting material contained in the light-emitting layer, i.e., as a so-called assist dopant. Specifically, the compound represented by the general formula (1) of the invention contained in the light-emitting layer may have a lowest excited singlet energy level that is between the lowest excited singlet energy level of the host material contained in the light-emitting layer and the lowest excited singlet energy level of the another light-emitting material contained in the light-emitting layer.

The organic photoluminescent device has a structure containing a substrate having formed thereon at least a light-emitting layer. The organic electroluminescent device has a structure containing at least an anode, a cathode and an organic layer formed between the anode and the cathode. The organic layer contains at least a light-emitting layer, and may be formed only of a light-emitting layer, or may have one or more organic layer in addition to the light-emitting layer. Examples of the organic layer include a hole transporting layer, a hole injection layer, an electron barrier layer, a hole barrier layer, an electron injection layer, an electron transporting layer and an exciton barrier layer. The hole transporting layer may be a hole injection and transporting layer having a hole injection function, and the electron transporting layer may be an electron injection and transporting layer having an electron injection function. A specific structural example of an organic electroluminescent device is shown in FIG. 1. In FIG. 1, the numeral 1 denotes a substrate, 2 denotes an anode, 3 denotes a hole injection layer, 4 denotes a hole transporting layer, 5 denotes a light-emitting layer, 6 denotes an electron transporting layer, and 7 denotes a cathode.

The members and the layers of the organic electroluminescent device will be described below. The descriptions for the substrate and the light-emitting layer may also be applied to the substrate and the light-emitting layer of the organic photoluminescent device.

Substrate

The organic electroluminescent device of the invention is preferably supported by a substrate. The substrate is not particularly limited and may be those that have been commonly used in an organic electroluminescent device, and examples thereof used include those formed of glass, transparent plastics, quartz and silicon.

Anode

The anode of the organic electroluminescent device used is preferably formed of as an electrode material include a metal, an alloy or an electroconductive compound each having a large work function (4 eV or more), or a mixture thereof. Specific examples of the electrode material include a metal, such as Au, and an electroconductive transparent material, such as CuI, indium tin oxide (ITO), $SnO_2$ and ZnO. A material that is amorphous and is capable of forming a transparent electroconductive film, such as IDIXO ($In_2O_3$—ZnO), may also be used. The anode may be formed in such a manner that the electrode material is formed into a thin film by such a method as vapor deposition or sputtering, and the film is patterned into a desired pattern by a photolithography method, or in the case where the pattern may not require high accuracy (for example, approximately 100 μm or more), the pattern may be formed with a mask having a desired shape on vapor deposition or sputtering of the electrode material. In alternative, in the case where a material capable of being applied as a coating, such as an organic electroconductive compound, is used, a wet film forming method, such as a printing method and a coating method, may be used. In the case where emitted light is to be taken out through the anode, the anode preferably has a transmittance of more than 10%, and the anode preferably has a sheet resistance of several hundred Ohm per square or less. The thickness thereof may be generally selected from a range of from 10 to 1,000 nm, and preferably from 10 to 200 nm, while depending on the material used.

Cathode

The cathode is preferably formed of as an electrode material including a metal having a small work function (4 eV or less) (referred to as an electron injection metal), an alloy or an electroconductive compound, or a mixture thereof. Specific examples of the electrode material include sodium, a sodium-potassium alloy, magnesium, lithium, a magnesium-copper mixture, a magnesium-silver mixture, a magnesium-aluminum mixture, a magnesium-indium mixture, an aluminum-aluminum oxide ($Al_2O_3$) mixture, indium, a lithium-aluminum mixture, and a rare earth metal. Among these, a mixture of an electron injection metal and a second metal that is a stable metal having a larger work function than the electron injection metal, for example, a magnesium-silver mixture, a magnesium-aluminum mixture, a magnesium-indium mixture, an aluminum-aluminum oxide ($Al_2O_3$) mixture, a lithium-aluminum mixture, and aluminum, are preferred from the standpoint of the electron injection property and the durability against oxidation and the like. The cathode may be produced by forming the electrode material into a thin film by such a method as vapor deposition or sputtering. The cathode preferably has a sheet resistance of several hundred Ohm per square or less, and the thickness thereof may be generally selected from a range of from 10 nm to 5 μm, and preferably from 50 to 200 nm. For transmitting the emitted light, any one of the anode and the cathode of the organic electroluminescent device is preferably transparent or translucent, thereby enhancing the light emission luminance.

The cathode may be formed with the electroconductive transparent materials described for the anode, thereby forming a transparent or translucent cathode, and by applying the cathode, a device having an anode and a cathode, both of which have transmittance, may be produced.

Light-Emitting Layer

The light-emitting layer is a layer, in which holes and electrons injected from the anode and the cathode, respectively, are recombined to form excitons, and then the layer emits light. A light-emitting material may be solely used as the light-emitting layer, but the light-emitting layer preferably contains a light-emitting material and a host material. The light-emitting material used may be one kind or two or more kinds selected from the group of compounds represented by the general formula (1) of the invention. In order that the organic electroluminescent device and the organic photoluminescent device of the invention exhibit a high light emission efficiency, it is important that the singlet excitons and the triplet excitons generated in the light-emitting material are confined in the light-emitting material. Accordingly, a host material is preferably used in addition to the light-emitting material in the light-emitting layer. The host material used may be an organic compound that has excited singlet energy and excited triplet energy, at least one of which is higher than those of the light-emitting material of the invention. As a result, the singlet excitons and the triplet excitons generated in the light-emitting material of the invention are capable of being confined in the molecules of the light-emitting material of the invention, thereby eliciting the light emission efficiency thereof sufficiently. Even though the singlet excitons and the triplet excitons are not confined sufficiently, a high light emission efficiency may be obtained in some cases, and thus a host material that is capable of achieving a high light emission efficiency may be used in the invention without any particular limitation. In the organic light-emitting device and the organic electroluminescent device of the invention, the light emission occurs in the light-emitting material of the invention contained in the light-emitting layer. The emitted light contains both fluorescent light and delayed fluorescent light. However, a part of the emitted light may contain emitted light from the host material, or the emitted light may partially contain emitted light from the host material.

In the case where the host material is used, the amount of the compound of the invention as the light-emitting material contained in the light-emitting layer is preferably 0.1% by weight or more, and more preferably 1% by weight or more, and is preferably 50% by weight or less, more preferably 20% by weight or less, and further preferably 10% by weight or less.

The host material in the light-emitting layer is preferably an organic compound that has a hole transporting function and an electron transporting function, prevents the emitted light from being increased in wavelength, and has a high glass transition temperature.

Injection Layer

The injection layer is a layer that is provided between the electrode and the organic layer, for decreasing the driving voltage and enhancing the light emission luminance, and includes a hole injection layer and an electron injection layer, which may be provided between the anode and the light-emitting layer or the hole transporting layer and between the cathode and the light-emitting layer or the electron transporting layer. The injection layer may be provided depending on necessity.

Barrier Layer

The barrier layer is a layer that is capable of inhibiting charges (electrons or holes) and/or excitons present in the light-emitting layer from being diffused outside the light-emitting layer. The electron barrier layer may be disposed between the light-emitting layer and the hole transporting layer, and inhibits electrons from passing through the light-emitting layer toward the hole transporting layer. Similarly, the hole barrier layer may be disposed between the light-emitting layer and the electron transporting layer, and inhibits holes from passing through the light-emitting layer toward the electron transporting layer. The barrier layer may also be used for inhibiting excitons from being diffused outside the light-emitting layer. Thus, the electron barrier layer and the hole barrier layer each may also have a function as an exciton barrier layer. The term "the electron barrier layer" or "the exciton barrier layer" referred herein is intended to include a layer that has both the functions of an electron barrier layer and an exciton barrier layer by one layer.

Hole Barrier Layer

The hole barrier layer has the function of an electron transporting layer in a broad sense. The hole barrier layer has a function of inhibiting holes from reaching the electron transporting layer while transporting electrons, and thereby enhances the recombination probability of electrons and holes in the light-emitting layer. As the material for the hole barrier layer, the materials for the electron transporting layer described later may be used depending on necessity.

Electron Barrier Layer

The electron barrier layer has the function of transporting holes in a broad sense. The electron barrier layer has a function of inhibiting electrons from reaching the hole transporting layer while transporting holes, and thereby enhances the recombination probability of electrons and holes in the light-emitting layer.

Exciton Barrier Layer

The exciton barrier layer is a layer for inhibiting excitons generated through recombination of holes electrons in the light-emitting layer from being diffused to the charge transporting layer, and the use of the layer inserted enables effective confinement of excitons in the light-emitting layer, and thereby enhances the light emission efficiency of the device. The exciton barrier layer may be inserted adjacent to the light-emitting layer on any of the side of the anode and the side of the cathode, and on both the sides. Specifically, in the case where the exciton, barrier layer is present on the side of the anode, the layer may be inserted between the hole transporting layer and the light-emitting layer and adjacent to the light-emitting layer, and in the case where the layer is inserted on the side of the cathode, the layer may be inserted between the light-emitting layer and the cathode and adjacent to the light-emitting layer. Between the anode and the excitons barrier layer that is adjacent to the light-emitting layer on the side of the anode, a hole injection layer, an electron barrier layer and the like may be provided, and between the cathode and the exciton barrier layer that is adjacent to the light-emitting layer on the side of the cathode, an electron injection layer, an electron transporting layer, a hole barrier layer and the like may be provided. In the case where the barrier layer is provided, the material used for the barrier layer preferably has excited singlet energy and excited triplet energy, at least one of which is higher than the excited singlet energy and the excited triplet energy of the light-emitting material, respectively.

Role Transporting Layer

The hole transporting layer is formed of a hole transporting material having a function of transporting holes, and the hole transporting layer may be provided as a single layer or plural layers.

The hole transporting material has one of injection or transporting property of holes and barrier property of electrons, and may be any of an organic material and an inorganic material. Examples of known hole transporting materials that may be used herein include a triazole derivative, an oxadiazole derivative, an imidazole derivative, a carbazole derivative, an indolocarbazole derivative, a polyarylalkane derivative, a pyrazoline derivative, a pyrazolone derivative, a phenylenediamine derivative, an arylamine derivative, an amino-substituted chalcone derivative, an oxazole derivative, a styrylanthracene derivative, a fluorenone derivative, a hydrazone derivative, a stilbene derivative, a silazane derivative, an aniline copolymer and an electroconductive polymer oligomer, particularly a thiophene oligomer. Among these, a porphyrin compound, an aromatic tertiary amine compound and a styrylamine compound are preferably used, and an aromatic tertiary amine compound is more preferably used.

Electron Transporting Layer

The electron transporting layer is formed of a material having a function of transporting electrons, and the electron transporting layer may be provided as a single layer or plural layers.

The electron transporting material (which may also function as a hole barrier material in some cases) needs only to have a function of transporting electrons, which are injected from the cathode, to the light-emitting layer. Examples of the electron transporting layer that may be used herein include a nitro-substituted fluorene derivative, a diphenylquinone derivative, a thiopyran dioxide derivative, carbodiimide, a fluorenylidene methane derivative, anthraquinodimethane and anthrone derivatives, and an oxadiazole derivative. The electron transporting material, used may be a thiadiazole derivative obtained by replacing the oxygen atom of the oxadiazole ring of the oxadiazole derivative by a sulfur atom, or a quinoxaline derivative having a quinoxaline ring, which is known as an electron attracting group. Furthermore, polymer materials having these materials introduced to the polymer chain or having these materials used as the main chain, of the polymer may also be used.

In the production of the organic electroluminescent device, the compound represented by the general formula (1) may be used not only in the light-emitting layer but also in the other layers than the light-emitting layer. In this case, the compound represented by the general formula (1) used in the light-emitting layer and the compound represented by the general formula (1) used in the other layers than the light-emitting layer may be the same as or different from each other. For example, the compound represented by the general formula. (1) may be used in the injection layer, the barrier layer, the hole barrier layer, the electron barrier layer, the exciton barrier layer, the hole transporting layer, the electron transporting layer and the like described above. The film forming method of the layers are not particularly limited, and the layers may be produced by any of a dry process and a wet process.

Specific examples of preferred materials that may be used in the organic electroluminescent device are shown below, but the materials that may be used in the invention are not construed as being limited to the example compounds. The compound that is shown as a material having a particular function may also be used as a material having another function. In the structural formulae of the example compounds, R and $R_1$ to $R_{10}$ each independently represent a hydrogen atom or a substituent, and n represents an integer of from 3 to 5.

Preferred examples of a compound that may also be used as the host material of the light-emitting layer are shown below.

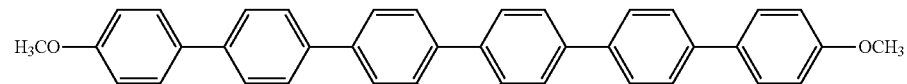
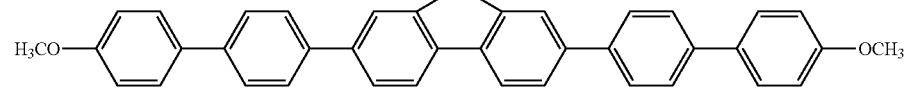
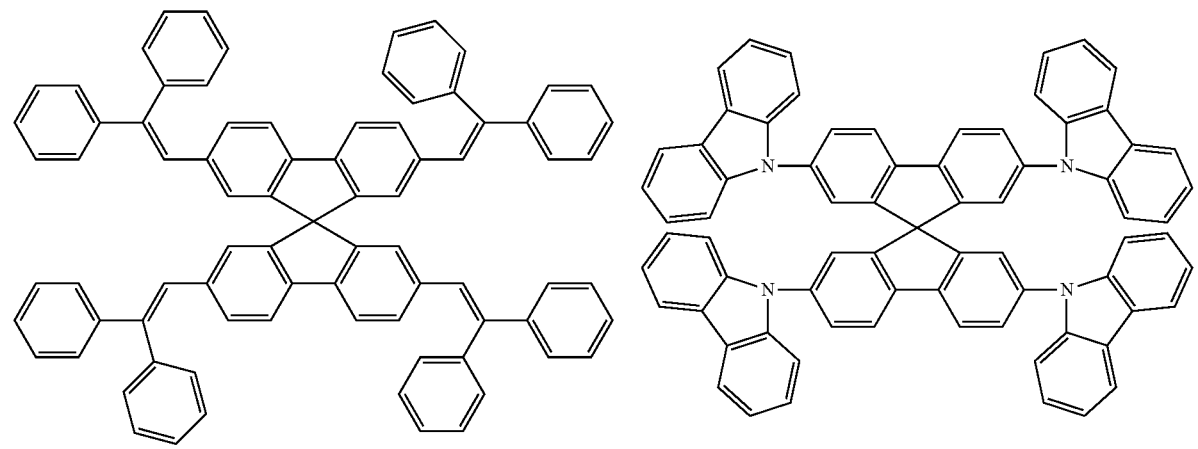
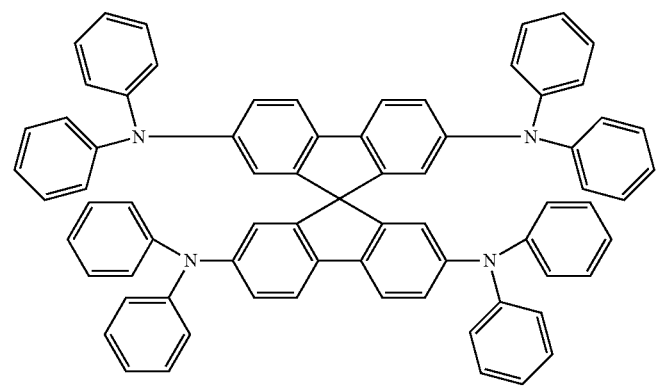
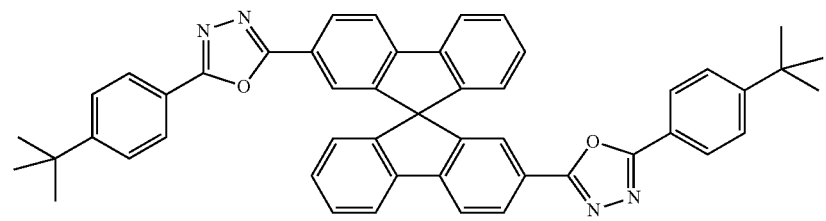
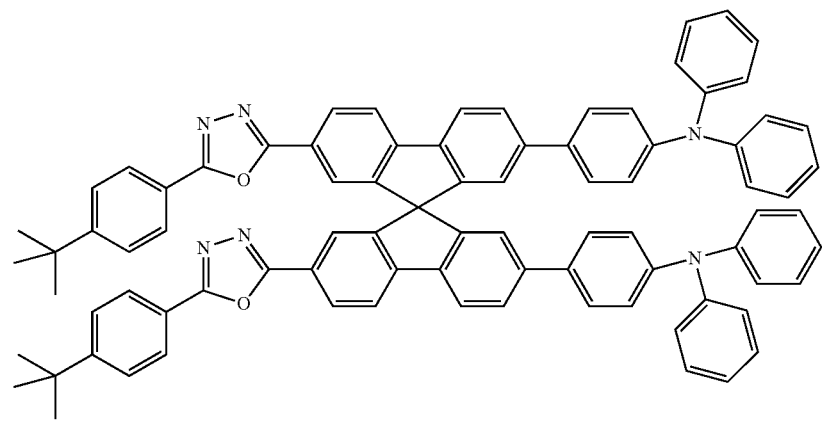

-continued
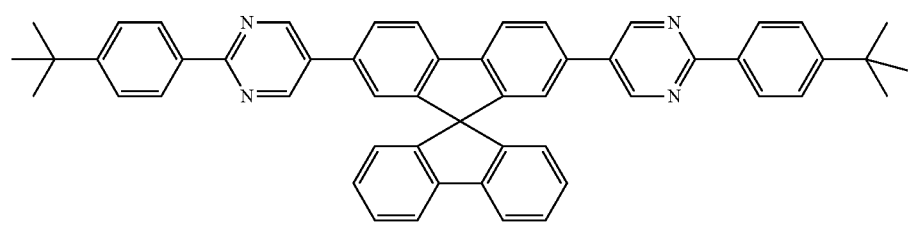
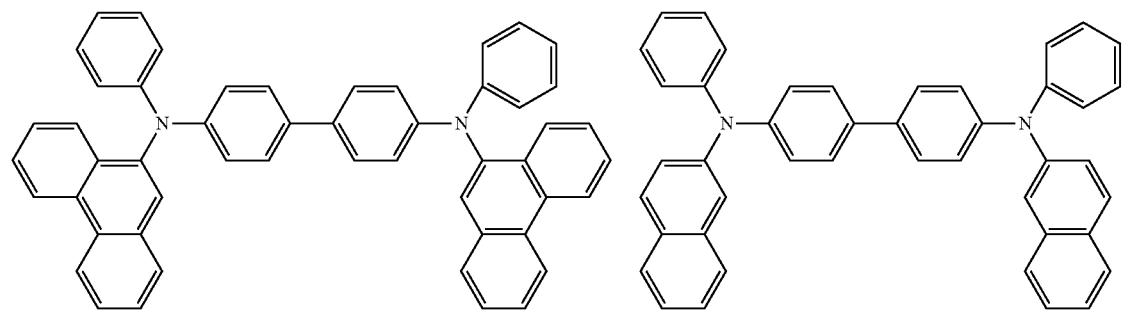
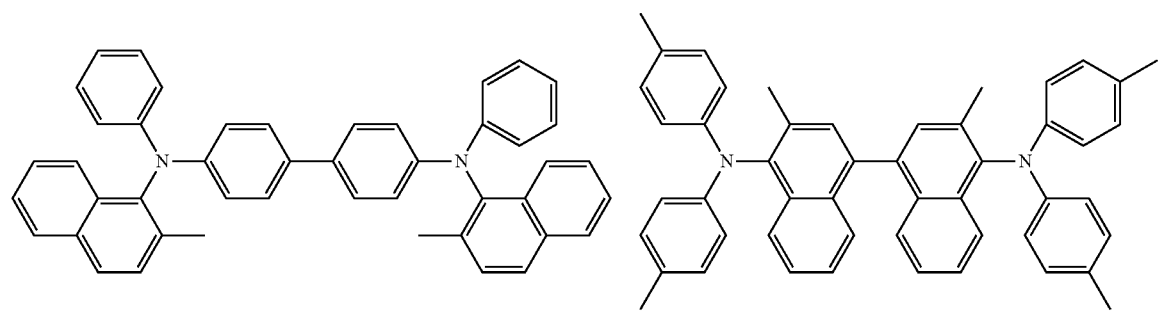
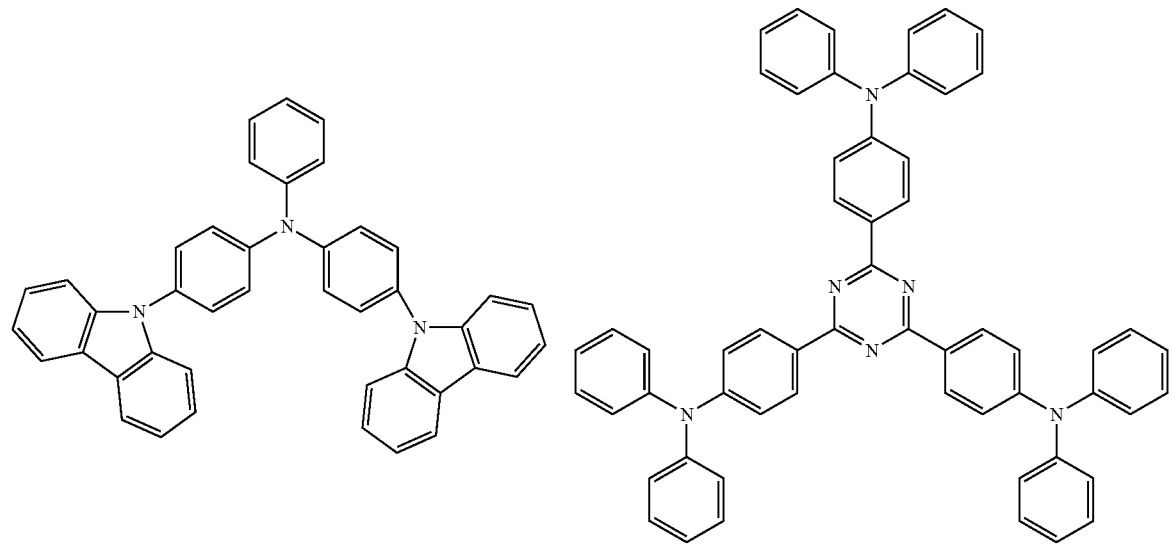

-continued
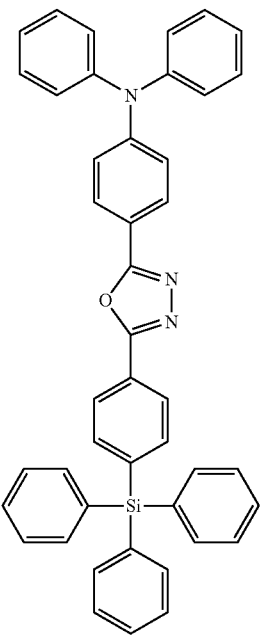
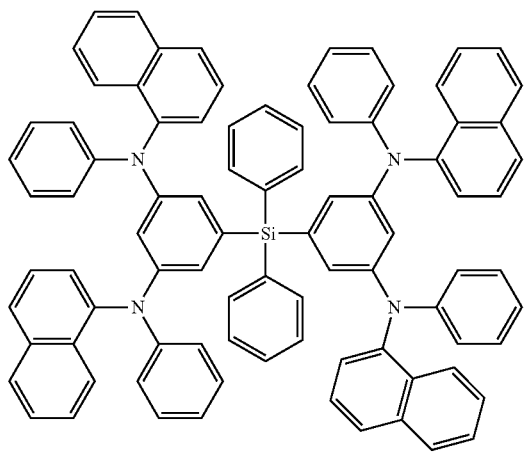
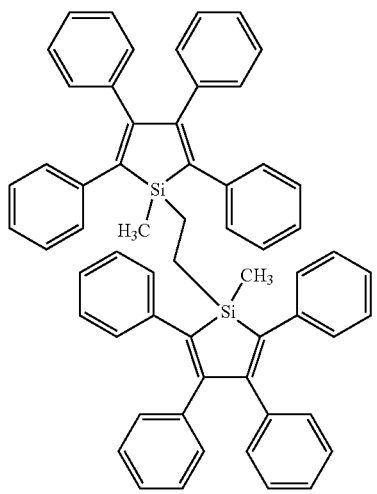
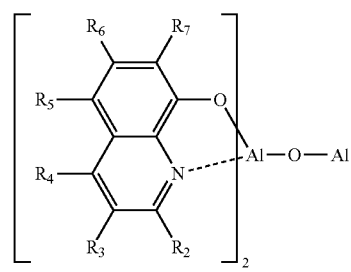
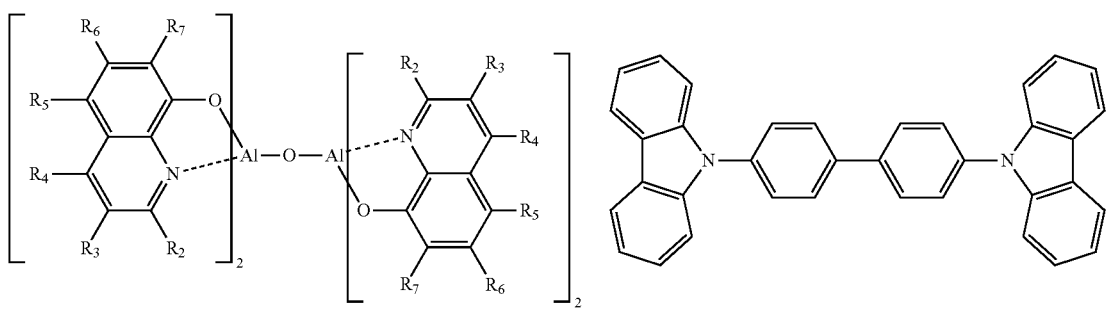
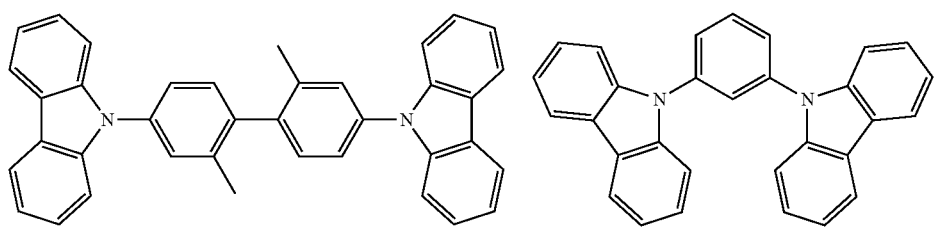

-continued
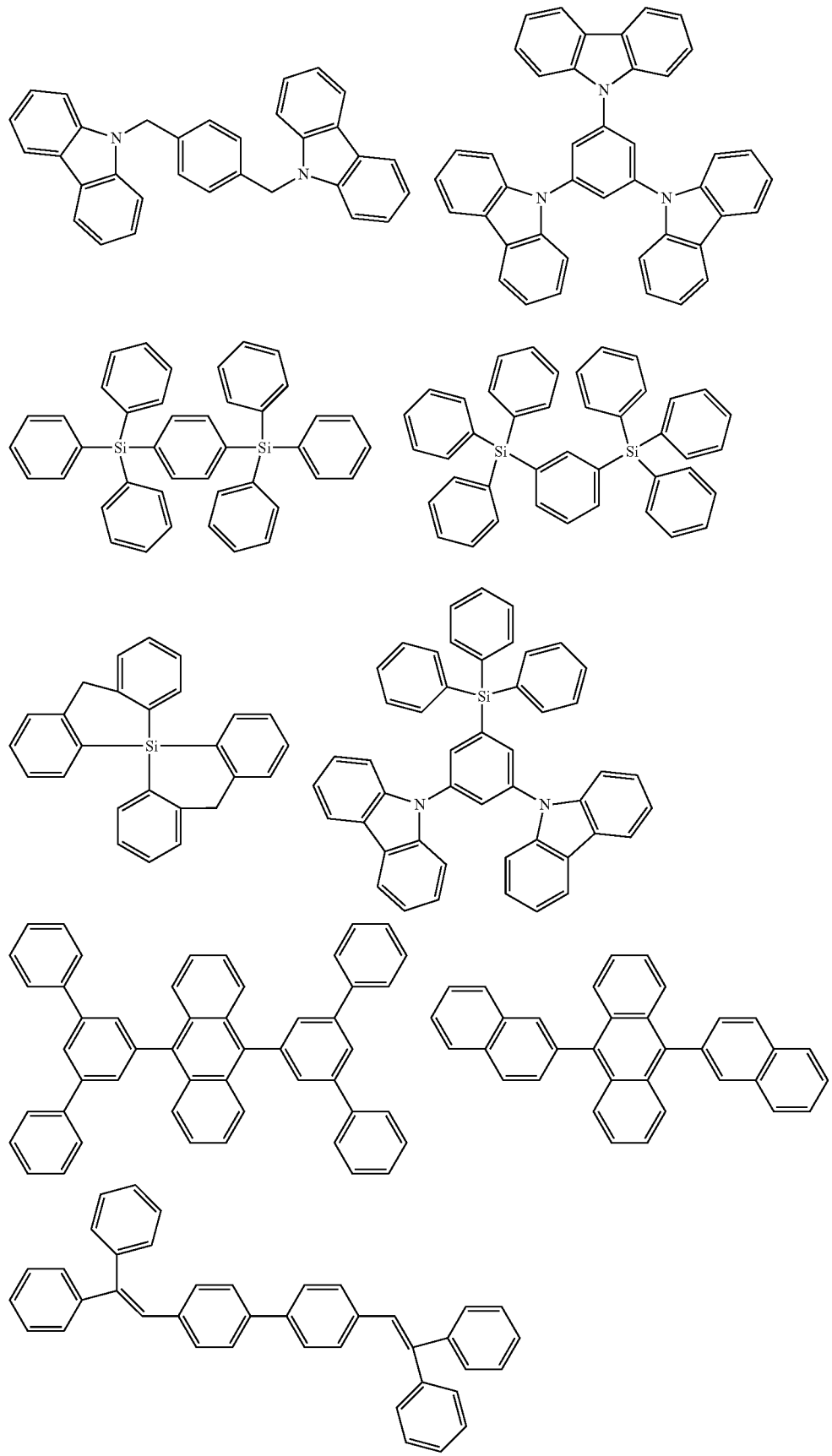

-continued
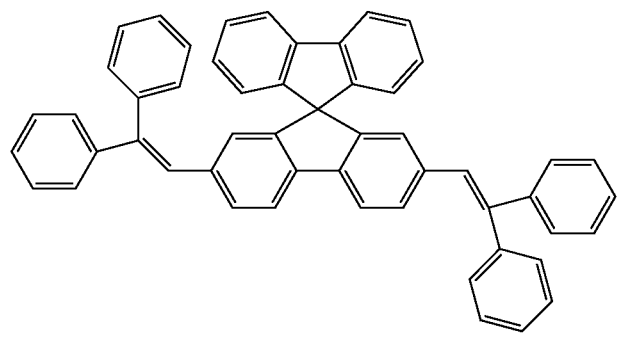
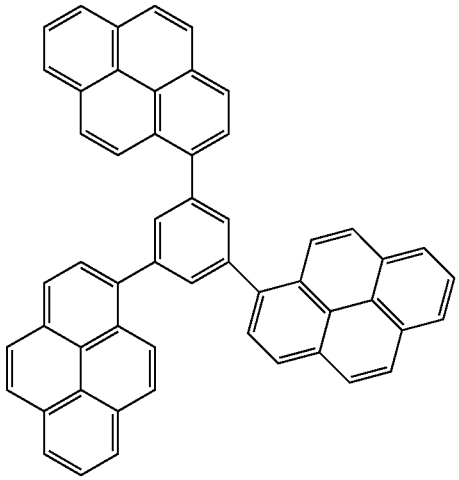
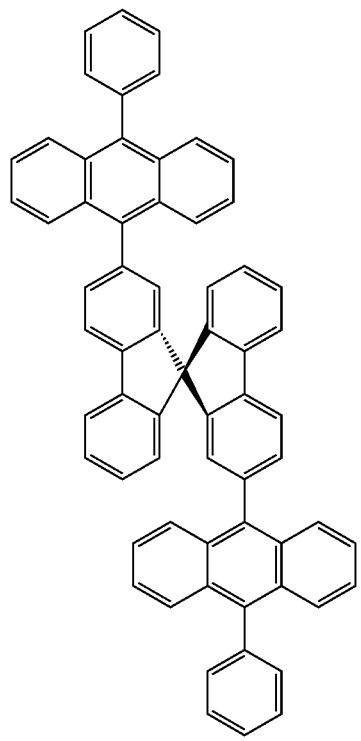
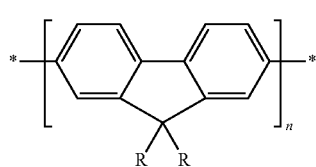
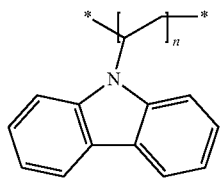
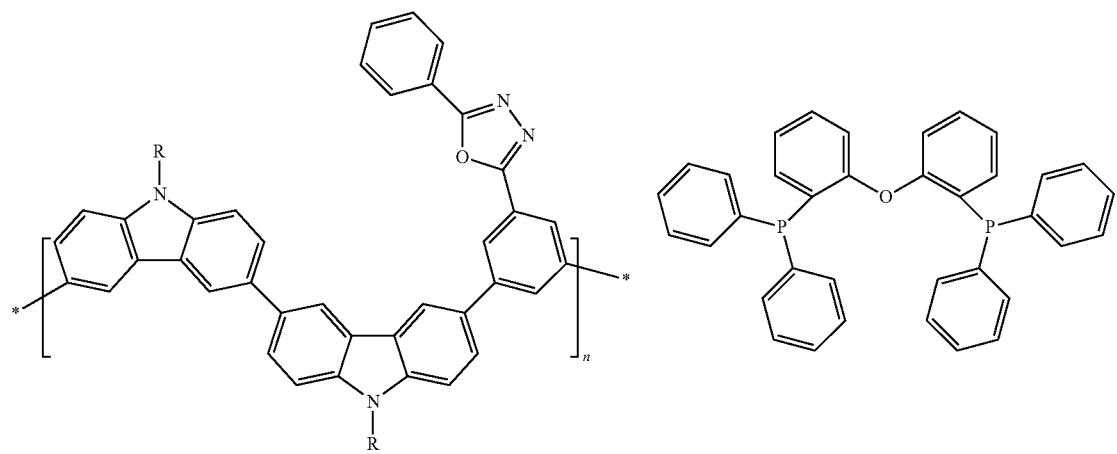

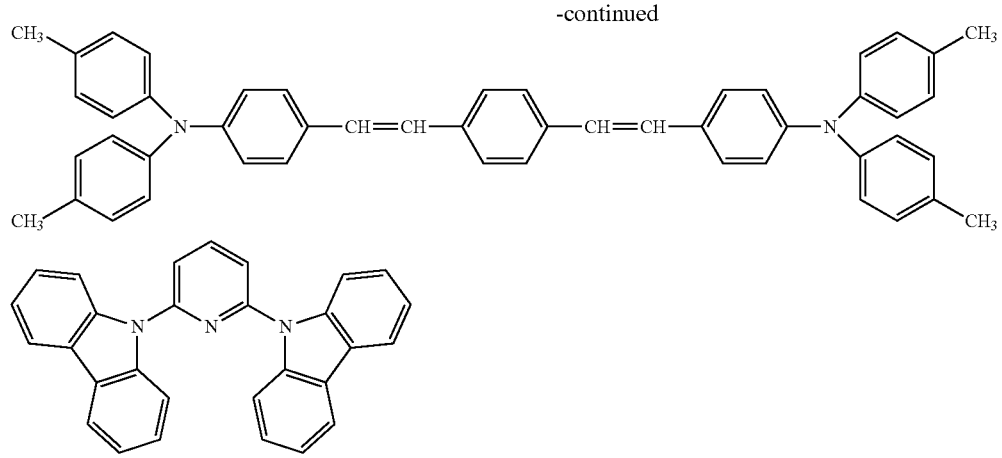
Preferred examples of a compound that may be used as the hole injection material are shown below.
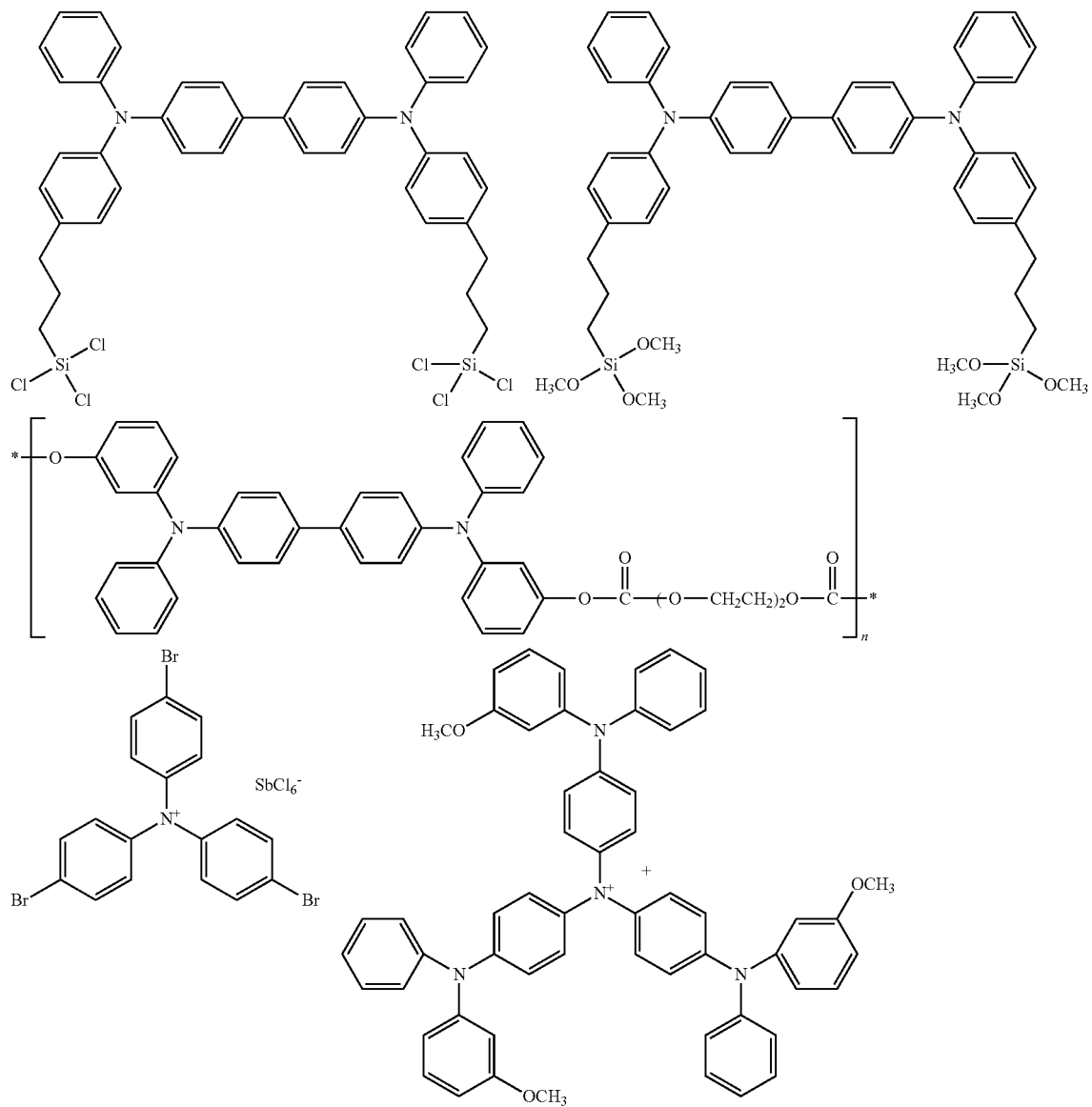

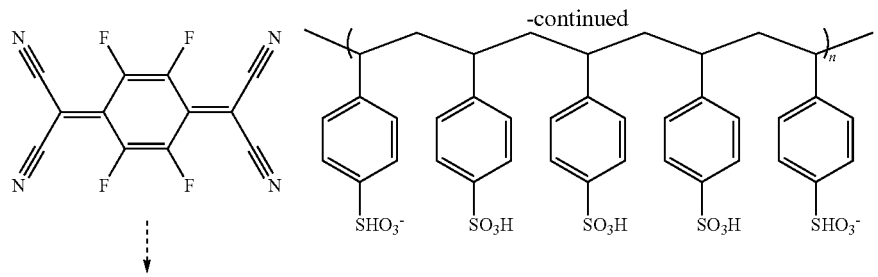
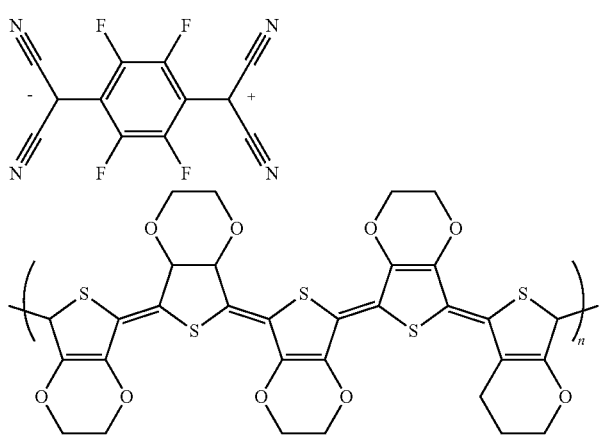
Preferred examples of a compound that may be used as the hole transporting material are shown below.
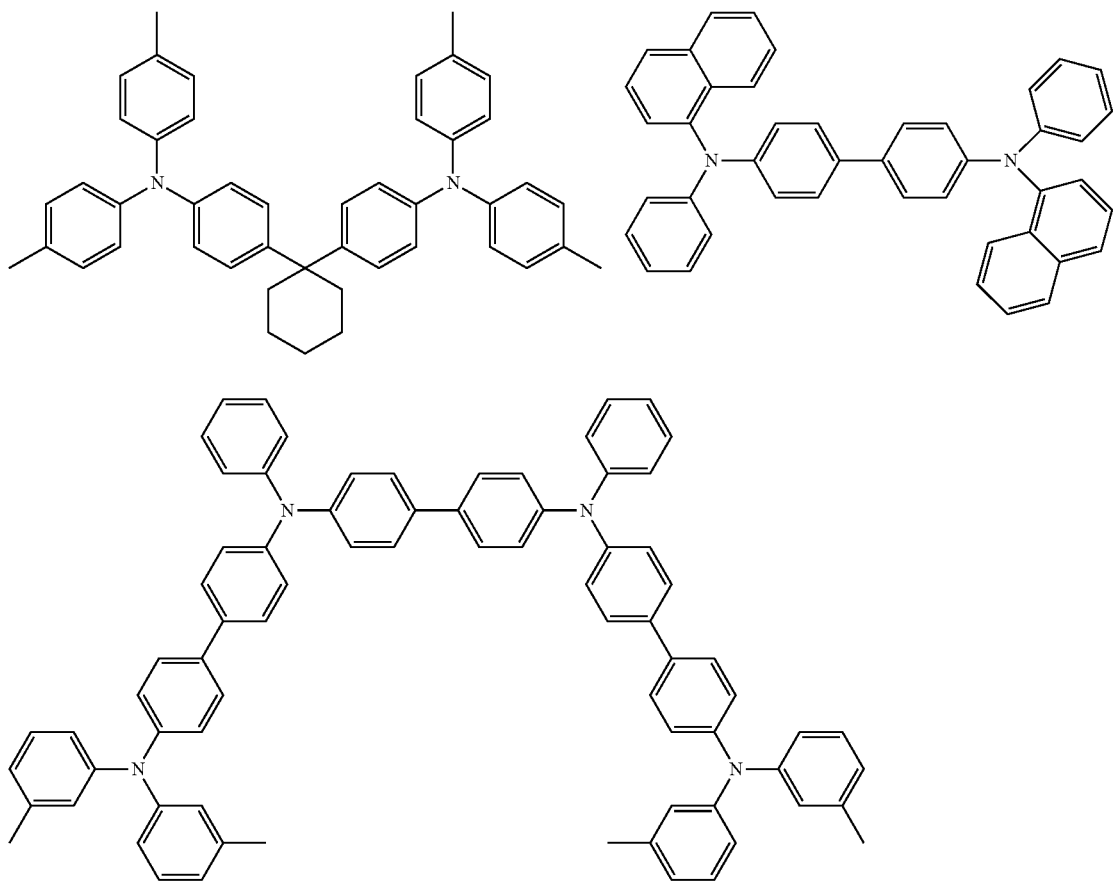

-continued
39
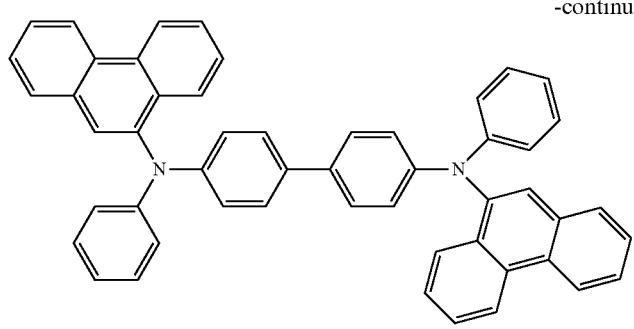
40
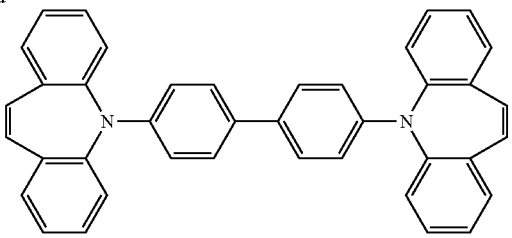
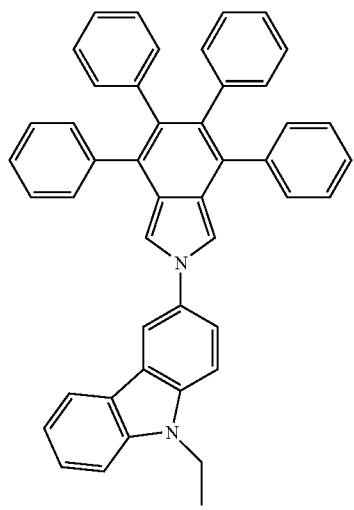
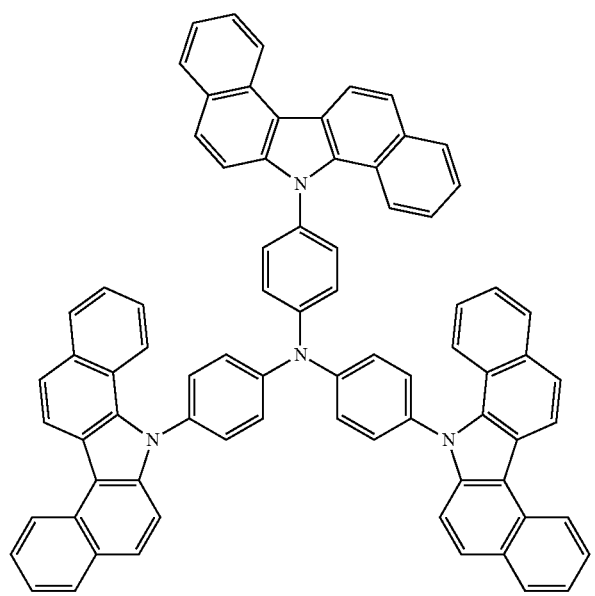
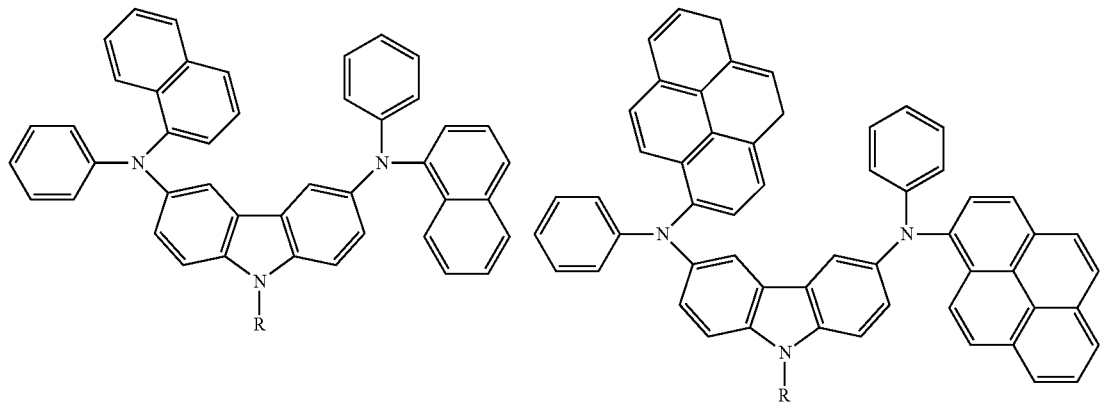

-continued
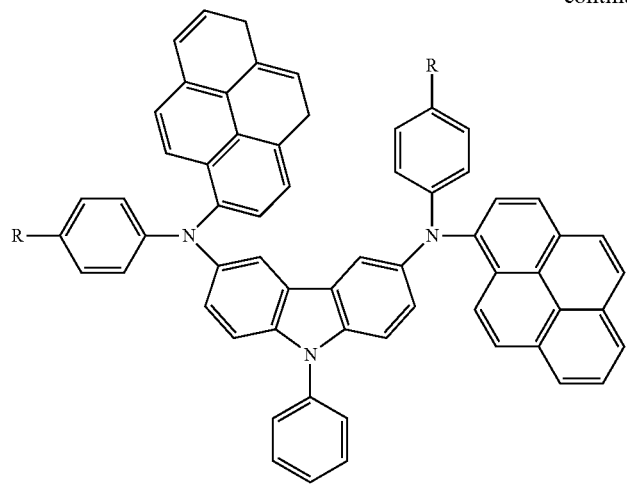
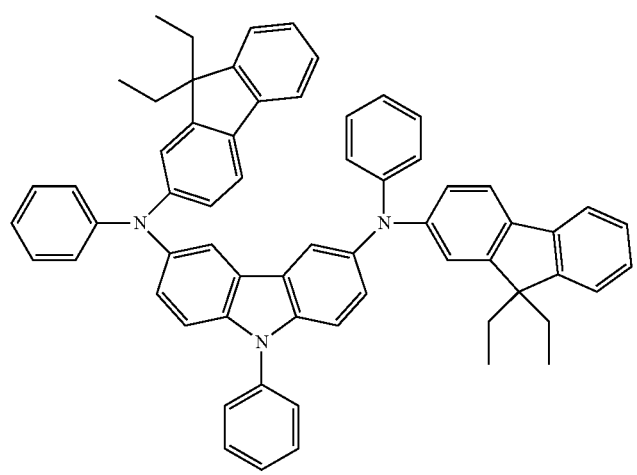
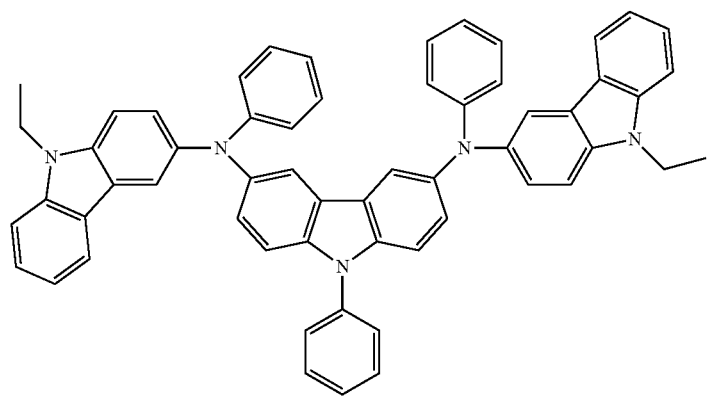

-continued
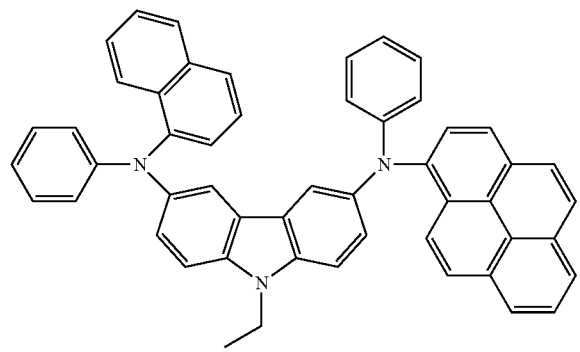
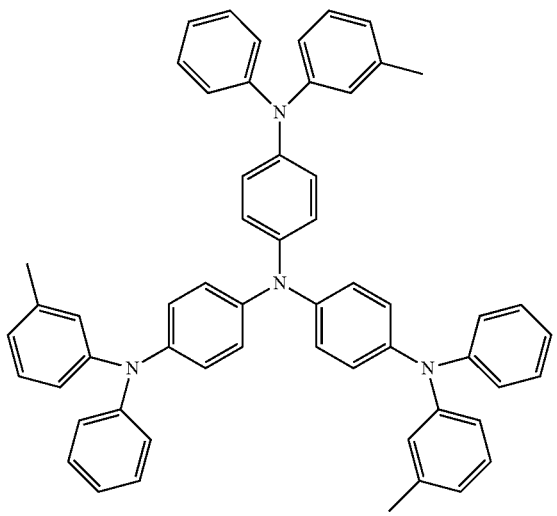
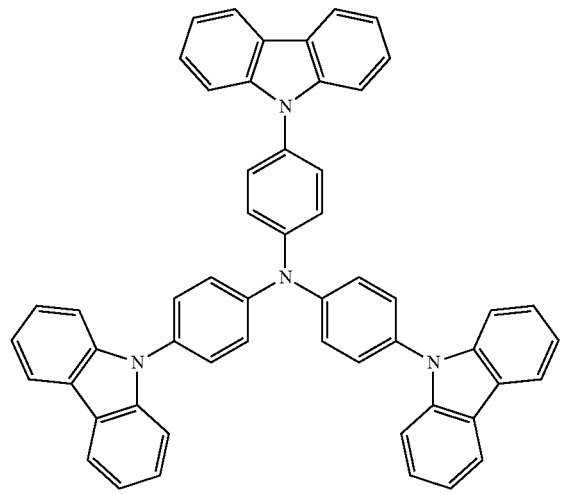
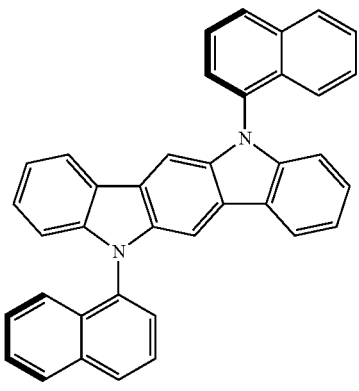
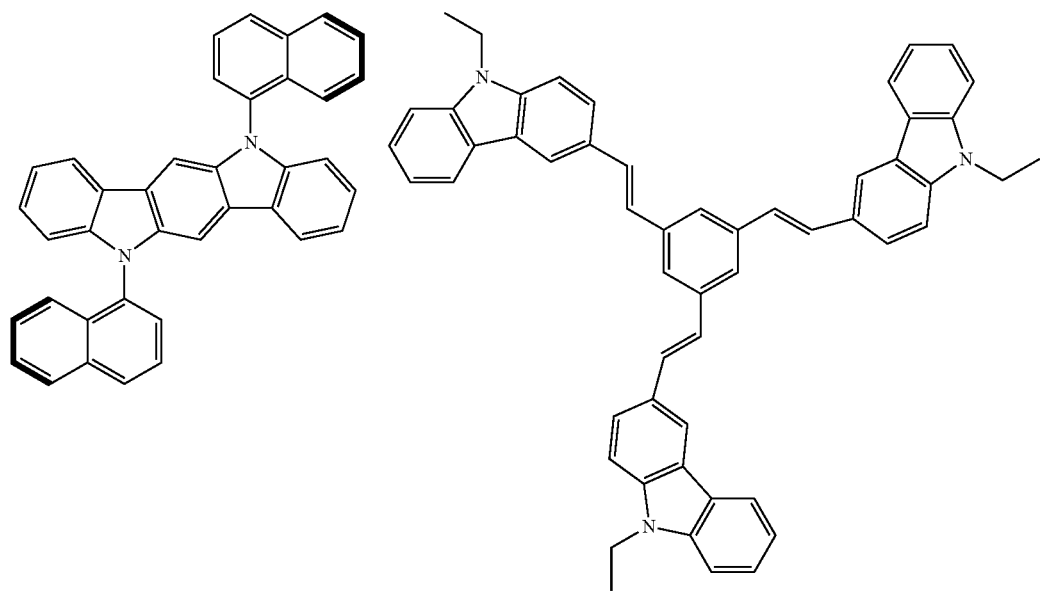

-continued
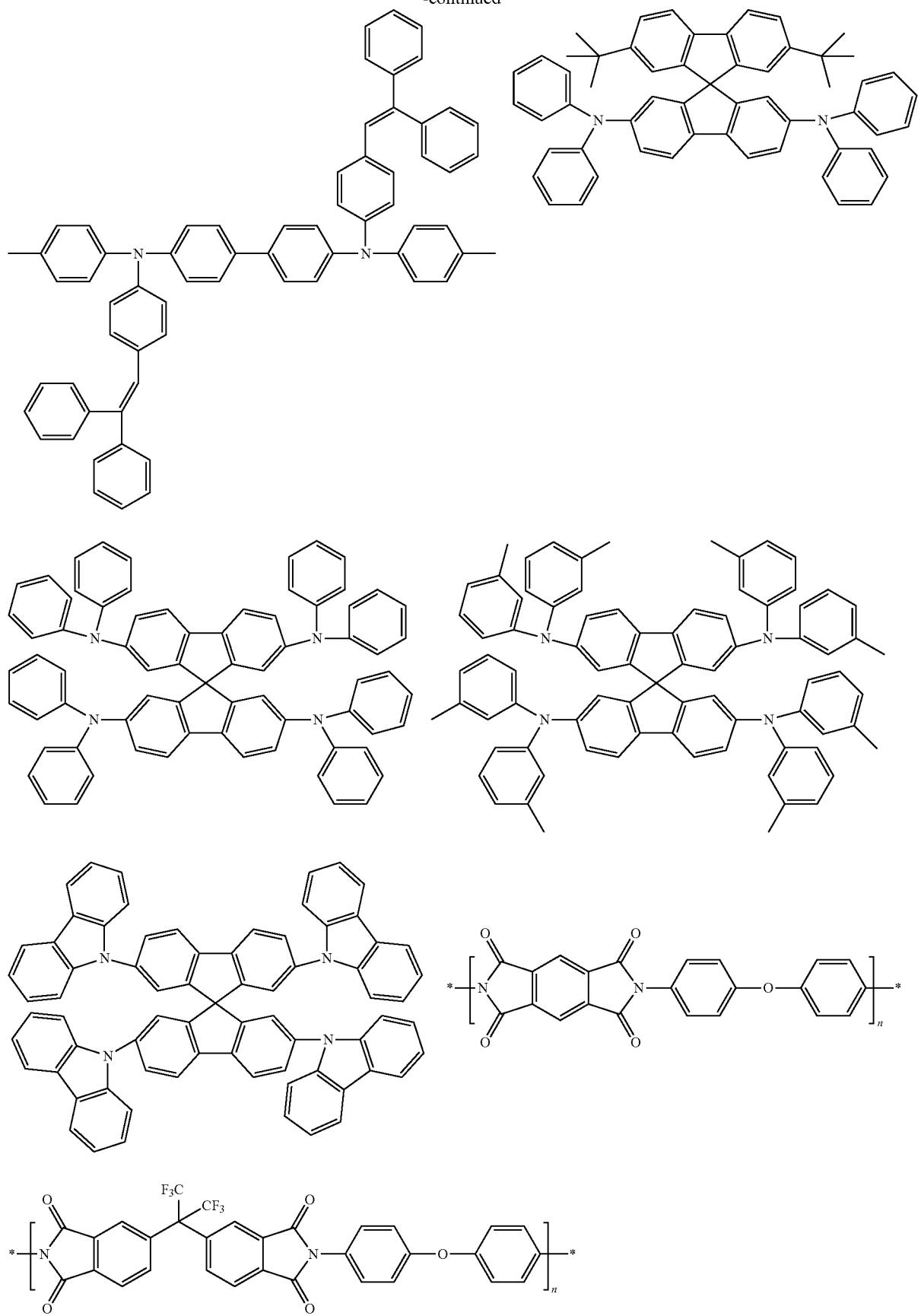

-continued
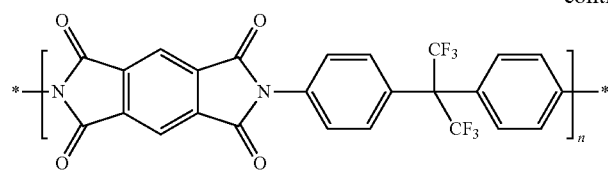
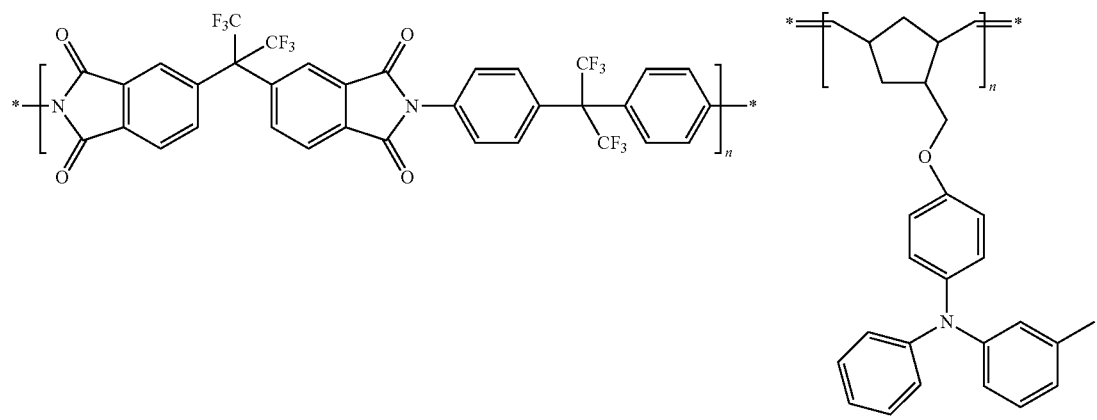
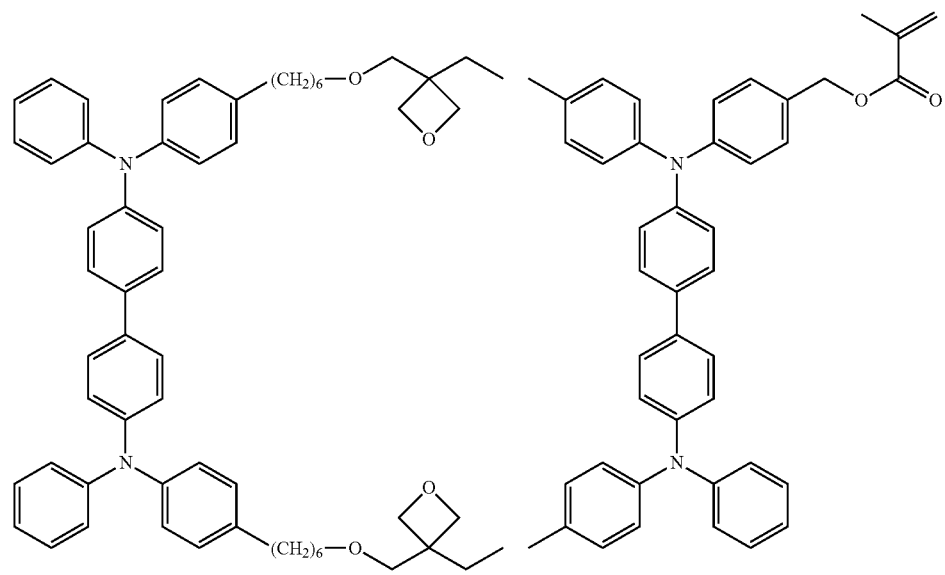

R =
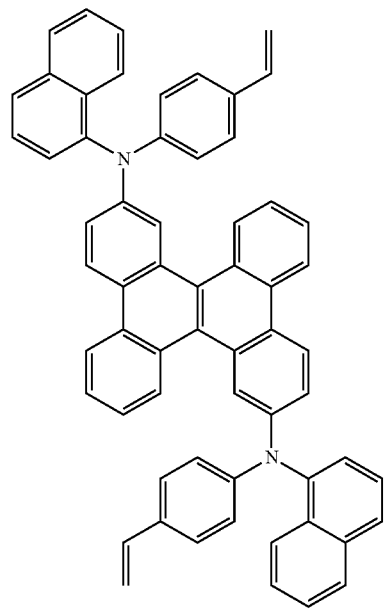
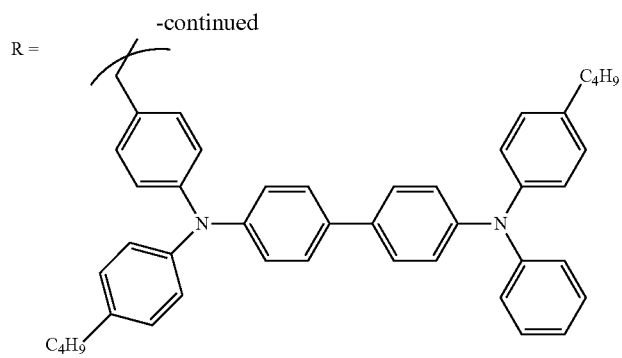
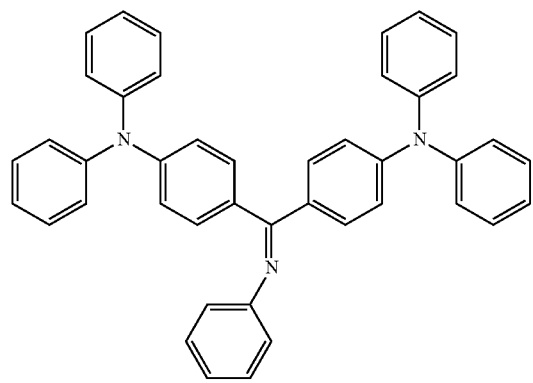
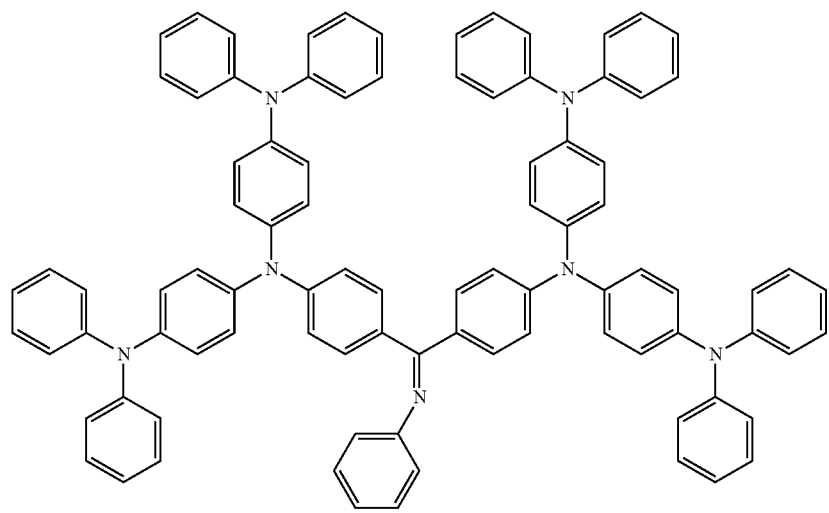

-continued
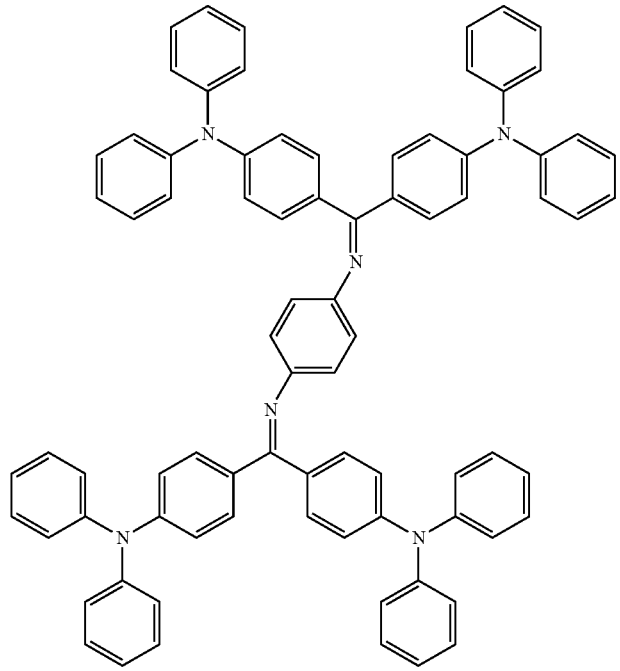
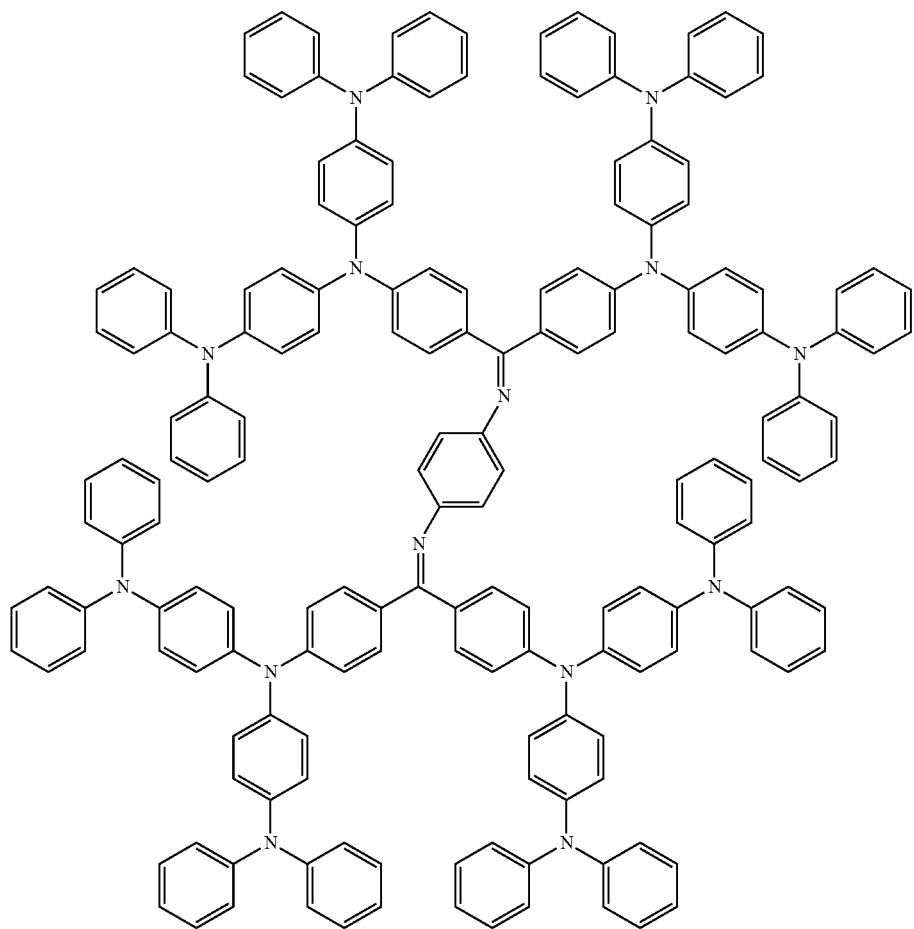

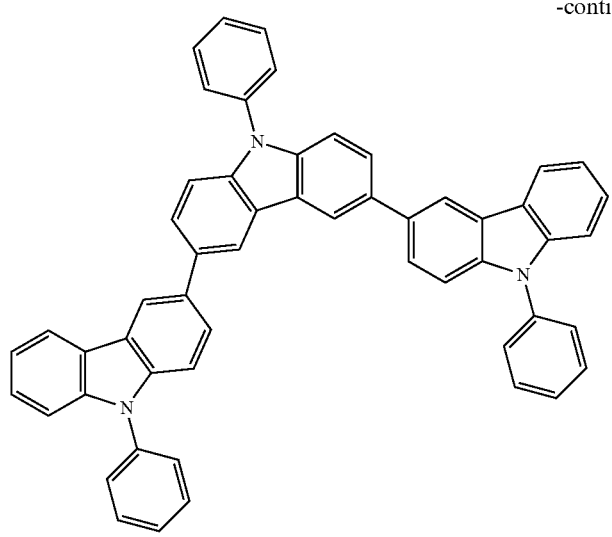
Preferred examples of a compound that may be used as the electron barrier material are shown below.
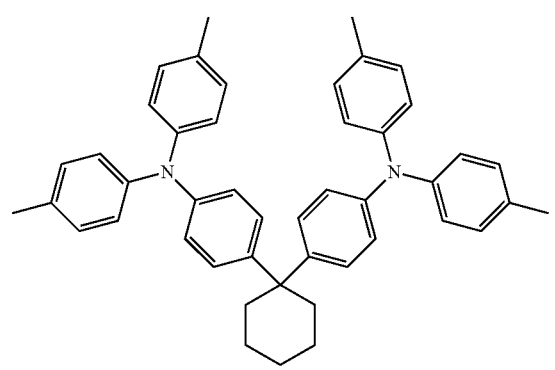
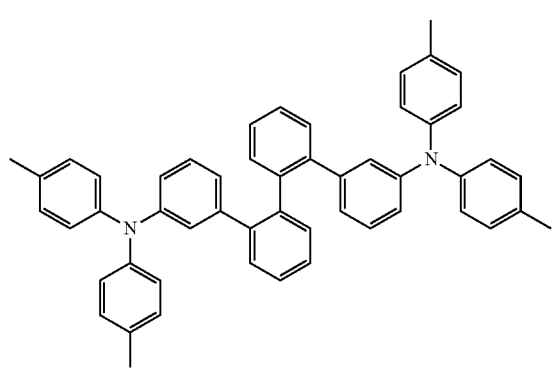
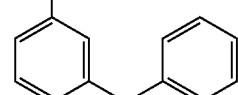
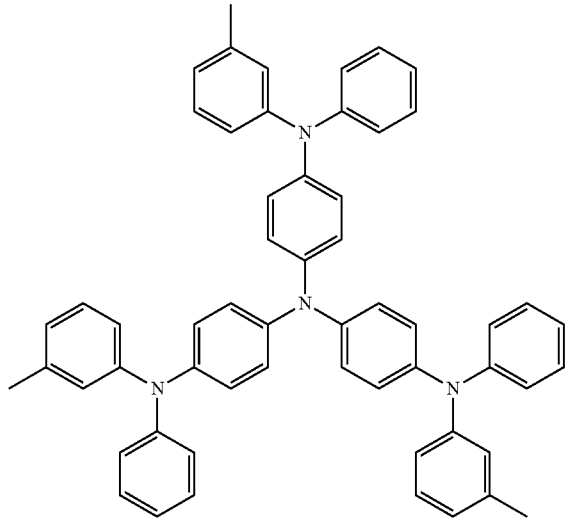
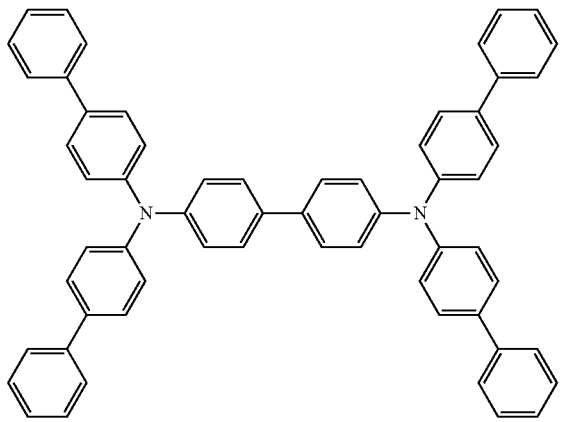
Preferred examples of a compound that may be used as the hole barrier material are shown below.

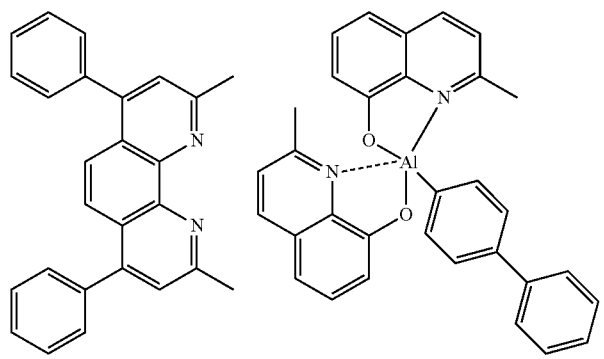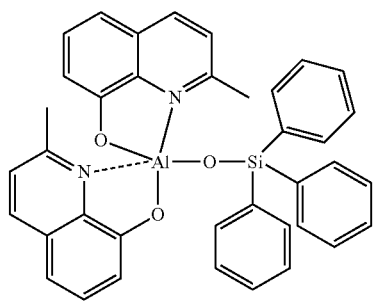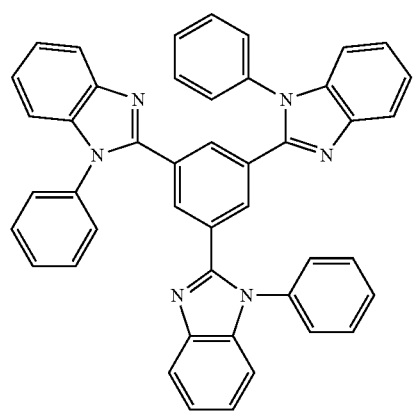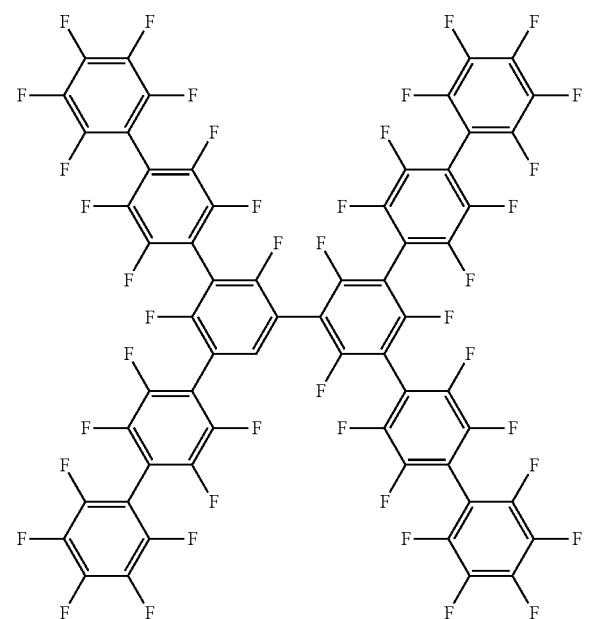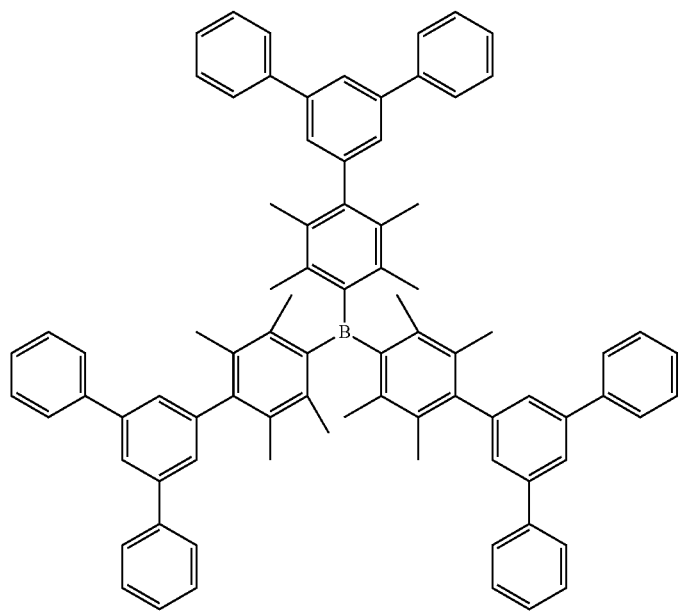

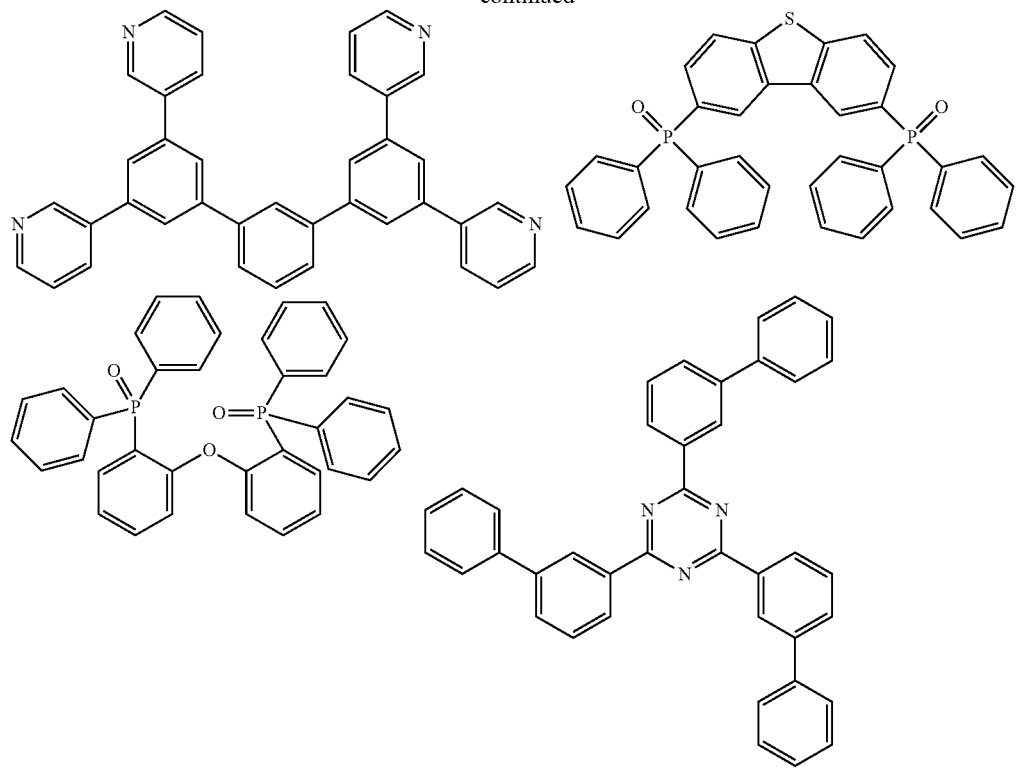
Preferred examples of a compound that may be used as the electron transporting material are shown below.
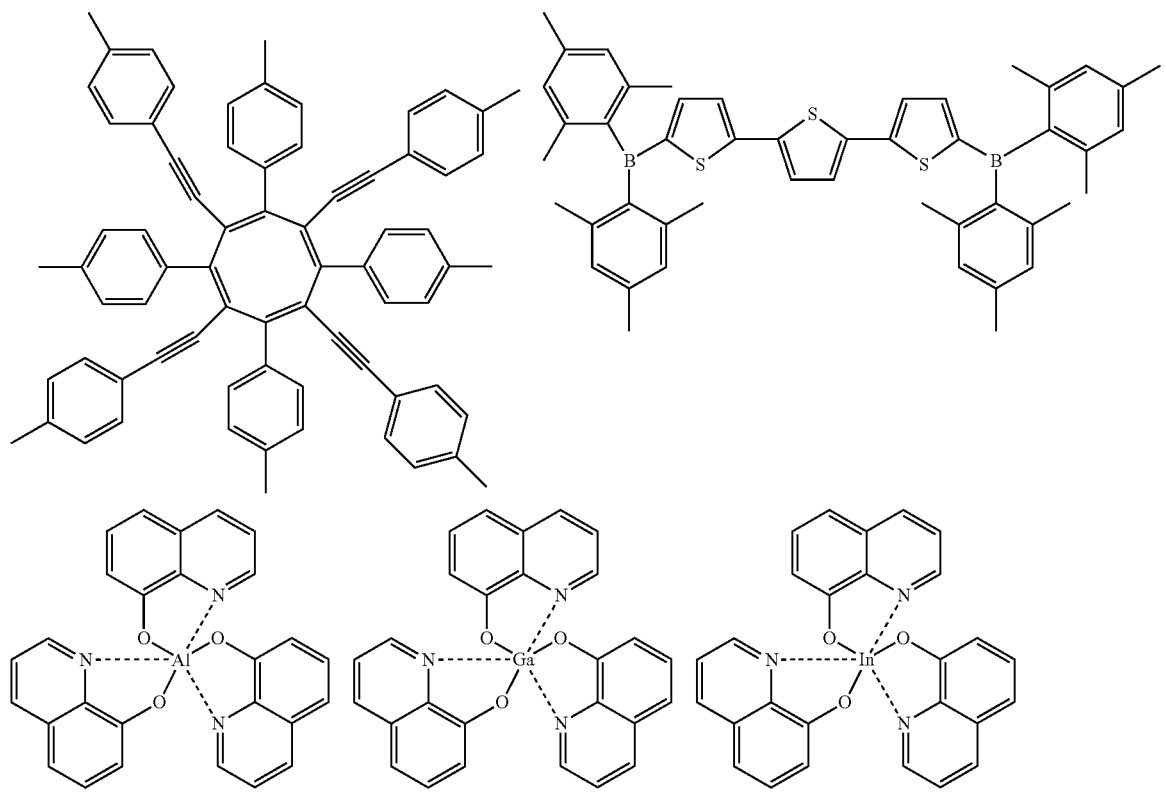

-continued
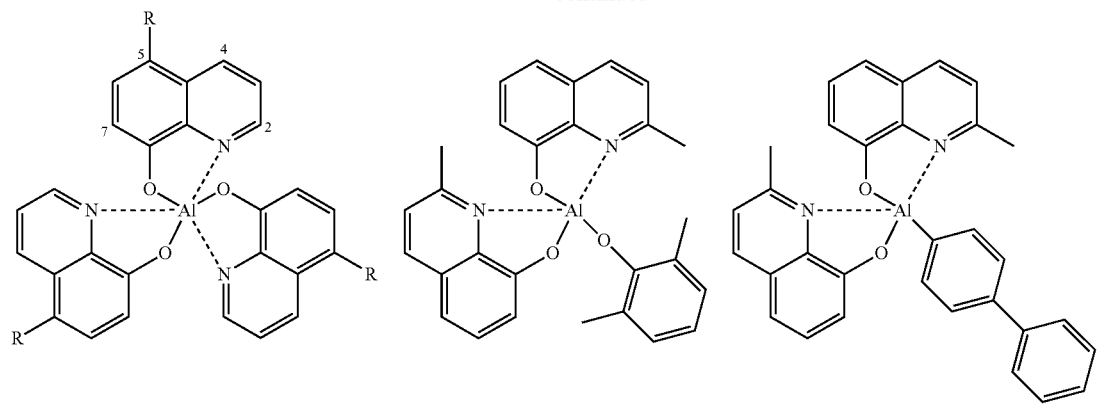
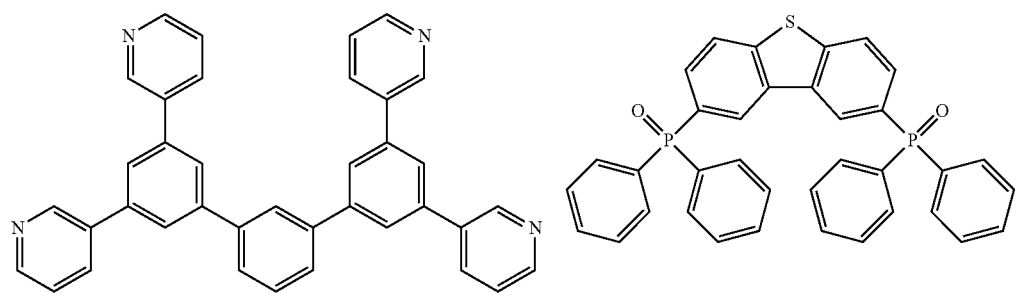
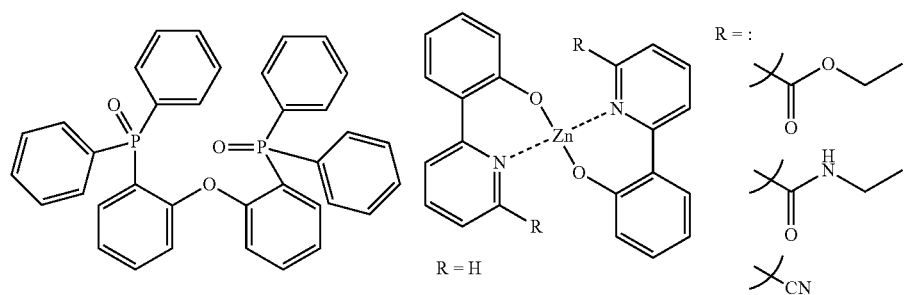
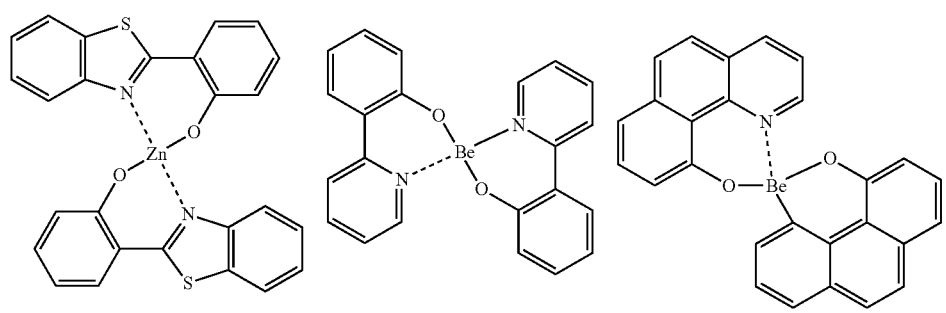

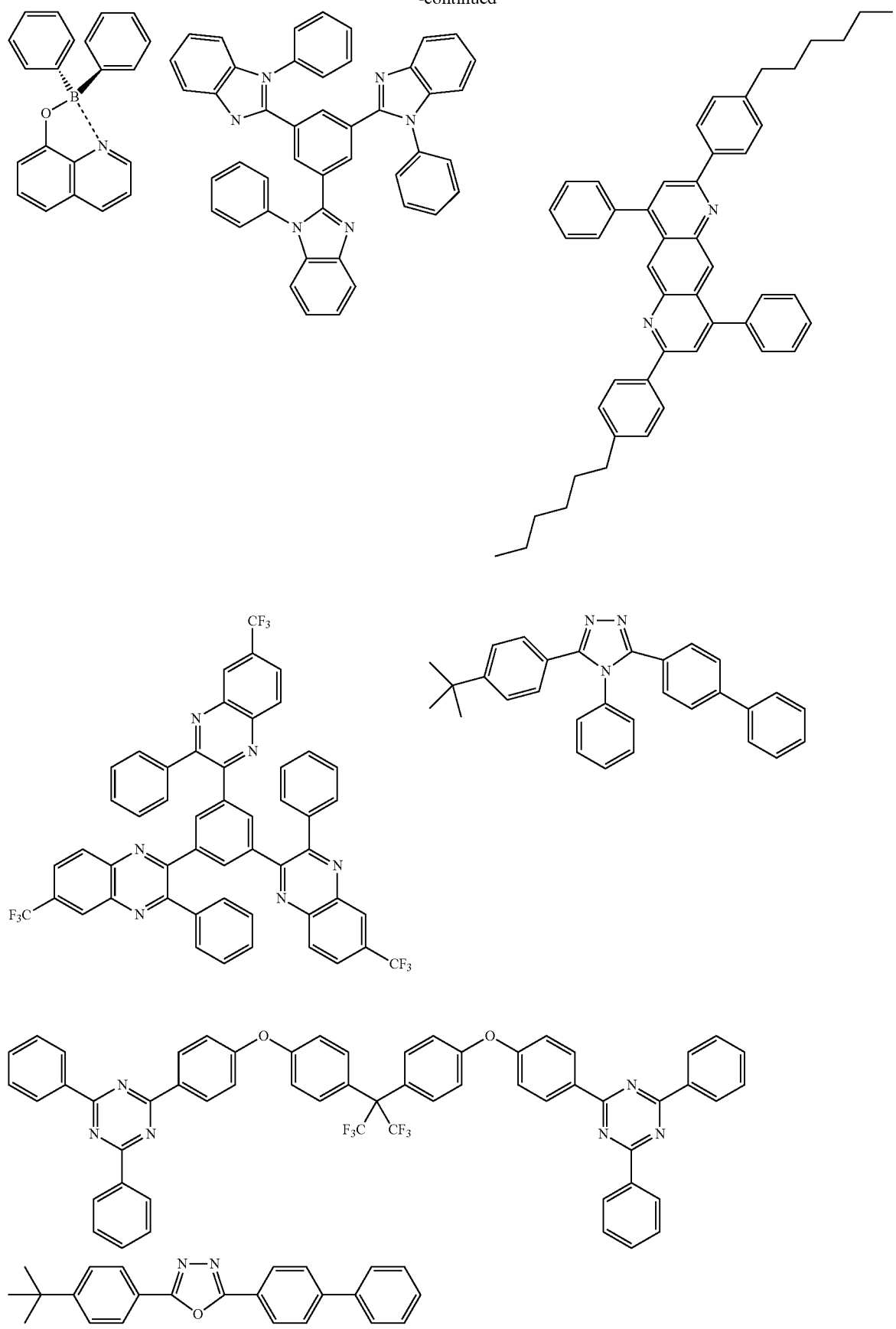

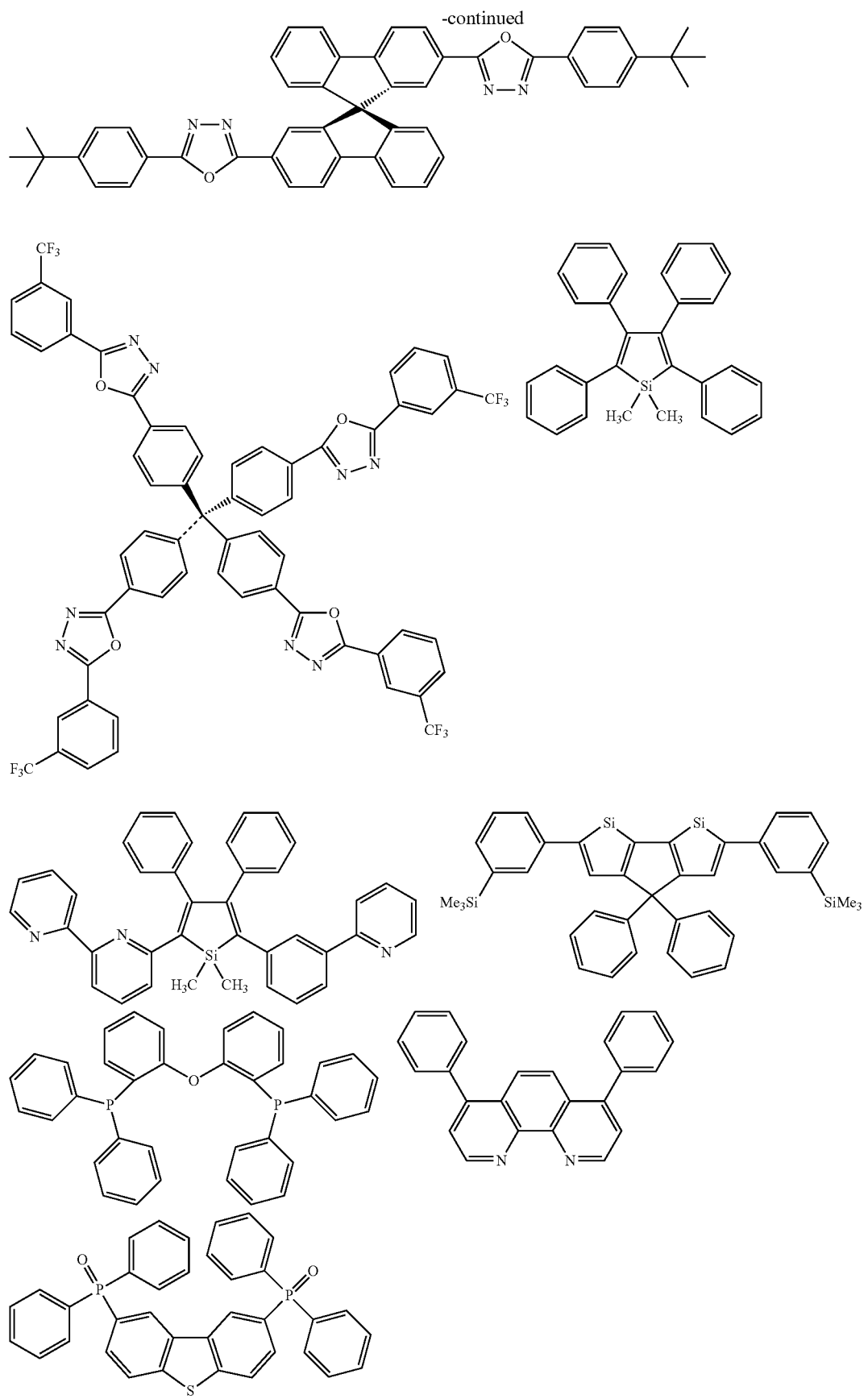

Preferred examples of a compound that may be used as the electron injection, material are shown below.

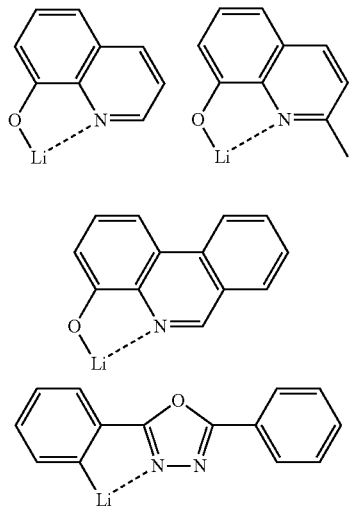

Preferred examples of a compound as a material that may be added are shown below. For example, the compound may be added as a stabilizing material.

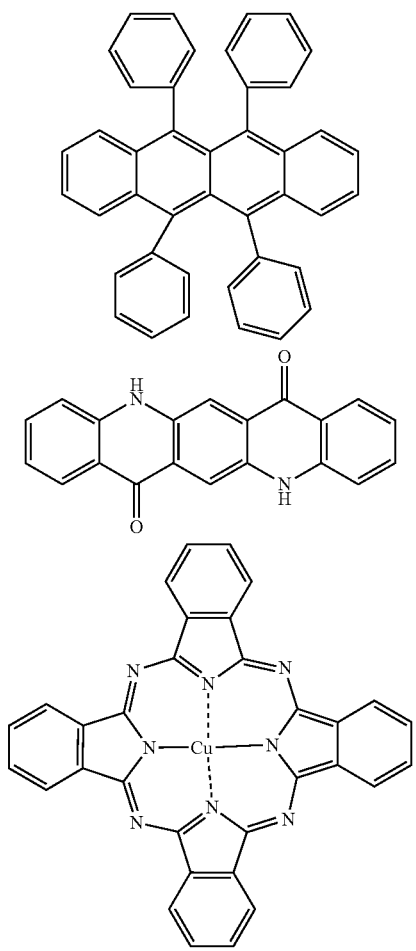

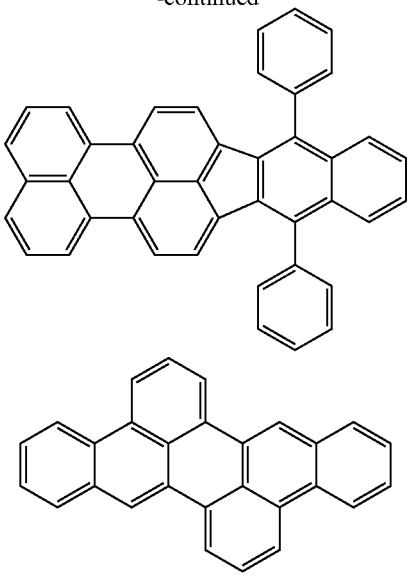

The organic electroluminescent device thus produced by the aforementioned method emits light on application of an electric field between the anode and the cathode of the device. In this case, when the light emission is caused by the excited singlet energy, light having a wavelength that corresponds to the energy level thereof may be confirmed as fluorescent light and delayed fluorescent light. When the light emission is caused by the excited triplet energy, light having a wavelength that corresponds to the energy level thereof may be confirmed as phosphorescent light. The normal fluorescent light has a shorter light emission lifetime than the delayed fluorescent light, and thus the light emission lifetime may be distinguished between the fluorescent light and the delayed fluorescent light.

The phosphorescent light may substantially not observed with a normal organic compound, such as the compound of the invention, at room temperature since the excited triplet energy is converted to heat or the like due to the instability thereof, and is immediately deactivated with a short lifetime. The excited triplet energy of the normal organic compound may be measured by observing light emission under an extremely low temperature condition.

The organic electroluminescent device of the invention may be applied to any of a single device, a structure with plural devices disposed in an array, and a structure having anodes and cathodes disposed in an X-Y matrix. According to the invention, an organic light-emitting device that is largely improved in light emission efficiency may be obtained by adding the compound represented by the general formula (1) in the light-emitting layer. The organic light-emitting device, such as the organic electroluminescent device, of the invention may be applied to a further wide range of purposes. For example, an organic electroluminescent display apparatus may be produced with the organic electroluminescent device of the invention, and for the details thereof, reference may be made to S. Toki to, C. Adachi and H. Murata, "Yuki EL Display" (Organic EL Display) (Ohmsha, Ltd.). In particular, the organic electroluminescent device of the invention may be applied to organic electroluminescent illumination and backlight which are highly demanded.

EXAMPLE

The features of the invention will be described more specifically with reference to synthesis examples and working examples below. The materials, processes, procedures and the like shown below may be appropriately modified unless they deviate from the substance of the invention. Accordingly, the scope of the invention is not construed as being limited to the specific examples shown below. The light emission characteristics were evaluated by using a high-performance UV/Vis/NIR spectrophotometer (Lambda 950, produced by PerkinElmer, Co., Ltd.), a fluorescence spectrophotometer (FluoroMax-4, produced by Horiba, Ltd.), an absolute PL quantum yield measurement system (C11347, produced by Hamamatsu Photonics K.K.), a source meter (2400 Series, produced by Keithley Instruments Inc.), a semiconductor parameter analyzer (E5273A, produced by Agilent Technologies, Inc.), an optical power meter (1930C, produced by Newport Corporation) an optical spectrometer (USB2000, produced by Ocean Optics, Inc.), a spectroradiometer (SR-3, produced by Topcon Corporation), and a streak camera (Model C4334, produced by Hamamatsu Photonics K.K.). The molecular orientation was measured by using an ellipsometer (M-2000, produced by J. A. Woollam Co., Inc.). The optical model construction, the fitting for minimizing the mean square error between the optical model and the measured values, and the like were performed by using WASE32, an analysis software for ellipsometry data (produced by J. A. Woollam Co., Inc.). The order parameter S for evaluating the extent of orientation was defined by the following expression.

$$S = \frac{1}{2}(3\cos^2\theta - 1) = \frac{k_e - k_o}{k_e + 2k_o}$$

wherein θ represents the average value of the angle between the normal line direction of the substrate and the molecule, and $k_o$ and $k_e$ represent the extinction coefficients of molecules having a transition dipole in the horizontal direction and the normal direction with respect to the substrate, respectively.

Synthesis Example 1

Synthesis of Compound 1
(1-1) Synthesis Process of Intermediate 1

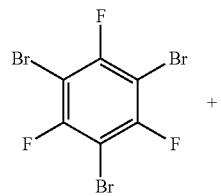

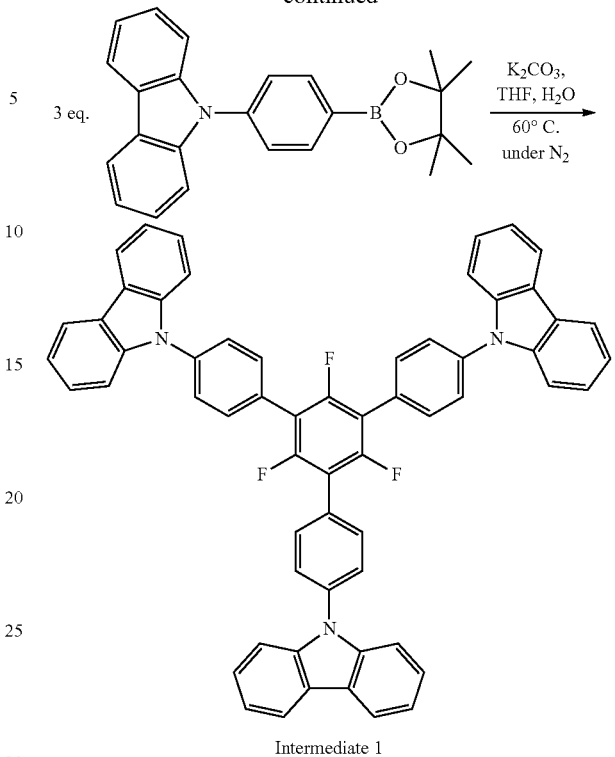

Intermediate 1

1,3,5-tribromo-2,4,6-trifluorobenzene (0.738 g, 2 mmol), 2-(4-(9H-carbazolyl-9-yl)phenyl-1-yl)-4,4,5,5-tetramethyl-1,3,2-dioxaborolane (0.52 g, 1.4 mmol) tetrahydrofuran (55 ml), tetrakis(triphenylphosphine) palladium (Pd(PPh₃)₄, 0.30 g, 0.26 mmol), and 2 M K₂CO₃ aq (15 mL) were placed in a 200 mL three-neck flask, and then deaerated. The solution thus deaerated was heated to 66° C. under a nitrogen stream, to which a solution containing 1,4-(4-(9H-carbazolyl-9-yl) phenyl-1-yl)-4,4,5,5-tetramethyl 1,3,2-dioxaborolane (1.70 g, 4.6 mmol) dissolved in 20 mL of tetrahydrofuran was added dropwise over 12 hours, and the solution was agitated for 6 days while retaining the temperature to 66° C. After returning the reaction solution to room temperature, tetrahydrofuran was removed from the reaction solution with an evaporator, so as to provide a precipitate. The precipitate was filtered off, then rinsed with water, and dried in vacuum. The resulting solid matter was added to 200 mL of heated dichloromethane to form a solution, and the solution was filtered and the concentrated. n-Hexane was added to the resulting concentrated matter to deposit white powder, and the white powder (intermediate 1) thus deposited was filtered off. 1,3,5-(4-(9H-Carbazolyl-9-yl)phenyl-1-yl)-2,4,6-trifluorobenzene as the intermediate 1 was obtained through the aforementioned process in a yield amount of 683 mg (0.80 mmol) and a yield of 40%.

¹H-NMR (500 MHz, CDCl₃): δ=7.33 (t, J=7.4 Hz, 6H; ArH), 7.46 (dt, J$_{ortho}$=7.6 Hz, J$_{meta}$=1.0 Hz, 6H; ArH), 7.55 (d, J=8.2 Hz, 6H; ArH), 7.76 (d, J=8.4 Hz, 6H; ArH), 7.84 (d, J=8.2 Hz, 6H; ArH), 8.17 (d, J=7.8 Hz, 6H; ArH)

¹⁹F-NMR (500 MHz, CDCl₃): δ=−115.32

(1-2) Synthesis Process of Compound 1

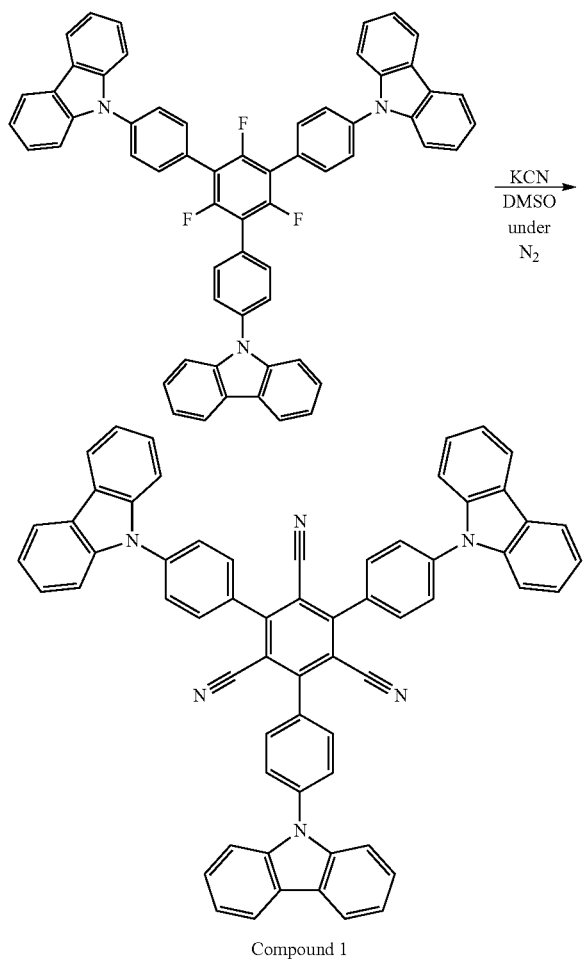

Compound 1

Under a nitrogen stream, the intermediate 1 (1,3,5-(4-(9H-carbazolyl-9-yl)phenyl-1-yl)-2,4,6-trifluorobenzene) (0.86 g, 1.0 mmol) and potassium cyanide (0.85 g, 13 mmol) were placed in a 200 mL three-neck flask, to which 70 mL of dimethylsulfoxide was added, and the solution was heated to 160° C. under agitation for 1 hour. The reaction solution was radiationally cooled, to which 450 mL of dichloromethane and 800 mL of water were added, and the mixture was separated. 450 mL of dichloromethane was added to the aqueous layer for extraction, and the resulting organic layer was combined to the organic layer obtained by the previous separation. The organic layer was rinsed with 500 mL of water and 500 mL of a saturated sodium chloride aqueous solution, and then dried over anhydrous magnesium sulfate, from which the solvent was removed with an evaporator. The resulting residue was recrystallized from a mixed solvent of dichloromethane and n-hexane, thereby providing 1,3,5-(4-(9H-carbazolyl-9-yl)phenyl-1-yl)-2,4,6-tricyanobenzene in the form of an orange solid matter (compound 1) in a yield amount of 719 mg (0.82 mmol) and a yield of 82%.

$^1$H-NMR (500 MHz, CDCl$_3$): δ=7.35 (dt, J$_{ortho}$=6.8 Hz, J$_{meta}$=0.7 Hz, 6H; ArH), 7.48 (dt, J$_{ortho}$=7.7 Hz, J$_{meta}$=1.2 Hz, 6H; ArH), 7.60 (d, J=8.3 Hz, 6H; ArH), 7.91-7.97 (m, 12H; ArH), 8.17 (d, J=7.8 Hz, 6H; ArH)

Anal. Calcd for C$_{42}$H$_{24}$F$_4$N$_2$: C, 86.28; H, 4.14; N, 9.58%.

Found: C, 86.35; H, 4.11; N, 9.29%.

Synthesis Example 2

Synthesis of Compound 2

(2-1) Synthesis Process of Intermediate 2

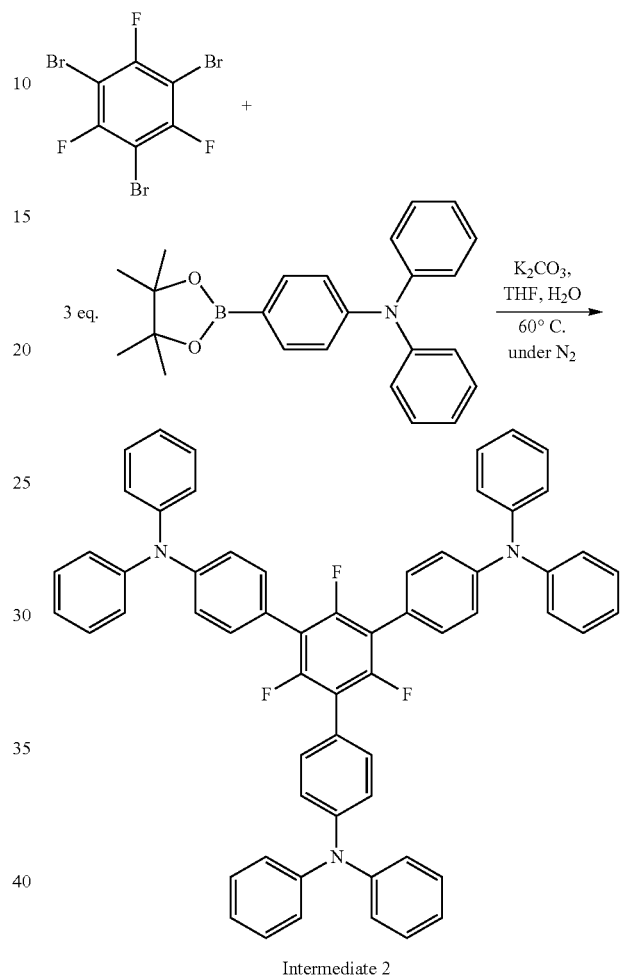

Intermediate 2

1,3,5-tribromo-2,4,6-trifluorobenzene (0.738 g, 2 mmol) 2-(4-(diphenylamino)phenyl-1-yl)-4,4,5,5-tetramethyl-1,3,2-dioxaborolane (0.25 g, 0.7 mmol), tetrahydrofuran (55 mL), Pd(PPh$_3$)$_4$ (0.30 g, 0.26 mmol), and 2 M K$_2$CO$_3$ ac (15 mL) were placed in a 200 three-neck flask, and then deaerated. The solution thus deaerated was heated to 66° C. under a nitrogen stream, to which a solution containing 1,4-(4-(diphenylamino)phenyl-1-yl)-4,4,5,5-tetramethyl-1,3,2-dioxaborolane (2.0 g, 5.4 mmol) dissolved in 20 mL of tetrahydrofuran was added dropwise over 12 hours, and the solution was agitated for 4 days while retaining the temperature to 66° C. After returning the reaction solution to room temperature, tetrahydrofuran was removed from the reaction solution with an evaporator, so as to provide a precipitate. The precipitate was filtered off, then rinsed with water, and dried in vacuum. The resulting solid matter was added to 25 mL of heated dichloromethane to form a solution, and the solution was filtered and the concentrated. n-Hexane was added to the resulting concentrated matter to deposit white powder, and the white powder (intermediate 2) thus deposited was filtered off, and rinsed with methanol.

1,3,5-(4-(diphenylamino)phenyl-1-yl)-2,4,6-trifluorobenzene as the intermediate 2 was obtained through the aforementioned process in a yield amount of 577 mg (0.67 mmol) and a yield of 34%.

$^1$H-NMR (500 MHz, CDCl$_3$): δ=7.05 (t, J=7.3 Hz, 6H; Ar H), 7.13 (dd, J$_{ortho}$=8.8 Hz, J$_{meta}$=2.0 Hz, 6H; ArH), 7.15 (td, J$_{ortho}$=7.5 Hz, J$_{meta}$=1.1 Hz, 12H; ArH), 7.28 (dt, J$_{ortho}$=7.0 Hz, J$_{meta}$=1.5 Hz, 12H; ArH), 7.34 (d, J=8.5 Hz, 6H; ArH)

$^{19}$F-NMR (500 M Hz, CDCl$_3$): δ=−117.09

(2-2) Synthesis Process of Compound 2

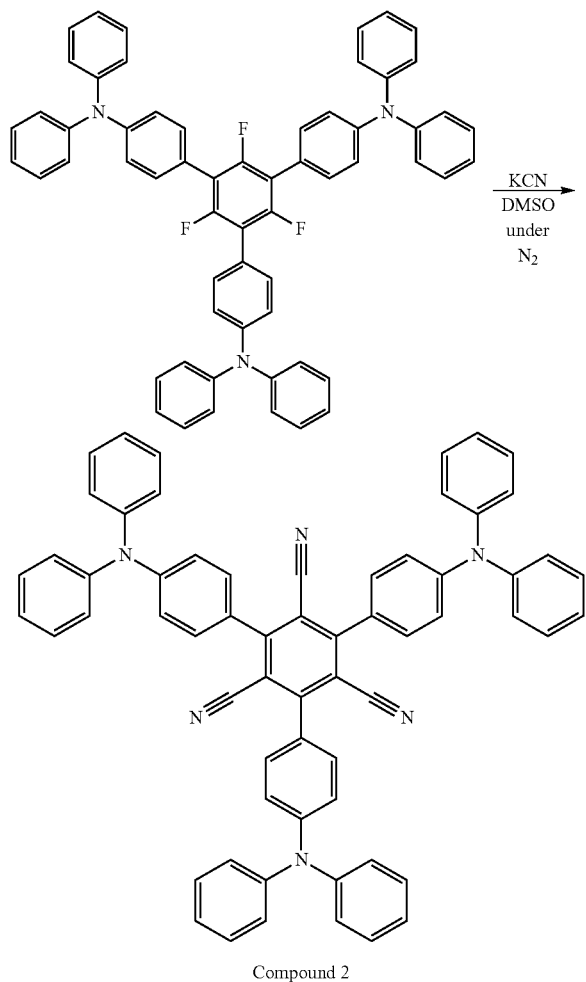

Compound 2

Under a nitrogen stream, 1,3,5-(4-(diphenylamino)phenyl-1-yl)-2,4,6-trifluorobenzene (0.86 g, 1.0 mmol) and potassium cyanide (1.02 g, 16 mmol) were placed in a 200 mL three-neck flask, to which 60 mL of dimethylsulfoxide was added, and the solution was heated to 160° C. under agitation for 80 minutes. The reaction solution was radiationally cooled, to which 450 mL of dichloromethane and 450 mL of water were added, and the mixture was separated. The organic layer was rinsed with 500 mL of water and 500 mL of a saturated sodium chloride aqueous solution, and then dried over anhydrous magnesium sulfate, from which the solvent was removed with an evaporator. The resulting residue was recrystallized from a mixed solvent of dichloromethane and n-hexane, thereby providing 1,3,5-(4-(diphenylamino)phenyl-1-yl)-2,4,6-tricyanobenzene in the form of an orange solid matter (compound 2) in a yield amount of 875 mg (0.99 mmol) and a yield of 99%.

$^1$H-NMR (500 MHz, CDCl$_3$): δ=7.11-7.14 (m, 12H; Ar H), 7.21 (d, J=7.6 Hz, 12H; ArH), 7.32 (t, J=7.9 Hz, 12H; Ar H), 7.41 (d, J=8.7 Hz, 6H; ArH)

Anal. Calcd for C$_{63}$H$_{42}$N$_6$: C, 85.69; H, 4.79; N, 9.52%. Found: C, 85.44; H, 4.74; N, 9.42%.

Comparative Synthesis Example 1

The intermediate 1 obtained according to the synthesis method of Synthesis Example 1 was designated as a comparative compound 1.

Comparative Synthesis Example 2

The intermediate 2 obtained according to the synthesis method of Synthesis Example 2 was designated as a comparative compound 2.

Example 1

Production and Evaluation of Organic Photoluminescent Device Using Compound 1

A toluene solution of the compound 1 was prepared in a glove box under an Ar atmosphere.

On a quartz substrate, the compound 1 was formed into a thin film having a thickness of 50 nm by a vacuum vapor deposition method under condition of a vacuum degree of 4×10$^{-4}$ Pa or less, thereby providing an organic photoluminescent device.

Separately, on a quartz substrate, the compound 1 and mCP were vapor-deposited from separate vapor deposition sources by a vacuum vapor deposition method under condition of a vacuum degree of 4×10$^{-4}$ Pa or less to form a thin film having a concentration of the compound 1 of 6.0% by weight and a thickness of 50 nm, which was designated as an organic photoluminescent device.

The organic photoluminescent device having the thin film containing only the compound 1 was measured for orientation by an ellipsometric spectroscopy method, and the orientation angle of the molecule of the compound 1 with respect to the film forming surface was 16.8°.

Figure 2:
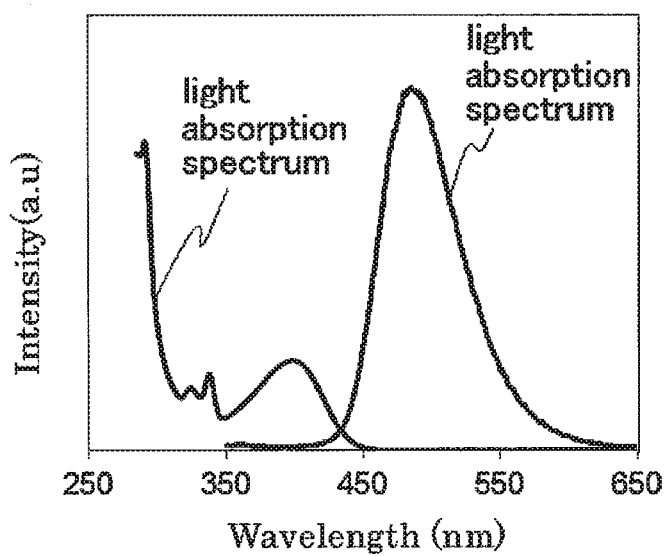
FIG. 2 shows the light absorption and emission spectra of the toluene solution of the compound 1 in Example 1.
Figure 3:
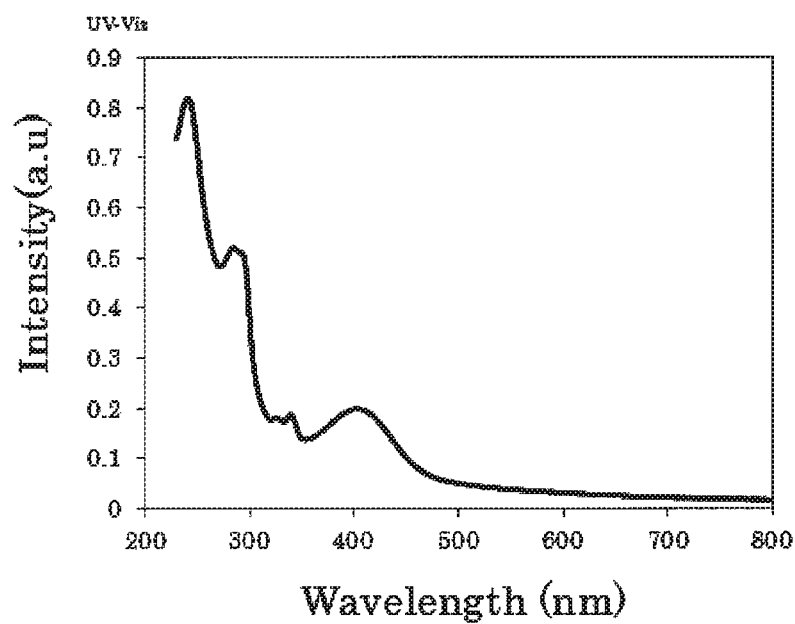
FIG. 3 shows the light absorption spectrum of the organic photoluminescent device having the thin film containing only the compound 1 in Example 1.
Figure 4:
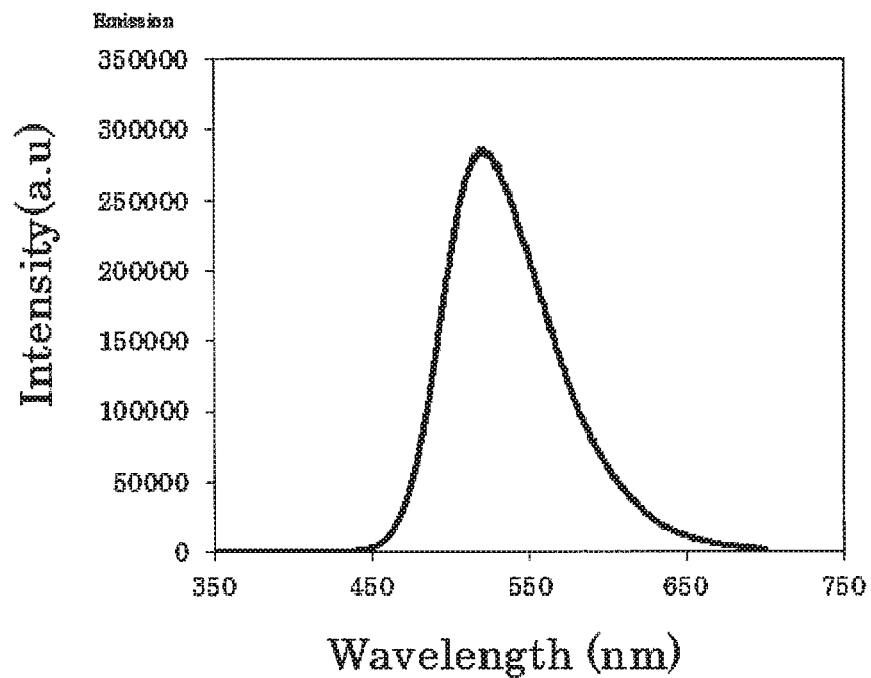
FIG. 4 shows the light emission spectrum of the thin film organic photoluminescent device of the compound 1 in Example 1.
Figure 5:
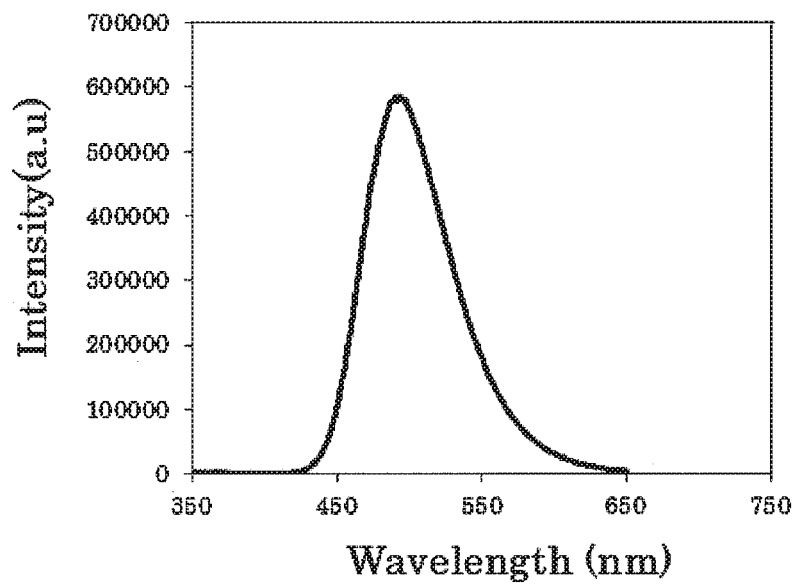
FIG. 5 shows the light emission spectrum of the thin film organic photoluminescent device of the compound 1 and mCP in Example 1.

The specimens using the compound 1 were measured for light emission spectrum with excitation light of 337 nm. FIG. 2 shows the light absorption and emission spectra of the toluene solution. FIG. 3 shows the light absorption spectrum of the organic photoluminescent device having the thin film containing only the compound 1, and FIG. 4 shows the light emission spectrum thereof. FIG. 5 shows the light emission spectrum of the organic photoluminescent device having the thin film containing the compound 1 and mCP.

For the toluene solution, the maximum light emission wavelength was 487 nm, and the photoluminescence quantum efficiency was 67.0% in the air and 89.3% after deaeration. For the organic photoluminescent device having the thin film containing only the compound 1, the maximum light emission wavelength was 519 nm, and the photoluminescence quantum efficiency was 85%. For the organic photoluminescent device having the thin film containing the compound 1 and mCP, the maximum light emission wavelength was 493 nm, and the photoluminescence quantum efficiency was 90%.

Figure 6:
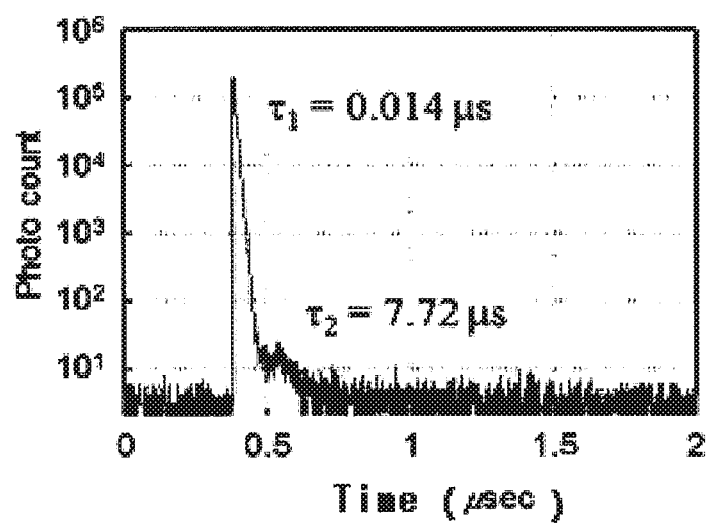
FIG. 6 shows the transient decay curve of the toluene solution of the compound 1 in Example 1.

FIG. 6 shows the result of measurement of the transient decay curve of the toluene solution of the compound 1. The transient decay curve shows the measurement result of the light emission lifetime obtained by measuring the process where the light emission intensity is deactivated on irradiating the compound with excitation light. In ordinary one-component light emission (fluorescent light or phosphorescent light), the light emission intensity is decays monoexponentially. This means that the light emission intensity decays linearly on a graph with the semilogarithm as the ordinate. In a transient decay curve of the compound 1 shown in FIG. 6, while a linear component (fluorescent light) was observed in the initial stage of observation, a component that deviated from the linearity appeared after several microseconds. The later component is light emission of the delayed component, and the signal thereof added to the initial component appears as a long tail curve on the longer time side. Thus, the measurement of the light emission lifetime, revealed that the compound 1 was a light-emitting material that contained a delayed component in addition to a fluorescent component. The light emission lifetime τ of the toluene solution in the air was 7.53 ns. Two kinds of fluorescent light (prompt fluorescent light and delayed fluorescent light) were observed in the transient decay curve of the toluene solution after deaeration, and the light emission lifetime $\tau_1$ of the prompt fluorescent light was 13.7 ns, and the light emission lifetime $\tau_2$ of the delayed fluorescent light was 7.72 µs.

Figure 7:
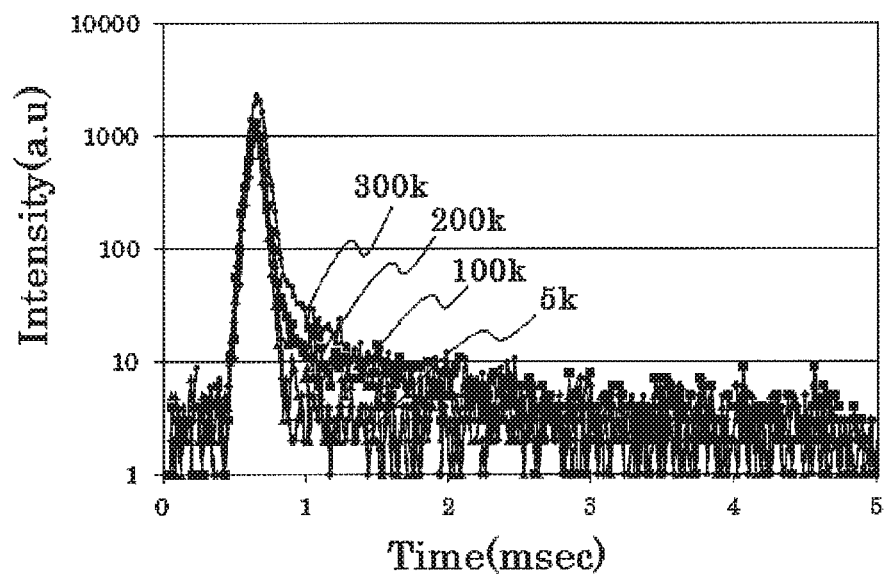
FIG. 7 shows the transient decay curves of the thin film organic photoluminescent device of the compound 1 and mCP in Example 1.

The organic photoluminescent device having the thin film containing the compound 1 and mCP was measured for transient decay curves at temperatures of 300 K, 200 K, 100 K, and 5 K. The results are shown in FIG. 7. FIG. 7 confirmed thermal activation type delayed fluorescent light with the delayed fluorescent light component that increased with the temperature rise.

Example 2

Production and Evaluation of Organic Photoluminescent Device Using Compound 2

A toluene solution of the compound 2, an organic photoluminescent device having a thin film containing only the compound 2, and an organic photoluminescent device having a thin film containing the compound 2 and mCP were produced by changing the point that the compound 2 was used instead of the compound 1.

The organic photoluminescent device having the thin film containing only the compound 2 was measured for orientation by an ellipsometric spectroscopy method, and the orientation angle of the molecule of the compound 2 with respect to the film forming surface was 20.4°.

Figure 8:
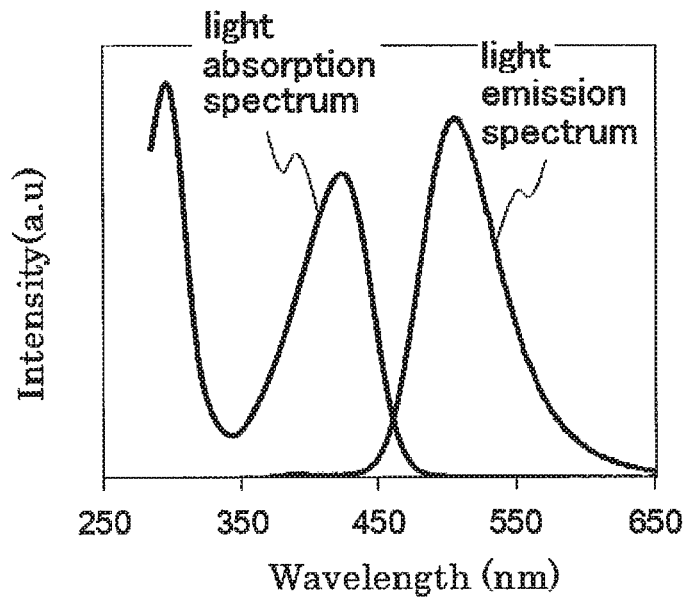
FIG. 8 shows the light absorption and emission spectra of the toluene solution of the compound 2 in Example 2.
Figure 9:
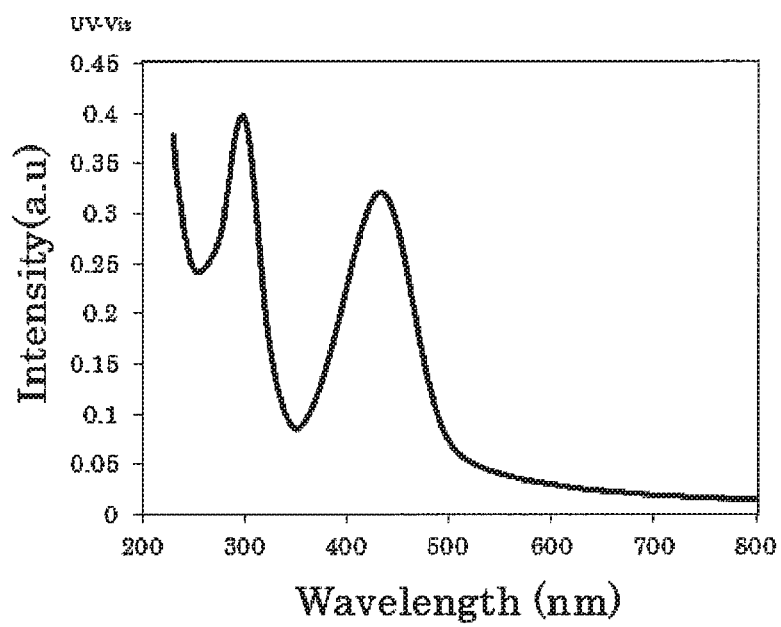
FIG. 9 shows the light absorption spectrum of the thin film organic photoluminescent device of the compound 2 in Example 2.
Figure 10:
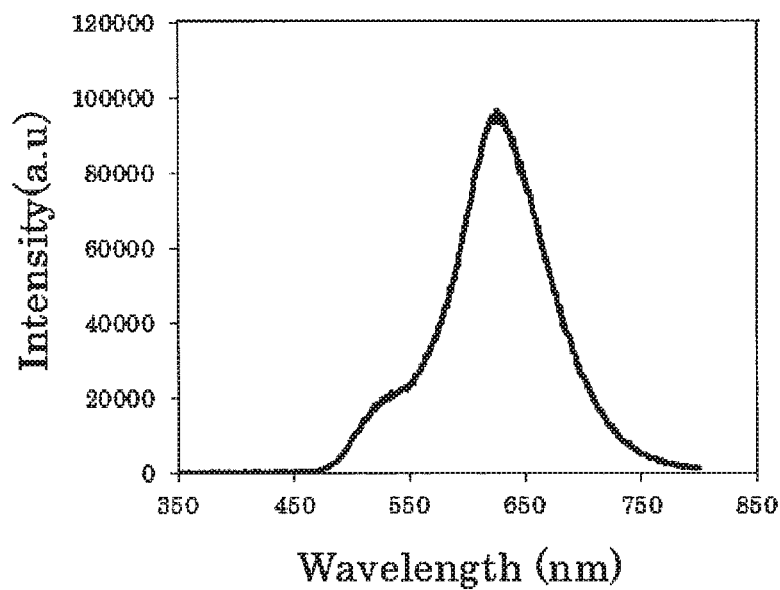
FIG. 10 shows the light emission spectrum of the thin film organic photoluminescent device of the compound 2 in Example 2.
Figure 11:
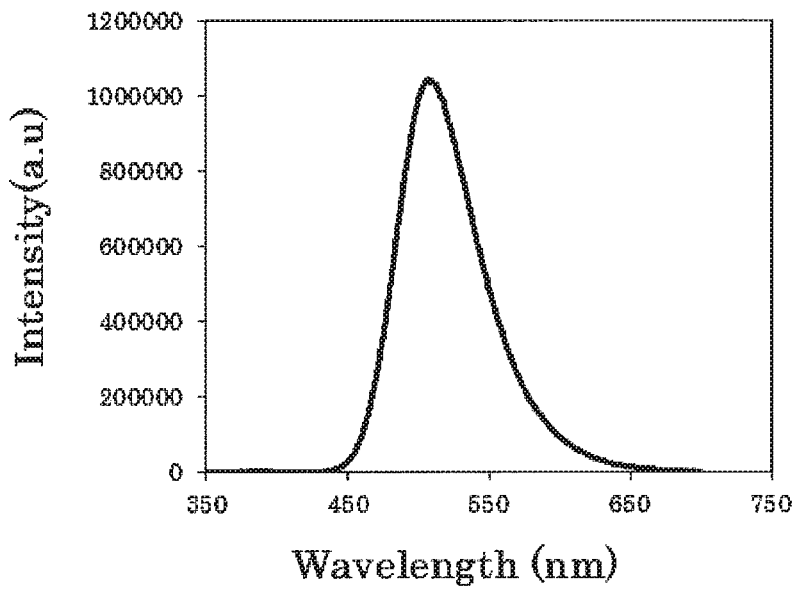
FIG. 11 shows the light emission spectrum of the thin film organic photoluminescent device of the compound 2 and mCP in Example 2.

The specimens using the compound 2 were measured for light emission spectrum with excitation light of 337 nm. FIG. 8 shows the light absorption and emission spectra of the toluene solution. FIG. 9 shows the light absorption spectrum of the organic photoluminescent device having the thin film containing only the compound 2, and FIG. 10 shows the light emission spectrum thereof. FIG. 11 shows the light emission spectrum of the organic photoluminescent device having the thin film containing the compound 2 and mCP.

For the toluene solution, the maximum light emission wavelength was 506 nm, and the photoluminescence quantum efficiency was 76.5% in the air and 81.5% after deaeration. For the organic photoluminescent device having the thin film containing only the compound 2, the maximum light emission wavelength was 626 nm, and the photoluminescence quantum efficiency was 49%. For the organic photoluminescent device having the thin film containing the compound 2 and mCP, the photoluminescence quantum efficiency was 100%.

The toluene solution of the compound 2 was measured for transient decay curves, the light emission lifetime τ in the air was 4.175 ns, and the light emission lifetime $\tau_1$ after deaeration was 5.412 ns.

Figure 12:
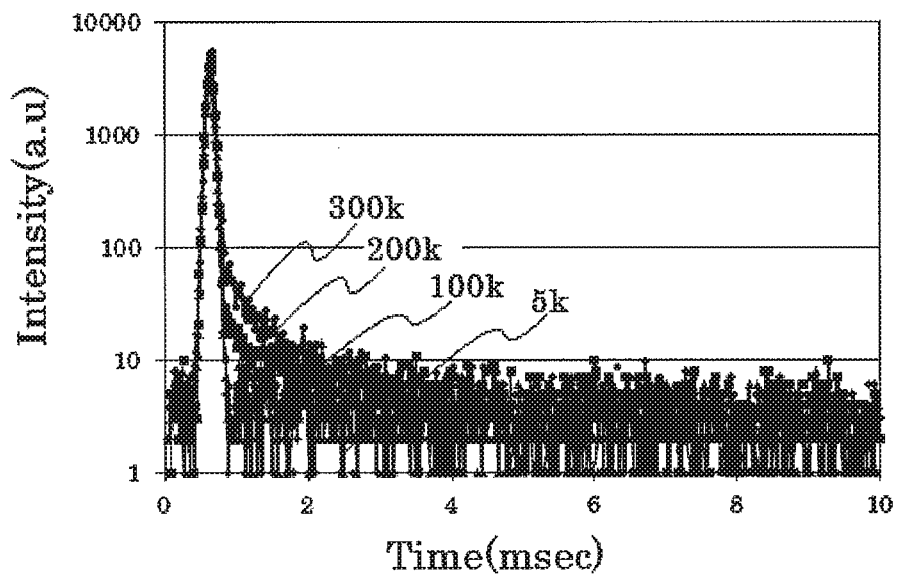
FIG. 12 shows the transient decay curves of the thin film organic photoluminescent device of the compound 2 and mCP in Example 2.

The organic photoluminescent device having the thin film containing the compound 2 and mCP was measured for transient decay curves at temperatures of 300 K, 200 K, 100 K, and 5 K. The results are shown in FIG. 12. FIG. 12 confirmed thermal activation type delayed fluorescent light with the delayed fluorescent light component that increased with the temperature rise.

Comparative Example 1

Production and Evaluation of Organic Photoluminescent Device Using Comparative Compound 1

A dichloromethane solution of the comparative compound 1 and an organic photoluminescent device having a thin film containing only the comparative compound 1 were produced by changing the point that the comparative compound 1 was used instead of the compound 1.

For the deaerated dichloromethane solution, the light emission wavelength peak was 363 nm, and the light emission quantum efficiency was 48%. The light emission lifetime τ was 4.795 ns, and no delayed component was observed. For the neat thin film, the light emission wavelength peak was 381 nm, and the light emission quantum efficiency was 30%. The light emission lifetime was 4.993 ns, and no delayed component was observed.

Comparative Example 2

Production and Evaluation of Organic Photoluminescent Device Using Comparative Compound 2

A toluene solution of the comparative compound 2 and an organic photoluminescent device having a thin film containing only the comparative compound 2 were produced by changing the point that the comparative compound 2 was used instead of the compound 1.

For the deaerated toluene solution, the light emission wavelength peak was 395 nm, and the light emission quantum efficiency was 41%. The light emission lifetime τ was 0.91 ns, and no delayed component was observed. For the neat thin film, the light emission wavelength peak was 393 nm, and the light emission quantum efficiency was 25%. The light emission lifetime was 0.807 ns, and no delayed component was observed.

Example 3

Production and Evaluation of Organic Electroluminescent Device Using Compound 2

Thin films were laminated on a glass substrate having formed thereon an anode formed of indium tin oxide (ITO) having a thickness of 100 nm, by a vacuum vapor deposition method at a vacuum degree of $4 \times 10^{-4}$ Pa. Firstly, HATCN was formed to a thickness of 10 nm on ITO, and then TrisPCZ was formed to a thickness of 30 nm thereon. Subsequently, the compound 2 and mCBP were co-deposited thereon from separate vapor deposition sources to form a layer having a thickness of 30 nm, which was designated as a light-emitting layer. At this time, the concentration of the compound 2 was 6% by weight. T2T was then formed to a thickness of 10 nm, and BPyTP2 was formed to a thickness of 30 nm, 40 nm, or 50 nm thereon. Lithium fluoride (LiF) was further vacuum vapor-deposited to a thickness of 0.8 nm, and then aluminum (Al) was vapor-deposited to a thickness of 100 nm to form a cathode. Three organic electroluminescent devices different in thickness of BPyTP2 were produced by the aforementioned process.

Figure 13:
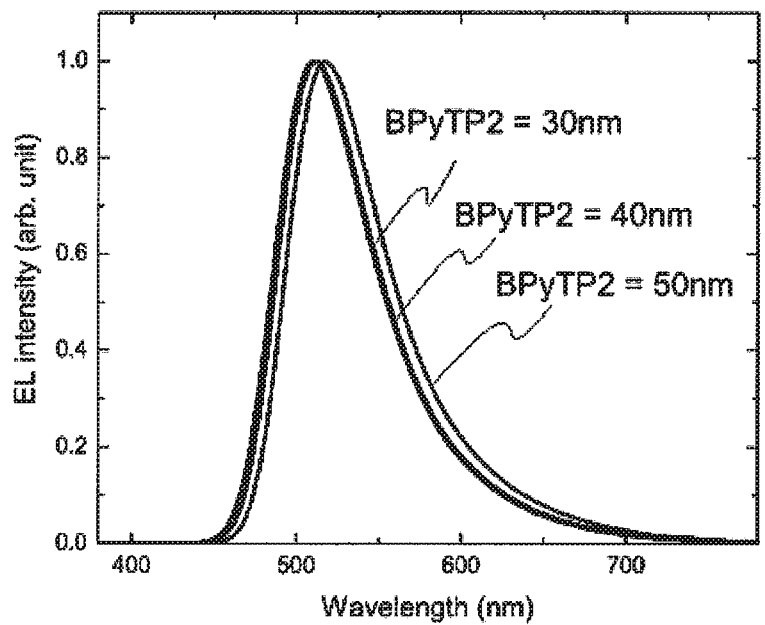
FIG. 13 shows the light emission spectra of the organic electroluminescent devices using the compound 2 in Example 3.
Figure 14:
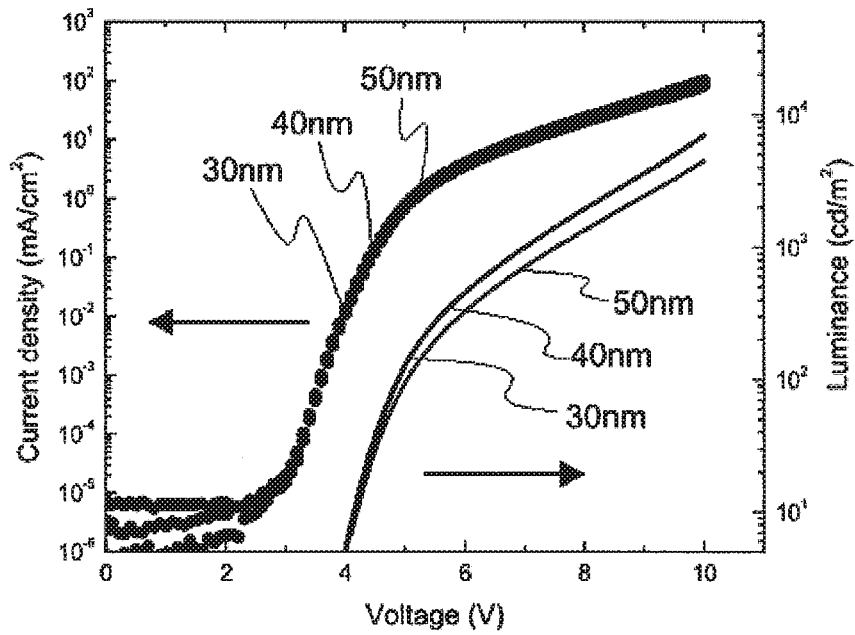
FIG. 14 is a graph showing the voltage-current density-luminance characteristics of the organic electroluminescent devices using the compound 2 in Example 3.
Figure 15:
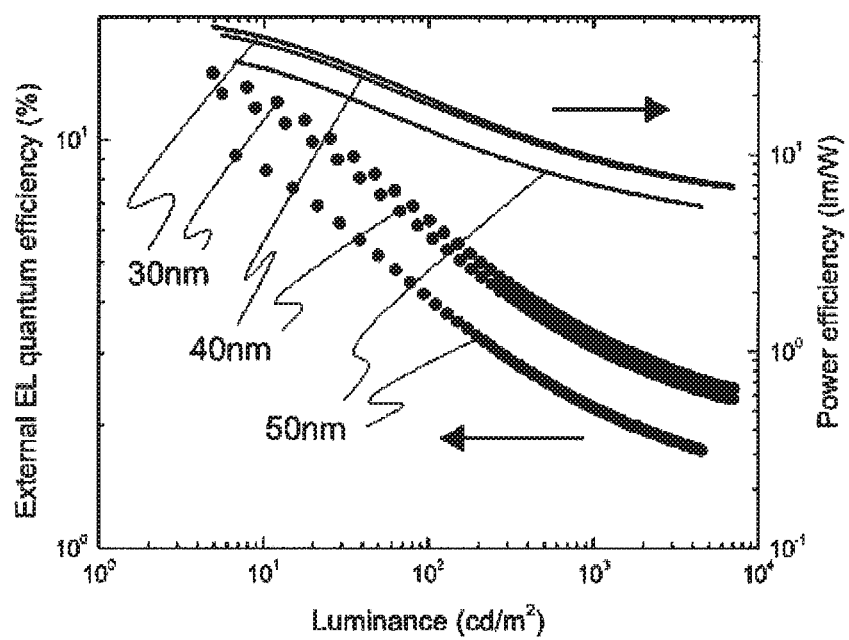
FIG. 15 is a graph showing the luminance-external quantum efficiency-electric power efficiency characteristics of the organic electroluminescent devices using the compound 2 in Example 3

FIG. 13 shows the light emission spectra of the organic electroluminescent devices thus produced, FIG. 14 shows the voltage-current density-luminance characteristics thereof, and FIG. 15 shows luminance-external quantum efficiency-electric power efficiency characteristics thereof. The organic electroluminescent devices using the compound 2 as a light-emitting material achieved a high external quantum efficiency of 14.6%. If an ideally balanced organic electroluminescent device is produced by using a fluorescent material having a light emission quantum efficiency of 100%, the external quantum efficiency of the fluorescent light emission may be from 5 to 7.5% assuming that the light extraction efficiency is from 20 to 30%. It has been ordinarily considered that this value is the theoretical limit value of an external quantum efficiency of an organic electroluminescent device using a fluorescent material. Accordingly, the organic electroluminescent devices of the invention using the compound 2 are considerably excellent in such a point that a high external quantum efficiency that exceeds the theoretical limit value is achieved.

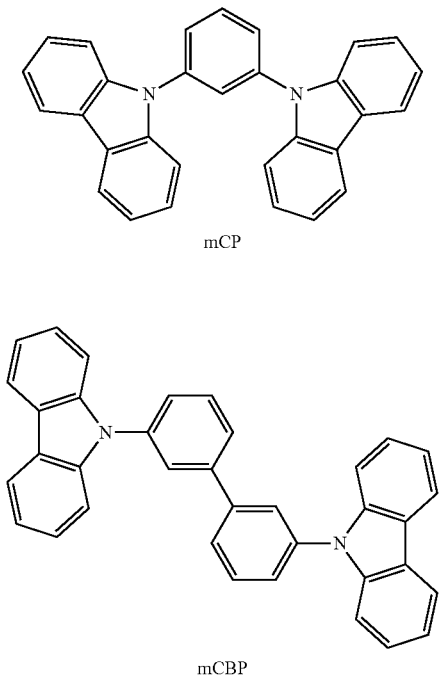

mCP

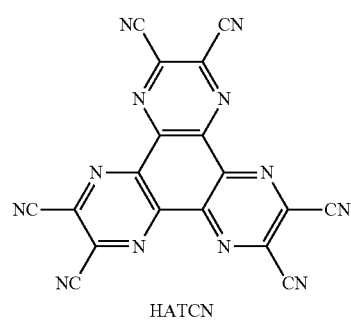

mCBP

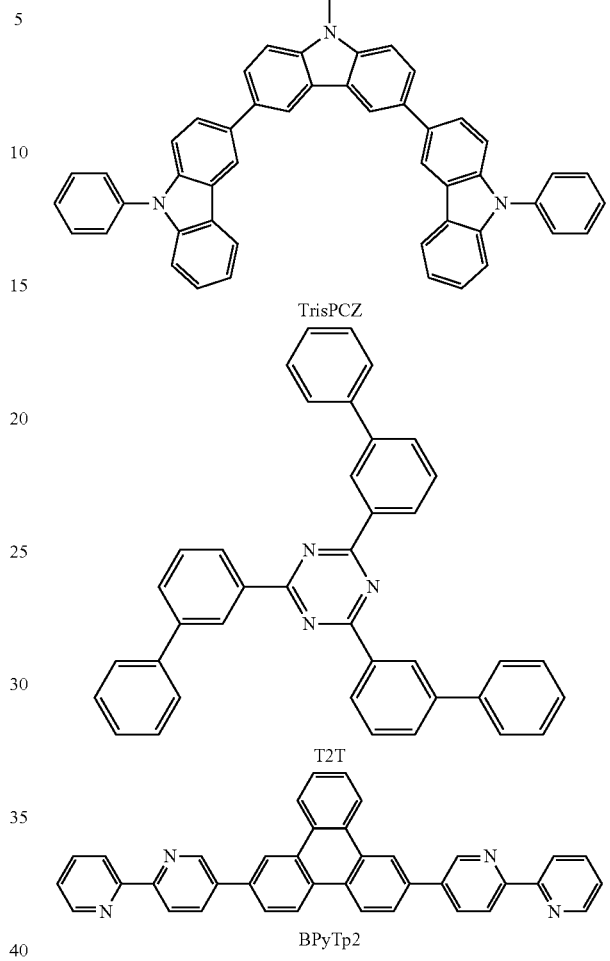

INDUSTRIAL APPLICABILITY

The compound of the invention is useful as a light-emitting material. Accordingly, the compound of the invention may be effectively used as a light-emitting material of an organic light-emitting device, such as an organic electroluminescent device. The compound of the invention includes a compound that emits delayed fluorescent light, and thus may be capable of providing an organic light-emitting device having a high light emission efficiency. Thus, the invention has high industrial applicability.

REFERENCE SIGNS LIST 1 substrate
2 anode
3 hole injection layer
4 hole transporting layer
5 light-emitting layer
6 electron transporting layer
7 cathode

The invention claimed is:
1. A compound represented by the following general formula (1'):

General Formula (1')

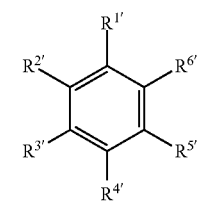

wherein in the general formula (1'), $R^{1'}$, $R^{3'}$, and $R^{5'}$ each represent a cyano group, or $R^{1'}$, $R^{2'}$, $R^{4'}$, and $R^{5'}$ each represent a cyano group; and the others of $R^{1'}$ to $R^{6'}$ each independently represent a group represented by any one of the following general formulae (2') to (8'), provided that when R1', R3', and R5' are a cyano group, then L12' to L18' in the general formulae (2') to (8') are a substituted or unsubstituted arylene group:

General Formula (2')

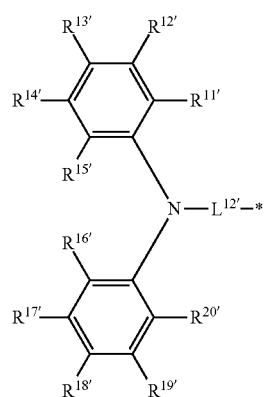

General Formula (3')

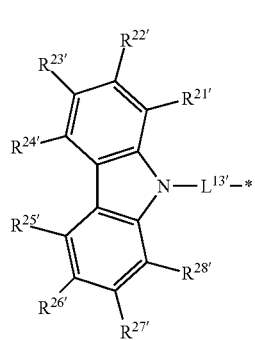

General Formula (4')

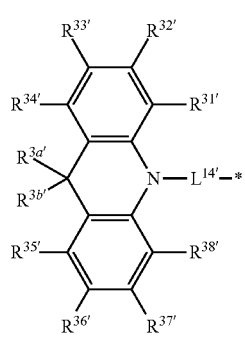

General Formula (5')

$$\text{[structure]}$$

General Formula (6')

$$\text{[structure]}$$

General Formula (7')

$$\text{[structure]}$$

General Formula (8')

$$\text{[structure]}$$

wherein in the general formulae (2') to (8'), $L^{12'}$ to $L^{18'}$ each represent a single bond or a substituted or unsubstituted arylene group; * represents a position bonded to the benzene ring in the general formula (1); and $R^{11'}$ to $R^{20'}$, $R^{21'}$ to $R^{28'}$, $R^{31'}$ to $R^{38'}$, $R^{3a'}$, $R^{3b'}$, $R^{41'}$ to $R^{48'}$, $R^{4a'}$, $R^{51'}$ to $R^{58'}$, $R^{61'}$ to $R^{68'}$, and $R^{71'}$ to $R^{78'}$ each independently represent a hydrogen atom or a substituent, provided that $R^{11'}$ and $R^{12'}$, $R^{12'}$ and $R^{13'}$, $R^{13'}$ and $R^{14'}$, $R^{14'}$ and $R^{15'}$, $R^{16'}$ and $R^{17'}$, $R^{17'}$ and $R^{18'}$, $R^{18'}$ and $R^{19'}$, $R^{19'}$ and $R^{20'}$, $R^{21'}$ and $R^{22'}$, $R^{22'}$ and $R^{23'}$, $R^{23'}$ and $R^{24'}$, $R^{24'}$ and $R^{25'}$, $R^{25'}$ and $R^{26'}$, $R^{26'}$ and $R^{27'}$, $R^{27'}$ and $R^{28'}$, $R^{31'}$ and $R^{32'}$, $R^{32'}$ and $R^{33'}$, $R^{33'}$ and $R^{34'}$, $R^{35'}$ and $R^{36'}$, $R^{36'}$ and $R^{37'}$, $R^{37'}$ and $R^{38'}$, $R^{3a'}$ and $R^{3b'}$, $R^{41'}$ and $R^{42'}$, $R^{42'}$ and $R^{43'}$, $R^{43'}$ and $R^{44'}$, $R^{45'}$ and $R^{46'}$, $R^{46'}$ and $R^{47'}$, $R^{47'}$ and $R^{48'}$, $R^{51'}$ and $R^{52'}$, $R^{52'}$ and $R^{53'}$, $R^{53'}$ and $R^{54'}$, $R^{55'}$ and $R^{56'}$, $R^{56'}$ and $R^{57'}$, $R^{57'}$ and $R^{58'}$, $R^{61'}$ and $R^{62'}$, $R^{62'}$ and $R^{63'}$, $R^{63'}$ and $R^{64'}$, $R^{65'}$ and $R^{66'}$, $R^{66'}$ and $R^{67'}$, $R^{67'}$ and $R^{68'}$, $R^{71'}$ and $R^{72'}$, $R^{72'}$ and $R^{73'}$, $R^{73'}$ and $R^{74'}$, $R^{75'}$ and $R^{76'}$, $R^{76'}$ and $R^{77'}$, and $R^{77'}$ and $R^{78'}$ each may be bonded to each other to form a cyclic structure.

2. An organic light-emitting device comprising a compound represented by the following general formula (1):

General Formula (1)

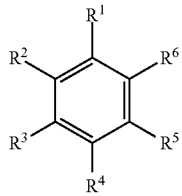

wherein in the general formula (1), $R^1$, $R^3$, and $R^5$ each represent a cyano group, or $R^1$, $R^2$, $R^4$, and $R^5$ each represent a cyano group; and the others of $R^1$ to $R^6$ each independently represent a group represented by any one of the following general formulae (2) to (8):

provided that when R1, R3, and R5 are a cyano group, then L12 to L18 in the general formulae (2) to (8) are a substituted or unsubstituted arylene group General Formula (2)

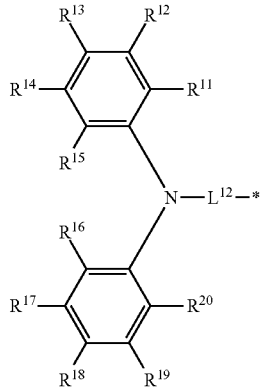

General Formula (3)

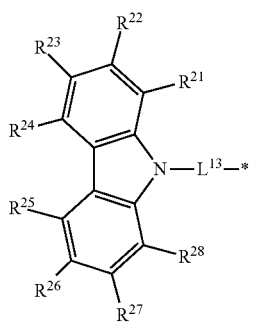

General Formula (4)

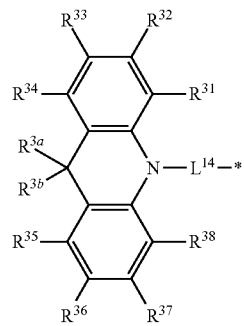

General Formula (5)

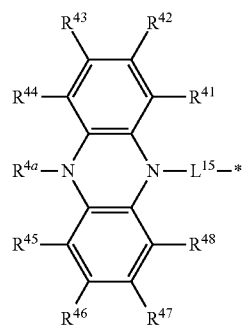

General Formula (6)

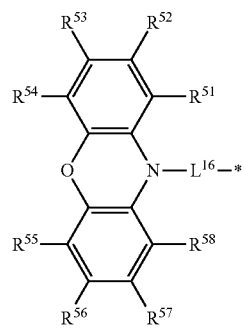

General Formula (7)

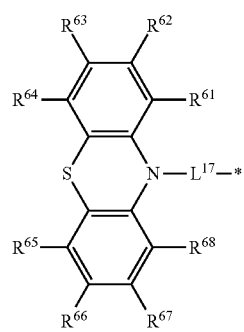

-continued

General Formula (8)

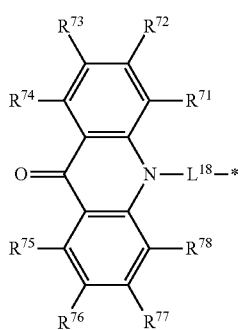

wherein in the general formulae (2) to (8), $L^{12}$ to $L^{18}$ each represent a single bond or a substituted or unsubstituted arylene group; * represents a position bonded to the benzene ring in the general formula (1); and $R^{11}$ to $R^{20}$, $R^{21}$ to $R^{28}$, $R^{31}$ to $R^{38}$, $R^{3a}$, $R^{3b}$, $R^{41}$ to $R^{48}$, $R^{4a}$, $R^{51}$ to $R^{58}$, $R^{61}$ to $R^{68}$, and $R^{71}$ to $R^{78}$ each independently represent a hydrogen atom or a substituent, provided that $R^{11}$ and $R^{12}$, $R^{12}$ and $R^{13}$, $R^{13}$ and $R^{14}$, $R^{14}$ and $R^{15}$, $R^{16}$ and $R^{17}$, $R^{17}$ and $R^{18}$, $R^{18}$ and $R^{19}$, $R^{19}$ and $R^{20}$, $R^{21}$ and $R^{22}$, $R^{22}$ and $R^{23}$, $R^{23}$ and $R^{24}$, $R^{24}$ and $R^{25}$, $R^{25}$ and $R^{26}$, $R^{26}$ and $R^{27}$, $R^{27}$ and $R^{28}$, $R^{31}$ and $R^{32}$, $R^{32}$ and $R^{33}$, $R^{33}$ and $R^{34}$, $R^{35}$ and $R^{36}$, $R^{36}$ and $R^{37}$, $R^{37}$ and $R^{38}$, $R^{3a}$ and $R^{3b}$, $R^{41}$ and $R^{42}$, $R^{42}$ and $R^{43}$, $R^{43}$ and $R^{44}$, $R^{45}$ and $R^{46}$, $R^{46}$ and $R^{47}$, $R^{47}$ and $R^{48}$, $R^{51}$ and $R^{52}$, $R^{52}$ and $R^{53}$, $R^{53}$ and $R^{54}$, $R^{55}$ and $R^{56}$, $R^{56}$ and $R^{57}$, $R^{57}$ and $R^{58}$, $R^{61}$ and $R^{62}$, $R^{62}$ and $R^{63}$, $R^{63}$ and $R^{64}$, $R^{65}$ and $R^{66}$, $R^{66}$ and $R^{67}$, $R^{67}$ and $R^{68}$, $R^{71}$ and $R^{72}$, $R^{72}$ and $R^{73}$, $R^{73}$ and $R^{74}$, $R^{75}$ and $R^{76}$, $R^{76}$ and $R^{77}$, and $R^{77}$ and $R^{78}$ each may be bonded to each other to form a cyclic structure.

3. The organic light-emitting device according to claim 2, wherein in the general formula (1), $R^1$, $R^3$, and $R^5$ each represent a cyano group.

4. The organic light-emitting device according to claim 2, wherein in the general formula (1), $R^1$, $R^2$, $R^4$, and $R^5$ each represent a cyano group.

5. The organic light-emitting device according to claim 2, wherein in the general formulae (2) to (8), $L^{12}$ to $L^{18}$ each represent a substituted or unsubstituted phenylene group.

6. The organic light-emitting device according to claim 2, wherein in the general formula (1), all the others of $R^1$ to $R^6$ each represent a group represented by the general formula (2).

7. The organic light-emitting device according to claim 2, wherein in the general formula (1), all the others of $R^1$ to $R^6$ each represent a group represented by the general formula (3).

8. The organic light-emitting device according to claim 2, wherein the molecule has a rotationally symmetric structure.

9. The organic light-emitting device according to claim 2, wherein the organic light-emitting device emits delayed fluorescent light.

10. The organic light-emitting device according to claim 2, wherein the organic light-emitting device is an organic electroluminescent device.

* * * * *